US012611396B2

(12) United States Patent
Li

(10) Patent No.: US 12,611,396 B2
(45) Date of Patent: *Apr. 28, 2026

(54) MICROSPHERE-BASED INJECTIBLE CELECOXIB FORMULATION

(71) Applicant: Avidence Therapeutics, Inc., New York, NY (US)

(72) Inventor: Ang Li, Brooklyn, NY (US)

(73) Assignee: Avidence Therapeutics, Inc.

( * ) Notice: Subject to any disclaimer, the term of this patent is extended or adjusted under 35 U.S.C. 154(b) by 763 days.

This patent is subject to a terminal disclaimer.

(21) Appl. No.: 17/629,822

(22) PCT Filed: Aug. 6, 2020

(86) PCT No.: PCT/US2020/045099
§ 371 (c)(1),
(2) Date: Jan. 25, 2022

(87) PCT Pub. No.: WO2021/026289
PCT Pub. Date: Feb. 11, 2021

(65) Prior Publication Data
US 2022/0257565 A1       Aug. 18, 2022

Related U.S. Application Data

(60) Provisional application No. 62/884,526, filed on Aug. 8, 2019.

(51) Int. Cl.
*A61K 31/415* (2006.01)
*A61K 9/00* (2006.01)
*A61K 9/16* (2006.01)
*A61K 47/10* (2017.01)
*A61P 19/02* (2006.01)

(52) U.S. Cl.
CPC .......... *A61K 31/415* (2013.01); *A61K 9/0019* (2013.01); *A61K 9/16* (2013.01); *A61K 47/10* (2013.01); *A61P 19/02* (2018.01)

(58) Field of Classification Search
CPC ......... A61K 31/415; A61K 9/16; A61K 47/34
See application file for complete search history.

(56) References Cited

U.S. PATENT DOCUMENTS

| | | | |
|---|---|---|---|
| 9,555,048 B2 | 1/2017 | Bodick et al. | |
| 2007/0249632 A1 * | 10/2007 | Zentner ................... | A61P 35/00 514/258.1 |
| 2011/0117197 A1 | 5/2011 | Emanuel et al. | |
| 2022/0096498 A1 * | 3/2022 | Ugwu ................. | A61K 9/1682 |

FOREIGN PATENT DOCUMENTS

| | | | |
|---|---|---|---|
| WO | 1997/028828 A1 | 8/1997 | |
| WO | 2013/019280 A1 | 2/2013 | |
| WO | 2017/085561 A1 | 5/2017 | |
| WO | WO-2019193417 A1 * | 10/2019 | ........... A61K 31/341 |

OTHER PUBLICATIONS

Anderson, et al., Biodegradation and biocompatibility of PLA and PLGA microspheres, Advanced Drug Delivery 28 (1997): 5-24.
Berchane, et al., "Effect of mean diameter and polydispersity of PLG microspheres on drug release: Experiment and theory", International Journal of Pharmaceutics 337 (2007) 118-126.
Berkland, et al., "PLG microsphere size controls drug release rate through several competing factors", Pharmaceutical Research vol. 20, No. 7, Jul. 2003, pp. 1055-1062.
Bouissou, et al., Poly(lactic-co-glycolic-acid) Microspheres. Polymer in Drug Delivery (2006): Chapter 7.
Cannava, et al., "Celecoxib-loaded PLGA/cyclodextrin microspheres: characterization and evaluation of anti-inflammatory activity on human chondrocyte cultures", Colloids and Surfaces B: Biointerfaces, vol. 111, pp. 289-296, 2013.
Chaisri, et al., "Enhanced gentamicin loading and release of PLGA and PLHMGA microspheres by varying the formulation parameters". Colloids and Surfaces B: Biointerfaces. vol. 84, 2011, pp. 508-514).
Champion, et al., "Role of Particle Size in Phagocytosis of Polymeric Microspheres", Pharmaceutical Research, vol. 25, pp. 1815-1821 (2008).
Chikaura, et al., Effect of particle size on biological response by human monocyte-derived macrophages, Biosurface and Biotribology, Mar. 2016. 2(1):18-25.
Cleek, et al., "Microparticles of poly(DL-lactic-co-glycolic acid) / poly (ethylene glycol) blends for controlled drug delivery", Journal of Controlled Release 48 (1997) 259-268.
Duvvuri, et al., "Effect of polymer blending on the release of ganciclovir from PLGA microspheres", Pharmaceutical Research, vol. 23, No. 1, Jan. 2006.
FDA Label for Celebrex® (celecoxib).
FDA Label for Zilretta® (a PLGA-triamcinolone-acetonide microsphere formulation).
Fredenberg, et al., "The mechanisms of drug release in poly(lactic-co-glycolic acid)-based drug delivery systems—A review", International Journal of Pharmaceutics 415 (2011) 34-52.
T. Green, et al., Polyethylene particles of a critical size are necessary for the induction of cytokines by macrophages in vitro, Biomaterials, Dec. 1998; 19(24): 2297-2302.
Han, et al., "Bioerodable PLGA-Based Microparticles for Producing Sustained Released Drug Formulations and Strategies for Improving Drug Loading", Frontiers in Pharmacology, vol. 7, Article 185, Jun. 2016.

(Continued)

*Primary Examiner* — Michael B. Pallay
(74) *Attorney, Agent, or Firm* — Law Offices of Alan J. Morrison

(57) ABSTRACT

This invention provides a biodegradable microsphere, wherein the microsphere (i) has a diameter of from 1 ?m to 500 ?m; (ii) comprises a polylactic-co-glycolic acid copolymer (PLGA) matrix; (iii) carries pharmaceutical celecoxib; and (iv) when present in a suitable joint-related tissue, releases celecoxib for at least one month. This invention also provides related injectable formulations, methods for treating joint-related disorders, and kits.

25 Claims, 55 Drawing Sheets

(56) References Cited

OTHER PUBLICATIONS

Hebei Medical University, "The inhibitive releasing ability of sustained releasing CEL-PLGA-MS in experimental choroidal neovascularization", Chinese Doctoral Dissertations & Masters Theses—Full Text Database (Master) (2013) [English portion only].

M. Homar, et al., Influence of polymers on the bioavailability of micro-encapsulated celecoxib, J. of Microencapsulation, Nov. 2007; 24(7): 621-633.

Hua, et al., "Poly(lactic co-glycolic acid) microsphere production based on quality by design: a review", Drug Delivery, 28:1, 1342-1355 (2021).

Hunter et al. (2004) Plasma pharmacokinetics and synovial fluid concentrations after oral administration of single and multiple doses of celecoxib in Greyhounds. AJVR. vol 66, No. 8.

M. Janssen, et al., Celecoxib-loaded PEA microspheres as an auto regulatory drug-delivery system after intra-articular injection, J. Control Release, Dec. 2016. 28:244 (Pt. A): 30-40.

Lagreca, et al., "Recent advances in the formulation of PLGA microparticles for controlled drug delivery", Progress in Biomaterials (2020) 9:153-174.

Li, et al., "Preparation of ropivacaine loaded PLGA microspheres as controlled-release system with narrow size distribution and high loading efficiency." Colloids and Surfaces A. vol. 562, 2019 (available online in Nov. 2018), pp. 237-246.

Li, et al., "High drug-loaded microspheres enabled by controlled in-droplet precipitation promote functional recovery after spinal cord injury", Nature Communications, (2022)13:1262.

J. Matthews, et al., Comparison of the response of primary human peripheral blood mononuclear phagocytes from different donors to challenge with model polyethylene particles of known size and dose, Biomaterials. Oct. 2000. 21(20):2033-2044.

Morlock, et al. Erythropoietin loaded microspheres prepared from biodegradable LPLG-PEO-LPLG triblock copolymers: protein stabilization and in vitro release properties. J Control Release, 56(1-3) (1998):105-15.

Park, et al., "Injectable, long-acting PLGA formulations: Analyzing PLGA and understanding microparticle formation." Journal of Controlled Release. vol. 304, May 2019, pp. 125-134).

S.K. Paulson, et al., Pharmacokinetics of celecoxib after oral administration in dogs and humans: effect of food and site of absorption, The Journal of Pharmacology and Experimental Therapeutics. (2001) 297(2):638-45.

A. Petit, et al., Release behavior and intra-articular biocompatibility of celecoxib-loaded acetyl-capped PCLA-PEG-PCLA thermogels, Biomaterials 35 (2014) 7919-7928.

A. Petit, et al., Sustained intra-articular release of celecoxib from in situ forming gels made of acetyl-capped PCLA-PEG-PCLA triblock copolymers in horses, Biomaterials 35 (2015): 426-436.

Search results for cyclodextrin, "Inactive Ingredient Search for Approved Drug Products", U.S. Food & Drug Administration website (2023).

Shen, et al., "In vitro-in vivo correlation of parenteral risperidone polymeric microspheres", Journal of Controlled Release 218 (2015) 2-12.

H. Thakkar, et al., Celecoxib incorporated chitosan microspheres: in vitro and in vivo evaluation, J. of Drug Targeting, Oct.-Dec. 2004, vol. 12 (9-10), pp. 549-557.

H. Thakkar, et al., Enhanced retention of celecoxib-loaded solid lipid nano-particles after intra-articular administration, Drugs R D 2007; 8(5):275-285.

Wang, et al. (2011) Intra-discal vancomycin-loaded PLGA microsphere injection for MRSA discitis: an experimental study. Arch Orthop Trauma Surg. 131:111-119.

Williems, et al. (2017) Safety of intradiscal injection and biocompatibility of polyester amide microspheres in a canine model predisposed to intervertebral disc degeneration. Journal of Biomedical Materials Research Part B. 105(4):707-714.

H.Y. Yang, et al., Applicability of a newly developed bioassay for determining bioactivity of anti-inflammatory compounds in release studies—celecoxib and triamcinolone acetonide released from novel PLGA-based microspheres, Pharm. Res. (2015) 32:680-690.

Yeh, "The stability of insulin in biodegradable microparticles based on blends of lactide polymers and polyethylene glycol." J Microencapsul, 17(6) (2000):743-56.

FDA Label for Vioxx (rofecoxib).

Jin and Sohn, "Crystal Form of Celecoxib: Preparation, Characterization and Dissolution", Journal of the Korean Chemical Society, 2018, vol. 62, No. 5.

Jigar, et al., "Formulation and evaluation of solid dispersions of Rofecoxib for improvement of dissolution profile", African Journal of Pharmacy and Pharmacology, vol. 5(5), 577-581 (May 2011).

Nasr, "In Vitro and In Vivo Evaluation of Proniosomes Containing Celecoxib for Oral Administration", AAPS PharmSciTech, vol. 11, No. 1, Mar. 2010.

An, et al., International Journal of Pharmaceutics, 2016, vol. 503, 8-15.

Rothstein and Little, Journal of Materials Chemistry, 2011, vol. 21, No. 29.

Makadia and Siegel, Polymers (Basel), 2011, vol. 3(3), 1377-1397.

* cited by examiner

50mg PLGA+20mg diclofenac acid
Dissolved in 440µl dichloromethane+60µl DMSO
Stirred at 2000rpm in 200ml 1% PVA ● PLGA50:50, 0.6dl/g, ester-terminated
■ PLGA75:25, 0.65dl/g, ester-terminated
▲ PLGA85:15, 0.6dl/g, ester-terminated
▼ PDLA, 2dl/g, ester-terminated 5mg PLGA+2mg diclofenac acid
Dissolved in 180µl dichloromethane+20µl DMSO
Stirred at 1000rpm in 50ml 1% PVA

- 25% PLGA50:50, 0.2dl/g, acid-terminated+75% PLGA85:15, 0.6dl/g, ester-terminated
- 50% PLGA50:50, 0.2dl/g, acid-terminated+50% PLGA85:15, 0.6dl/g, ester-terminated
- 25% PLGA50:50, 0.2dl/g, acid-terminated+75% PDLA, 0.4dl/g, ester-terminated
- 50% PLGA50:50, 0.2dl/g, acid-terminated+50% PDLA, 0.4dl/g, ester-terminated 5mg PLGA+2mg diclofenac acid
Dissolved in 180μl dichloromethane+20μl DMSO
Stirred at 1000rpm in 50ml 1% PVA ● 100% PLGA75:25, 0.65dl/g, ester-terminated
■ 75% PLGA75:25, 0.65dl/g, ester-terminated+25% PLGA50:50, 0.2dl/g, acid-terminated
▲ 50% PLGA75:25, 0.65dl/g, ester-terminated+50% PLGA50:50, 0.2dl/g, acid-terminated
▼ 25% PLGA75:25, 0.65dl/g, ester-terminated+75% PLGA50:50, 0.2dl/g, acid-terminated

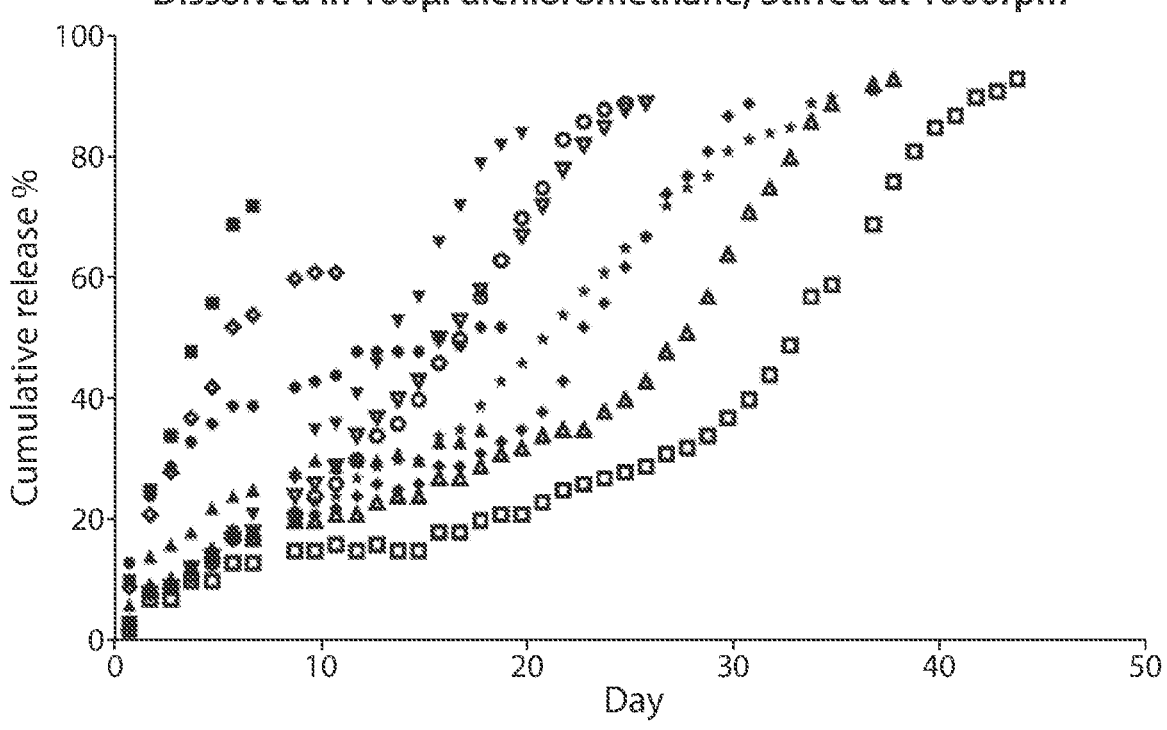

2.5mg PLGA+1mg celecoxib
Dissolved in 100µl dichloromethane, Stirred at 1000rpm

*   PLGA50:50, 0.2dl/g, acid-terminated
▲   PLGA50:50, 0.2dl/g, ester-terminated
▼   PLGA50:50, 0.4dl/g, acid-terminated
*   PLGA50:50, 0.4dl/g, ester-terminated
○   PLGA50:50, 0.5dl/g, acid-terminated
□   PLGA50:50, 0.5dl/g, ester-terminated
▲   PLGA50:50, 0.6dl/g, ester-terminated
▼   PLGA65:35, 0.4dl/g, acid-terminated
◆   PLGA75:25, 0.2dl/g, acid-terminated
*   PLGA75:25, 0.2dl/g, ester-terminated
*   PLGA75:25, 0.4dl/g, acid-terminated

FIGURE 7

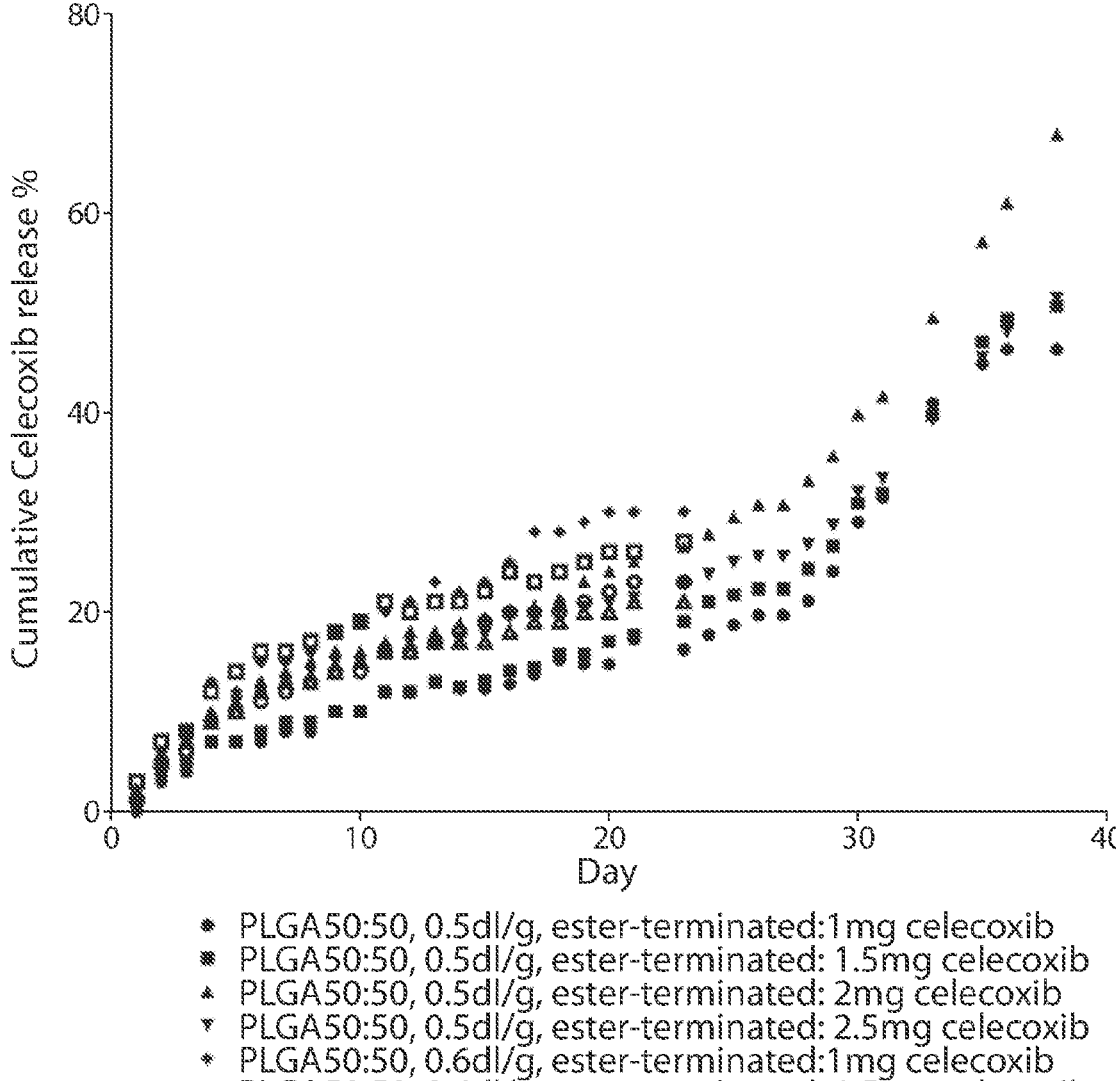

2.5mg PLGA, different loading amount of celecoxib,
Dissolved in 200µl dichloromethane, Stirred at 1000rpm

* PLGA50:50, 0.5dl/g, ester-terminated:1mg celecoxib
* PLGA50:50, 0.5dl/g, ester-terminated: 1.5mg celecoxib
▲ PLGA50:50, 0.5dl/g, ester-terminated: 2mg celecoxib
▼ PLGA50:50, 0.5dl/g, ester-terminated: 2.5mg celecoxib
* PLGA50:50, 0.6dl/g, ester-terminated:1mg celecoxib
○ PLGA50:50, 0.6dl/g, ester-terminated: 1.5mg celecoxib
□ PLGA50:50, 0.6dl/g, ester-terminated: 2mg celecoxib
▲ PLGA50:50, 0.6dl/g, ester-terminated: 2.5mg celecoxib

FIGURE 8

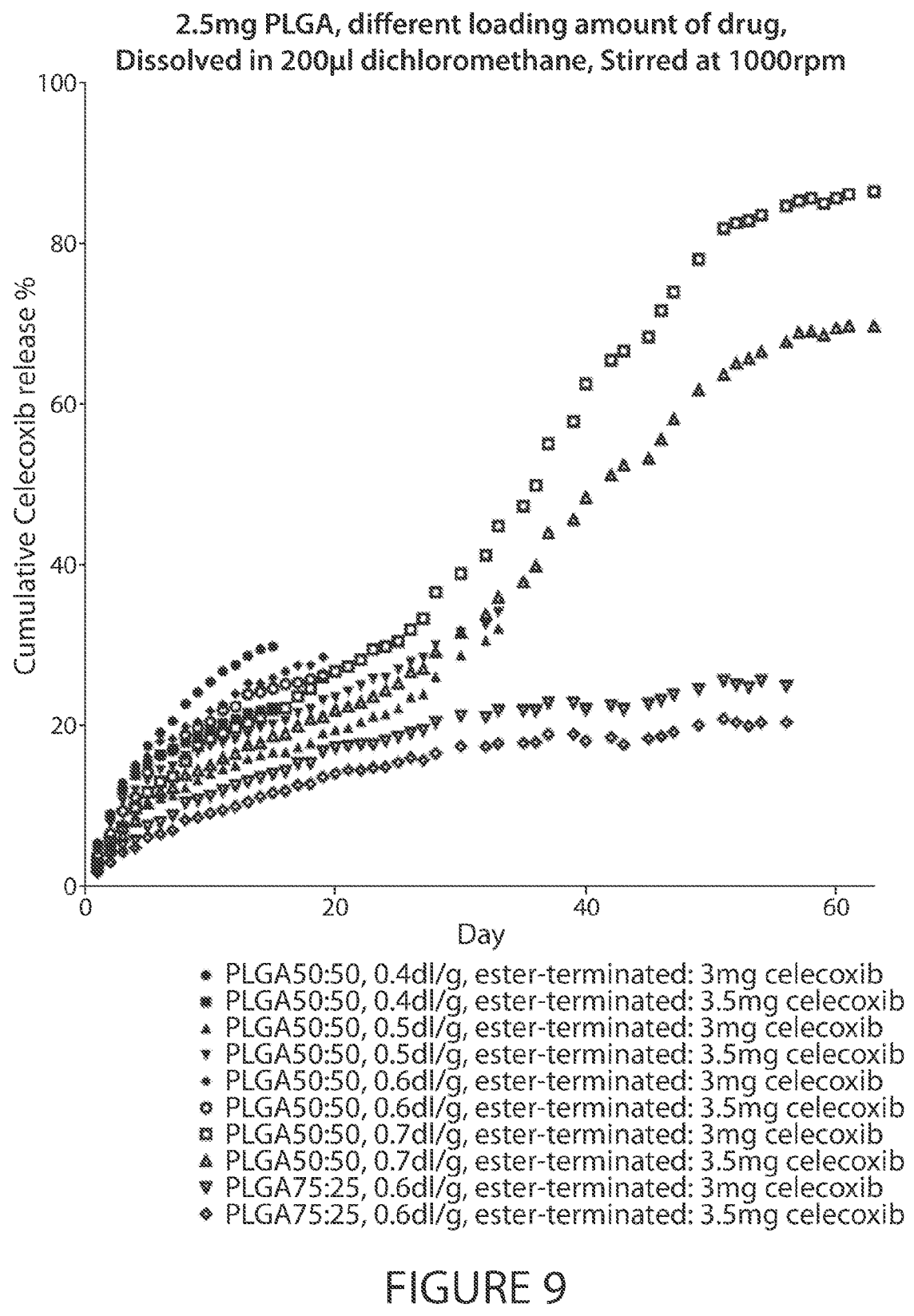

2.5mg PLGA, different loading amount of drug,
Dissolved in 200μl dichloromethane, Stirred at 1000rpm

* PLGA50:50, 0.4dl/g, ester-terminated: 3mg celecoxib
* PLGA50:50, 0.4dl/g, ester-terminated: 3.5mg celecoxib
▲ PLGA50:50, 0.5dl/g, ester-terminated: 3mg celecoxib
▼ PLGA50:50, 0.5dl/g, ester-terminated: 3.5mg celecoxib
* PLGA50:50, 0.6dl/g, ester-terminated: 3mg celecoxib
○ PLGA50:50, 0.6dl/g, ester-terminated: 3.5mg celecoxib
□ PLGA50:50, 0.7dl/g, ester-terminated: 3mg celecoxib
▲ PLGA50:50, 0.7dl/g, ester-terminated: 3.5mg celecoxib
▼ PLGA75:25, 0.6dl/g, ester-terminated: 3mg celecoxib
◆ PLGA75:25, 0.6dl/g, ester-terminated: 3.5mg celecoxib

FIGURE 9

2.5mg PLGA/PDLA+1mg celecoxib
Dissolved in 200µl dichloromethane, Stirred at 1000rpm ● 100% PDLA, 0.4dl/g, ester-terminated
■ 75% PDLA, 0.4dl/g, ester-terminated +25% PLGA50:50, 0.5dl/g, acid-terminated
▲ 50% PDLA, 0.4dl/g, ester-terminated+50% PLGA50:50, 0.5dl/g, acid-terminated
▼ 25% PDLA, 0.4dl/g, ester-terminated+75% PLGA50:50, 0.5dl/g, acid-terminated
◆ 100% PDGA50:50, 0.5dl/g, acid-terminated

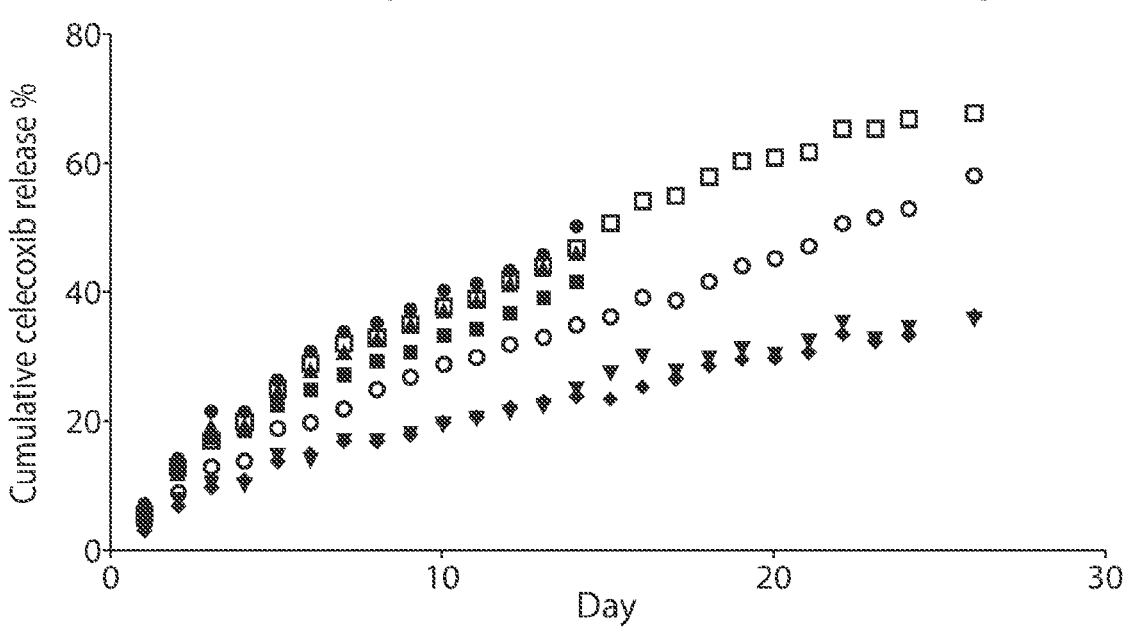

2.5mg PLGA+1mg celecoxib
Dissolved in 200µl dichloromethane, Stirred at 1000rpm

• 90% PLGA50:50, 0.4dl/g, ester-terminated + 10% PLGA50:50, 0.5dl/g, acid-terminated
▪ 75% PLGA50:50, 0.4dl/g, ester-terminated + 25% PLGA50:50, 0.5dl/g, acid-terminated
▲ 50% PLGA50:50, 0.4dl/g, ester-terminated + 50% PLGA50:50, 0.5dl/g, acid-terminated
▼ 90% PLGA50:50, 0.5dl/g, ester-terminated + 10% PLGA50:50, 0.5dl/g, acid-terminated
♦ 75% PLGA50:50, 0.5dl/g, ester-terminated + 25% PLGA50:50, 0.5dl/g, acid-terminated
○ 50% PLGA50:50, 0.5dl/g, ester-terminated + 50% PLGA50:50, 0.5dl/g, acid-terminated
□ PLGA50:50, 0.5dl/g, acid-terminated

FIGURE 11

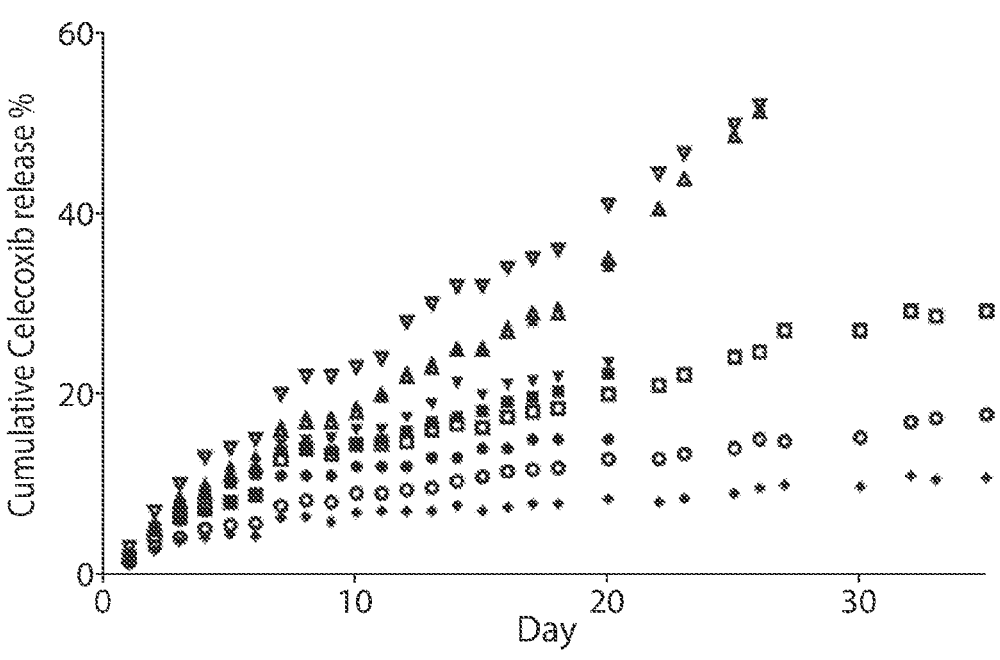

2.5mg PLGA+2.5mg celecoxib
Dissolved in 200µl dichloromethane, Stirred at 1000rpm ● 100% PLGA50:50, 0.5dl/g, ester-terminated
■ 75% PLGA50:50, 0.5dl/g, ester-terminated+25% PLGA50:50, 0.5dl/g, acid-terminated
▲ 50% PLGA50:50, 0.5dl/g, ester-terminated+50% PLGA50:50, 0.5dl/g, acid-terminated
▼ 25% PLGA50:50, 0.5dl/g, ester-terminated+75% PLGA50:50, 0.5dl/g, acid-terminated
◆ 100% PDLA, 0.4dl/g, ester-terminated
○ 75% PDLA, 0.4dl/g, ester-terminated+25% PLGA50:50, 0.5dl/g, acid-terminated
□ 50% PDLA, 0.4dl/g, ester-terminated+50% PLGA50:50, 0.5dl/g, acid-terminated
△ 25% PDLA, 0.4dl/g, ester-terminated+75% PLGA50:50, 0.5dl/g, acid-terminated
▽ 100% PLGA50:50, 0.5dl/g, acid-terminated

FIGURE 12

2.5mg Mixed PLGA, 3.5mg celecoxib
Dissolved in 200μl dichloromethane, Stirred at 1000rpm

- 100% PLGA75:25, 0.6dl/g, ester-terminated
- 75% PLGA75:25, 0.6dl/g, ester-terminated+25% PLGA50:50, 0.5dl/g, acid-terminated
- 50% PLGA75:25, 0.6dl/g, ester-terminated+50% PLGA50:50, 0.5dl/g, acid-terminated
- 25% PLGA75:25, 0.6dl/g, ester-terminated+75% PLGA50:50, 0.5dl/g, acid-terminated
- 100% PLGA50:50, 0.5dl/g, acid-terminated 2.5mg PLGA50:50, 0.5dl/g, ester-terminates+2.5mg celecoxib, Supplemented with PEG1450 Dissolved in 200µl dichloromethane, Stirred at 1000rpm

- • 0mg PEG1450 added
- ▪ 0.625mg PEG1450 added
- ▲ 1.25mg PEG1450 added
- ▼ 2.5mg PEG1450 added 2.5mg PLGA, different loading of celecoxib,
Dissolved in 100μl dichloromethane, Stirred at 1000rpm

* PLGA50:50, 0.5dl/g, acid-terminated+1mg celecoxib
■ PLGA75:25, 0.4dl/g, acid-terminated+1mg celecoxib
▲ PLGA75:25, 0.4dl/g, acid-terminated+1.5mg celecoxib
▼ PLGA75:25, 0.4dl/g, acid-terminated+2mg celecoxib
◆ PLGA75:25, 0.4dl/g, acid-terminated+2.5mg celecoxib 2.5mg PLGA75:25, 0.4dl/g, acid-terminated
Dissolved in 200µl dichloromethane, Stirred at 1000rpm

• 3.5mg celecoxib
■ 5mg celecoxib 2.5mg PLGA75:25, 0.4dl/g, acid-terminated+5mg celecoxib
Dissolved in 200μl dichloromethane, Stirred at 1200rpm 2.5mg PLGA, Dissolved in 200µl dichloromethane, Stirred at 1000rpm

* PLGA50:50, 0.5dl/g, ester-terminated+4mg celecoxib
* PLGA50:50, 0.5dl/g, ester-terminated+5mg celecoxib
* PLGA50:50, 0.5dl/g, ester-terminated+6mg celecoxib
* PLGA50:50, 0.6dl/g, ester-terminated+4mg celecoxib
* PLGA50:50, 0.6dl/g, ester-terminated+5mg celecoxib
* PLGA50:50, 0.6dl/g, ester-terminated+6mg celecoxib 2.5mg PLGA75:25, 0.9dl/g, ester-terminated
Stirred at 1000rpm ● Dissolved in 300µl dichloromethane-5mg celecoxib
■ Dissolved in 300µl dichloromethane-6mg celecoxib
▲ Dissolved in 300µl dichloromethane-7.5mg celecoxib
▼ Dissolved in 400µl dichloromethane-5mg celecoxib
◆ Dissolved in 400µl dichloromethane-6mg celecoxib 2.5mg PLGA75:25, 0.9dl/g, ester-terminated
Stirred at 1000rpm

* Dissolved in 300μl dichloromethane-6mg celecoxib
▓ Dissolved in 300μl dichloromethane-7.5mg celecoxib
▲ Dissolved in 400μl dichloromethane-5mg celecoxib
▼ Dissolved in 400μl dichloromethane-6mg celecoxib 2.5mg PLGA75:25, 0.9dl/g, ester-terminated
Dissolved in 300μl dichloromethane, Stirred at 1000rpm

- 5mg celecoxib
- 6mg celecoxib
- 7.5mg celecoxib 2.5mg PLGA85:15, 1.5dl/g, ester-terminated
Stirred in 1000rpm

* Dissolved in 300μl dichloromethane-5mg celecoxib
■ Dissolved in 300μl dichloromethane-6mg celecoxib
▲ Dissolved in 300μl dichloromethane-7.5mg celecoxib
▼ Dissolved in 400μl dichloromethane-5mg celecoxib
◆ Dissolved in 400μl dichloromethane-6mg celecoxib
◎ Dissolved in 400μl dichloromethane-7.5mg celecoxib 2.5mg PLGA85:15, 1.5dl/g, ester-terminated
Dissolved in 500μl dichloromethane, Stirred in 1000rpm

- 5mg celecoxib
- 7.5mg celecoxib

FIGURE 35

2.5mg PDLA, 0.6dl/g, ester-terminated, Stirred in 1000rpm

- Dissolved in 300μl dichloromethane-5mg celecoxib
- Dissolved in 300μl dichloromethane-6mg celecoxib
- Dissolved in 300μl dichloromethane-7.5mg celecoxib
- Dissolved in 400μl dichloromethane-5mg celecoxib
- Dissolved in 400μl dichloromethane-6mg celecoxib 2.5mg PLGA+5mg celecoxib,
Dissolved in 300μl dichloromethane, Stirred in 1000rpm

• 100% PLGA50:50, 0.7dl/g, ester-terminated
■ 75% PLGA50:50, 0.7dl/g, ester-terminated+25% PLGA75:25, 0.6dl/g, ester-terminated
▲ 50% PLGA50:50, 0.7dl/g, ester-terminated+50% PLGA75:25, 0.6dl/g, ester-terminated
▼ 25% PLGA50:50, 0.7dl/g, ester-terminated+75% PLGA75:25, 0.6dl/g, ester-terminated
♦ 100% PLGA75:25, 0.6dl/g, ester-terminated 2.5mg PLGA+5mg celecoxib,
Dissolved in 200µl dichloromethane, Stirred in 1200rpm

- 100% PLGA50:50, 0.7dl/g, ester-terminated
- 75% PLGA50:50, 0.7dl/g, ester-terminated+25% PLGA75:25, 0.6dl/g, ester-terminated
- 50% PLGA50:50, 0.7dl/g, ester-terminated+50% PLGA75:25, 0.6dl/g, ester-terminated
- 25% PLGA50:50, 0.7dl/g, ester-terminated+75% PLGA75:25, 0.6dl/g, ester-terminated
- 100% PLGA75:25, 0.6dl/g, ester-terminated 2.5mg PLGA+3.5mg celecoxib,
Dissolved in 200µl dichloromethane, Stirred in 1200rpm

• 100% PLGA75:25, 0.4dl/g, acid-terminated
■ 75% PLGA75:25, 0.4dl/g, acid-terminated+25% PLGA75:25, 0.6dl/g, ester-terminated
▲ 50% PLGA75:25, 0.4dl/g, acid-terminated+50% PLGA75:25, 0.6dl/g, ester-terminated
▼ 25% PLGA75:25, 0.4dl/g, acid-terminated+75% PLGA75:25, 0.6dl/g, ester-terminated 2.5mg PLGA75:25, 0.6dl/g, ester-terminated+5mg celecoxib
Dissolved in 200µl dichloromethane, Stirred at 1200rpm 2.5mg PLGA75:25, 0.6dl/g, ester-terminated+6mg celecoxib
Dissolved in 200µl dichloromethane, Stirred at 1200rpm 2.5mg PLGA75:25, 0.6ester, 2.5mg+7.5mg celecoxib
Dissolved in different volume dichloromethane

* 7.5mg celecoxib, 200ul DCM, Stirred at 1200rpm
* 7.5mg celecoxib, 300ul DCM, Stirred at 1000rpm 2.5mg PLGA75:25, 0.6dl/g, ester-terminated+5mg celecoxib
Dissolved in 200µl dichloromethane, Different stirring rate ● Stirred at 1200rpm
■ Stirred at 1000rpm 2.5mg PLGA75:25, 0.6dl/g, ester-terminated+5mg celecoxib
Dissolved in 200µl dichloromethane, Stirred at 1000rpm in PVA with OD230=0.05

2.5mg PLGA75:25, 0.6dl/g, ester-terminated+6mg celecoxib
Dissolved in 200µl dichloromethane, Stirred at 1000rpm in PVA with OD230=0.05

2.5mg PLGA+5mg celecoxib
Dissolved in 200μl dichloromethane, Stirred at 1200rpm

● PLGA75:25, 0.6dl/g, ester-terminated
■ PLGA75:25, 0.9dl/g, ester-terminated

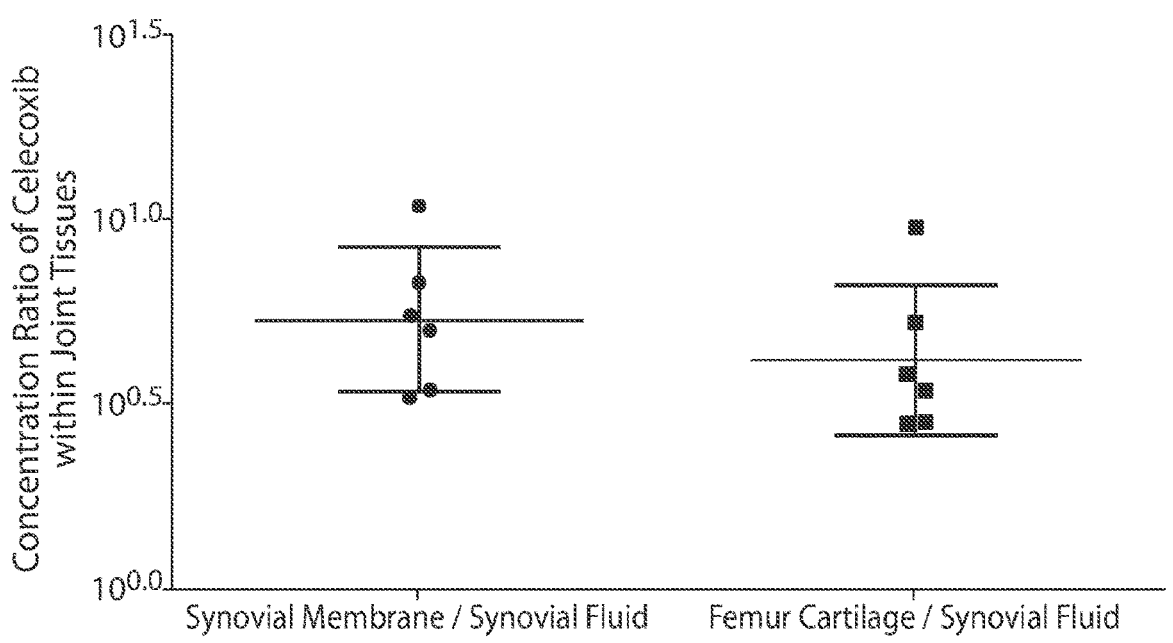
FIGURE 53A
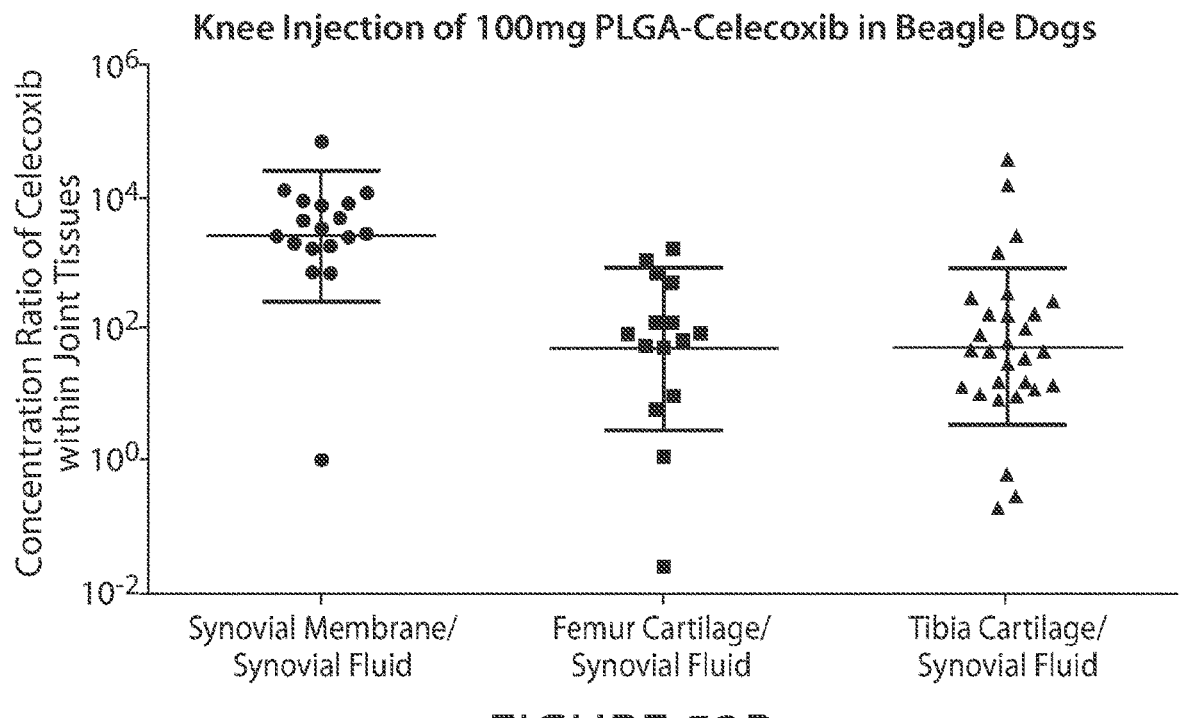
FIGURE 53B

MICROSPHERE-BASED INJECTIBLE CELECOXIB FORMULATION

This application a § 371 national stage entry of PCT Application No. PCT/US2020/045099, filed Aug. 6, 2020, which claims the benefit of U.S. Provisional Application No. 62/884,526, filed Aug. 8, 2019, the contents of which are incorporated herein by reference.

Throughout this application, various publications are cited. The disclosure of these publications is hereby incorporated by reference into this application to describe more fully the state of the art to which this invention pertains.

FIELD OF THE INVENTION

The present invention relates to methods for treating joint-related disorders via localized injection of celecoxib-containing biodegradable microspheres.

BACKGROUND OF THE INVENTION

NSAIDs and Celecoxib

Non-steroidal anti-inflammatory drugs (NSAIDs) treat inflammation and pain. For treating joint diseases, oral NSAIDs have been widely used to decrease pain and improve physical function. However, the vast majority of NSAIDs cause severe side effects due to the inhibition of COX-1 and COX-2 targets. Indeed, each such side effect-causing drug carries a black-box warning on its product label, as required by the FDA. These labels also state that patients should use the lowest effective dosage for the shortest duration. In addition to the cardiovascular and gastrointestinal adverse effects listed in the black-box warnings, the labels also warn of other systemic toxicities such as hepatotoxicity and renal toxicity.

There are two types of NSAIDs. Non-selective COX-1/2 inhibitors, such as ibuprofen and naproxen, inhibit joint cartilage production due to the COX-1 mechanism. Although these NSAIDs are used to treat arthritic pain, they may actually promote the progression of the underlying cartilage degeneration in osteoarthritis. Selective COX-2 inhibitors, such as celecoxib (sold as Celebrex® (Pfizer)), do not inhibit cartilage production and cause fewer gastrointestinal adverse effects than non-selective COX-1/2 inhibitors, but their cardiovascular side effects are still significant.

Celecoxib Formulations

G. Gaudriault, et al. (International Publication No. WO/2017/085561, "A method for morselizing and/or targeting pharmaceutically active principles to synovial tissue") describes a hydrogel formulation of celecoxib that maintained a therapeutic level in the sheep knee for 14 days. The hydrogel is based on poly D,L-lactide and polyethylene glycol (PEG).

M. Homar, et al. ("Influence of polymers on the bioavailability of microencapsulated celecoxib", *J. of Microencapsulation*, November 2007; 24(7): 621-633) describes a list of formulations using PLGA, poly-caprolactone, ethylcellulose, and others. Celecoxib release was observed for seven days. The PLGA microspheres had mean diameters between 10-20 µm. Particles with diameters under 10 µm are subject to phagocytosis and removal by macrophages. Furthermore, the phagocytosed particles cause inflammation (T. Green, et al. ("Polyethylene particles of a 'critical size' are necessary for the induction of cytokines by macrophages in vitro", *Biomaterials*, December 1998; 19(24): 2297-2302; H. Chikaura, et al. ("Effect of particle size on biological response by human monocyte-derived macrophages", *Bio-*

*surface and Biotribology*, March 2016. 2(1):18-25); J. Matthews, et al. ("Comparison of the response of primary human peripheral blood mononuclear phagocytes from different donors to challenge with model polyethylene particles of known size and dose", *Biomaterials*. October 2000. 21(20):2033-2044)). With mean diameters of from 10 µm to 20 µm, a significant portion of the described PLGA microspheres would be subject to macrophage phagocytosis and removal from the injected site, leading to inflammation, and thus rendering the formulations unsuitable as pharmaceutical depots. Furthermore, some formulations stopped releasing drug after an initial phase of burst release.

H. Y. Yang, et al. ("Applicability of a newly developed bioassay for determining bioactivity of anti-inflammatory compounds in release studies—celecoxib and triamcinolone acetonide released from novel PLGA-based microspheres", *Pharm. Res*. (2015) 32:680-690) describes PLGA-polythioester formulations that achieve continuous release of celecoxib for over 90 days. However, polythioester has never been used in any FDA-approved pharmaceuticals.

H. Thakkar, et al. ("Enhanced retention of celecoxib-loaded solid lipid nanoparticles after intra-articular administration", *Drugs R D* 2007; 8(5):275-285) describes solid lipid nanoparticle formulations that released celecoxib for up to 180 hours.

A. Petit, et al. ("Release behavior and intra-articular biocompatibility of celecoxib-loaded acetyl-capped PCLA-PEG-PCLA thermogels", *Biomaterials* 35 (2014) 7919-7928); and A. Petit, et al. ("Sustained intra-articular release of celecoxib from in situ forming gels made of acetyl-capped PCLA-PEG-PCLA triblock copolymers in horses", *Biomaterials* 35 (2015): 426-436), describe hydrogel formulations that released therapeutic concentrations of celecoxib (100 ng/ml) for two weeks after subcutaneous injection in rats. Also described are hydrogel formulations that released therapeutic concentrations of celecoxib for four weeks after intra-articular injection in horses. However, PCLA (poly-caprolactone-co-lactide) has never been used in any FDA-approved pharmaceuticals.

M. Janssen, et al. ("Celecoxib-loaded PEA microspheres as an auto regulatory drug-delivery system after intra-articular injection", *J. Control Release,* 2016 Dec. 28:244 (Pt. A): 30-40) describes polyester amide (PEA) formulations that released celecoxib for 80 days and beyond. However, polyester amide has never been used in any FDA-approved pharmaceuticals.

H. Thakkar, et al. ("Celecoxib incorporated chitosan microspheres: in vitro and in vivo evaluation", *J. of Drug Targeting*, October-December 2004, Vol. 12 (9-10), pp. 549-557) describes chitosan formulations that released celecoxib for 100 hours. Chitosan has never been used in any FDA-approved pharmaceuticals.

PLGA Microspheres

Biodegradable microspheres made of polylactic co-glycolic acid copolymer (PLGA) are known. PLGA is made of polylactic acid (PLA), polyglycolic acid (PGA), and typically both. PLGA is an FDA-approved biodegradable polymer. It has been extensively investigated in many medical and pharmaceutical fields due to its good biodegradability and biocompatibility. PLGA-containing microspheres have shown sustained release characteristics due to degradation and diffusion mechanisms. The drug release profile of a PLGA microsphere preparation is dependent on certain factors, such as the specific properties of the drug, the ratio of PLA to PGA, the type of end cap of the polymer (i.e., ester or acid), the molecular weight/inherent viscosity of the polymer, the loading ratio of drug to the polymer, and the size of the microspheres.

In 2017, Zilretta®, a PLGA-triamcinolone-acetonide microsphere formulation for knee injection, was approved by the FDA. Zilretta® exhibits pain reduction in knee osteoarthritis patients for 12 weeks. Meanwhile, U.S. Pat. No. 9,555,048, assigned to Flexion and relating to Zilretta®, describes tests of various combinations of PLGA, drug, and other co-polymers, and their effects on the release of triam-cinolone acetonide. The longest drug release duration of any formulation described in this patent is 40-50 days.

An Unmet Need

There is an unmet need for a superior way to treat joint disorders using celecoxib, while minimizing the drug's side effects observed with systemic delivery.

SUMMARY OF THE INVENTION

This invention provides a biodegradable microsphere, wherein the microsphere (i) has a diameter of from 1 μm to 500 μm; (ii) comprises a polylactic-co-glycolic acid copolymer (PLGA) matrix; (iii) carries pharmaceutical cele-coxib; and (iv) when present in a suitable joint-related tissue, releases celecoxib for at least one month.

This invention also provides a plurality of biodegradable microspheres, wherein the microspheres (i) have a $d_{90}$ value from 1 μm to 500 μm; (ii) comprise a polylactic-co-glycolic acid copolymer (PLGA) matrix; (iii) carry a therapeutically effective amount of pharmaceutical celecoxib; and (iv) when present in a suitable joint-related tissue, release celecoxib for at least one month.

This invention further provides an injectable formulation comprising (a) a pharmaceutically acceptable carrier and (b) a plurality of biodegradable microspheres wherein the microspheres (i) have a $d_{90}$ value from 1 μm to 500 μm; (ii) comprise a polylactic-co-glycolic acid copolymer (PLGA) matrix; (iii) carry a therapeutically effective amount of pharmaceutical celecoxib; and (iv) when present in a suit-able joint-related tissue, release celecoxib for at least one month.

This invention still further provides a method for treating a joint-related disorder in a subject comprising introducing biodegradable microspheres into suitable tissue in or around one or more of the subject's joints, wherein the microspheres (i) have a $d_{90}$ value from 1 μm to 500 μm; (ii) comprise a polylactic-co-glycolic acid copolymer (PLGA) matrix; (iii) carry a therapeutically effective amount of pharmaceutical celecoxib; and (iv) when present in a suitable joint-related tissue, release celecoxib for at least one month.

Finally, this invention provides a kit comprising, in sepa-rate compartments, (a) a diluent, and (b) plurality of biode-gradable microspheres, wherein the microspheres (i) have a $d_{90}$ value from 1 μm to 500 μm; (ii) comprise a polylactic-co-glycolic acid copolymer (PLGA) matrix; (iii) carry a therapeutically effective amount of pharmaceutical cele-coxib; and (iv) when present in a suitable joint-related tissue, release celecoxib for at least one month.

Figure 1:
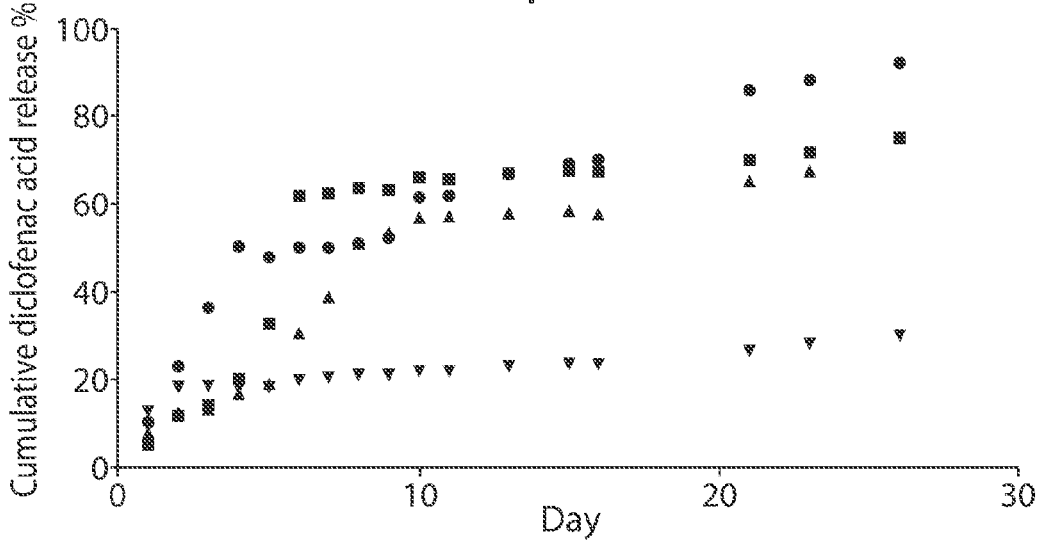
FIG. 1

This figure shows the release of diclofenac acid in a range of PLGA and PDLA microspheres.

FIG. 2

This figure shows the release of diclofenac acid in PLGA50:50, 0.2 dl/g, acid-terminated microspheres.

FIG. 3

This figure shows the diclofenac acid release from a range of PLGA and PDLA formulations.

FIG. 4

This figure shows that both formulations involving PLGA85:15, 0.6 dl/g, ester-terminated, resulted in complete diclofenac acid release within 10 days.

FIG. 5

This figure shows complete diclofenac acid release in 10 days for a range of PLGA formulations.

FIG. 6

This figure shows the microsphere formation of lornoxi-cam-PLGA microspheres (PLGA50:50, 0.2 dl/g, acid-termi-nated).

FIG. 7

This figure shows cumulative celecoxib release for a range of PLGA formulations.

FIG. 8

This figure shows that the celecoxib-loading amount from 1 mg to 2.5 mg, mixed with 2.5 mg PLGA, did not change drug release significantly.

FIG. 9

This figure shows that increasing celecoxib loading to 3-3.5 mg, mixed with 2.5 mg PLGA50:50, 0.5 dl/g, ester-terminated, resulted in continuous celecoxib release, which is different from the little drug release seen in day 9 to day 15 in formulations with lower (1 mg) celecoxib loading.

FIG. 10

In this figure, 2.5 mg of 50% of PLGA50:50, 0.5 dl/g, acid-terminated, and 50% of PDLA, 0.4 dl/g, ester-termi-nated, with 1 mg celecoxib loading, resulted in continuous celecoxib release over 45 days.

FIG. 11

In this figure, 2.5 mg of PLGA with all ratios of PLGA50:50, 0.5 dl/g, acid-terminated, mixed with PLGA50:50, 0.4 dl/g, ester-terminated, and PLGA50:50, 0.5 dl/g, ester-ter-minated, resulted in continuous drug release at celecoxib loading of 1 mg.

FIG. 12

In this figure, 2.5 mg of PLGA with 2.5 mg celecoxib loading was tested. 25% PDLA, 0.4 dl/g, ester-terminated, with 75% PLGA50:50, 0.5 dl/g, acid-terminated, resulted in continuous celecoxib release over 25 days.

FIG. 13

In this figure, 2.5 mg of PLGA with 3.5 mg celecoxib loading was tested. 50-75% of PLGA50:50, 0.5 dl/g, acid-terminated, mixed with PLGA75:25, 0.6 dl/g, ester-termi-nated, resulted in continuous celecoxib release over 25 days.

FIG. 14

This figure shows that PEG1450 blending with PLGA slightly increased celecoxib release. With 0 mg of PEG1450, celecoxib release was minimal from day 11 to day 15, whereas all three formulations with PEG1450 blending showed continuous celecoxib release until day 30.

FIG. 15

This figure shows that celecoxib loading of 1-2.5 mg with 2.5 mg PLGA75:25, 0.4 dl/g, acid-terminated, dissolved in 100 μl dichloromethane and stirred at 1,000 rpm, resulted in continuous drug release over 30 days.

FIG. 16

This figure shows that celecoxib loading of 1-3.5 mg with 2.5 mg PLGA75:25, 0.4 dl/g, acid-terminated, dissolved in 200 μl dichloromethane (DCM) and stirred at 1,000 rpm, resulted in continuous drug release over 30 days.

FIG. 17

This figure shows that celecoxib loading of 3.5 mg and 5 mg with 2.5 mg PLGA75:25, 0.4 dl/g, acid-terminated, dissolved in 200 μl dichloromethane and stirred at 1,000 rpm, resulted in continuous drug release over 60 days.

FIG. 18

This figure shows that celecoxib loading of 5 mg and 2.5 mg PLGA75:25, 0.4 dl/g, acid-terminated, dissolved in 200 μl dichloromethane and stirred at 1,200 rpm, resulted in continuous drug release over 60 days.

FIG. 19

This figure shows that celecoxib loading of 3.5 mg and 5 mg, and 2.5 mg PLGA75:25, 0.4 dl/g, acid-terminated, dissolved in 200 μl dichloromethane and stirred at 1,200 rpm, resulted in continuous drug release over 60 days.

FIG. 20

This figure shows that celecoxib loading at 4 mg, 5 mg, and 6 mg, mixed with PLGA50:50, 0.5 dl/g, ester-terminated, and PLGA50:50, 0.6 dl/g, ester-terminated, dissolved in 200 μl dichloromethane and stirred at 1,000 rpm, resulted in continuous celecoxib release over 30 days.

FIG. 21

This figure shows that celecoxib loading at 6 mg and 7.5 mg, mixed with PLGA50:50, 0.5 dl/g, ester-terminated, dissolved in 200 μl dichloromethane and stirred at 1,000 rpm, resulted in continuous celecoxib release over 20 days.

FIG. 22

This figure shows that celecoxib loading at 4 mg, 5 mg, and 6 mg, mixed with PLGA50:50, 0.7 dl/g, ester-terminated, dissolved in 200 μl dichloromethane and stirred at 1,000 rpm, resulted in continuous celecoxib release over 70 days. Unexpectedly, increased loading ratio did not result in higher release rate.

FIG. 23

This figure shows that celecoxib loading at 4 mg, 5 mg, and 6 mg, mixed with 2.5 mg PLGA75:25, 0.6 dl/g, ester-terminated, dissolved in 200 μl dichloromethane and stirred at 1,000 rpm, resulted in continuous celecoxib release over 111 days. Higher celecoxib loading was associated with faster drug release.

FIG. 24

This figure shows that celecoxib loading at 5 mg, 6 mg, and 7.5 mg, mixed with 2.5 mg PLGA75:25, 0.6 dl/g, ester-terminated, dissolved in 300 μl dichloromethane and stirred at 1,000 rpm, resulted in continuous celecoxib release over 92 days. Higher celecoxib loading was associated with faster drug release.

FIG. 25

This figure shows that celecoxib loading at 5 mg and 6 mg, mixed with 2.5 mg PLGA75:25, 0.6 dl/g, ester-terminated, dissolved in 300 μl or 400 μl and stirred at 1,000 rpm, resulted in continuous celecoxib release over 90 days.

FIG. 26

This figure shows celecoxib loading of 5 mg and 6 mg, mixed with 2.5 mg PLGA75:25, 0.9 dl/g, ester-terminated, dissolved in 300 μl dichloromethane and stirred at 1,000 rpm, resulted in continuous celecoxib release over 90 days.

FIG. 27

This figure shows that celecoxib loading of 5 mg, 6 mg, and 7.5 mg, mixed with PLGA75:25, 0.9 dl/g, ester-terminated, dissolved in 300 μl or 400 μl dichloromethane and stirred at 1,000 rpm, resulted in continuous celecoxib release over 80 days.

FIG. 28

This figure shows that celecoxib loading of 5 mg, 6 mg, and 7.5 mg, mixed with PLGA75:25, 0.9 dl/g, ester-terminated, dissolved in 300 μl or 400 μl dichloromethane and stirred at 1,000 rpm, resulted in continuous celecoxib release over 80 days.

FIG. 29

This figure shows that celecoxib loading of 5 mg and 7.5 mg, mixed with PLGA75:25, 0.9 dl/g, ester-terminated, dissolved in 300 μl dichloromethane and stirred at 1,000 rpm, resulted in continuous celecoxib release over 100 days and 50 days, respectively.

FIG. 30

This figure shows that celecoxib loading of 5 mg and 6 mg, mixed with PLGA75:25, 0.9 dl/g, ester-terminated, dissolved in 300 μl dichloromethane and stirred at 1,000 rpm, resulted in continuous celecoxib release over 70 days.

FIG. 31

This figure shows that celecoxib loading of 5 mg and 6 mg, mixed with PLGA75:25, 1.2 dl/g, ester-terminated, dissolved in 300 μl dichloromethane and stirred at 1,000 rpm, resulted in continuous celecoxib release over 70 days.

FIG. 32

This figure shows that 7.5 mg of celecoxib, mixed with 2.5 mg PLGA85:15, 0.6 dl/g, ester-terminated, dissolved in 300 μl dichloromethane and stirred at 1,000 rpm, resulted in continuous celecoxib release over 40 days.

FIG. 33

This figure shows that 6 mg of celecoxib, mixed with 2.5 mg PLGA85:15, 0.6 dl/g, ester-terminated, dissolved in 300 μl dichloromethane and stirred at 1,000 rpm, resulted in continuous celecoxib release over approximately 30 days.

FIG. 34

This figure shows that celecoxib loading of 7.5 mg, mixed with 2.5 mg PLGA85:15, 1.5 dl/g, ester-terminated, dissolved in 300 μl and 400 μl dichloromethane and stirred at 1,000 rpm, resulted in continuous celecoxib release over 35 days.

FIG. 35

This figure shows that celecoxib loading of 7.5 mg, mixed with 2.5 mg PLGA85:15, 1.5 dl/g, ester-terminated, dissolved in 500 μl dichloromethane and stirred at 1,000 rpm, resulted in continuous celecoxib release over 50 days.

FIG. 36

This figure shows that celecoxib loading of 5 mg and 6 mg, mixed with 2.5 mg PDLA, 0.6 dl/g, ester-terminated, dissolved in 300 μl dichloromethane and stirred at 1,000 rpm, resulted in continuous celecoxib release over 40 days.

FIG. 37

This figure shows that celecoxib loading of 5 mg and 6 mg, mixed with 2.5 mg PDLA, 0.6 dl/g, ester-terminated, dissolved in 300 μl and 400 μl dichloromethane and stirred at 1,000 rpm, resulted in continuous celecoxib release over 35 days.

FIG. 38

This figure shows that celecoxib loading of 5 mg and 6 mg, mixed with 2.5 mg PDLA, 0.4 dl/g, ester-terminated, dissolved in 200 μl dichloromethane and stirred at 1,000 rpm, resulted in little celecoxib release from day 20 to day 30 and from day 50 to day 60, which is unsuitable for continuous celecoxib release over multiple months.

FIG. 39

This figure shows that mixing PLGA50:50, 0.7 dl/g, ester-terminated, with PLGA75:25, 0.6 dl/g, ester-terminated, slowed down celecoxib release and prolonged duration of continuous drug release.

FIG. 40

This figure shows that mixing PLGA50:50, 0.7 dl/g, ester-terminated, with PLGA75:25, 0.6 dl/g, ester-terminated, slowed down celecoxib release. All formulations resulted in continuous drug release for at least 60 days.

FIG. 41

This figure shows that mixing PLGA75:25, 0.4 dl/g, acid-terminated, with PLGA75:25, 0.6 dl/g, ester-terminated, slowed down celecoxib release. All formulations resulted in continuous drug release for at least 60 days.

FIGS. 42A-42D

The first two figures show that 2.5 mg PLGA75:25, 0.6 dl/g, ester-terminated, and 5 mg celecoxib (FIG. 42A) or 6 mg celecoxib (FIG. 42B), dissolved in 200 μl dichloromethane and stirred at 1,200 rpm in PVA (with optical density 230 nm (OD230) at 0.160), resulted in continuous drug release over 180 days. FIGS. 42C (top) and 42D (bottom) show microscopic images of microspheres formed by 2.5 mg PLGA75:25, 0.6 dl/g, ester-terminated and 5 mg (FIG. 42C) or 6 mg (FIG. 42D) celecoxib, dissolved in 200 μl dichloromethane and stirred at 1,200 rpm in 50 ml PVA (OD230=0.160) for 2 minutes, followed by stirring at 500 rpm for 2 hours, harvesting, washing with water, and lyophilization.

FIG. 43

This figure shows that 2.5 mg PLGA75:25, 0.6 dl/g, ester-terminated, and 6 mg celecoxib, dissolved in 300 μl dichloromethane and stirred at 1,000 rpm in PVA (OD230=0.160), resulted in continuous drug release over 175 days.

FIG. 44

This figure shows that 2.5 mg PLGA75:25, 0.6 dl/g, ester-terminated, and 7.5 mg celecoxib, dissolved in 200 or 300 μl dichloromethane and stirred at 1,000 or 1,200 rpm in PVA (OD230=0.160), resulted in continuous drug release over 180 days.

FIG. 45

This figure shows that 2.5 mg PLGA75:25, 0.6 dl/g, ester-terminated, and 5 mg celecoxib, dissolved in 200 μl dichloromethane and stirred at 1,000 rpm or 1,200 rpm in PVA (OD230=0.160), resulted in continuous drug release over 180 days.

Figure 46A:
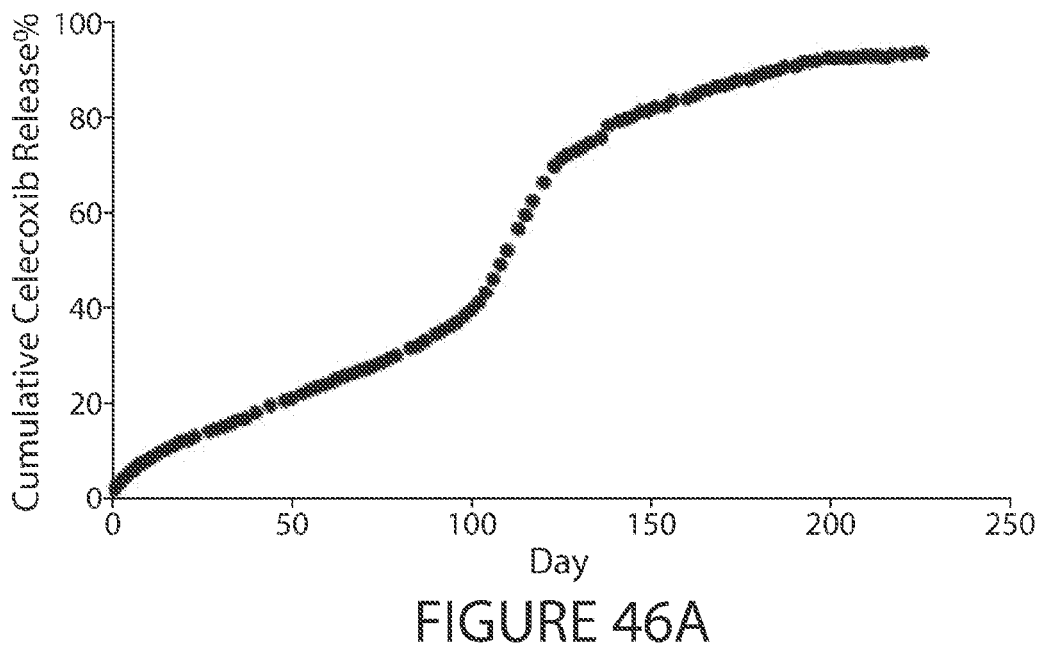
Figure 46B:
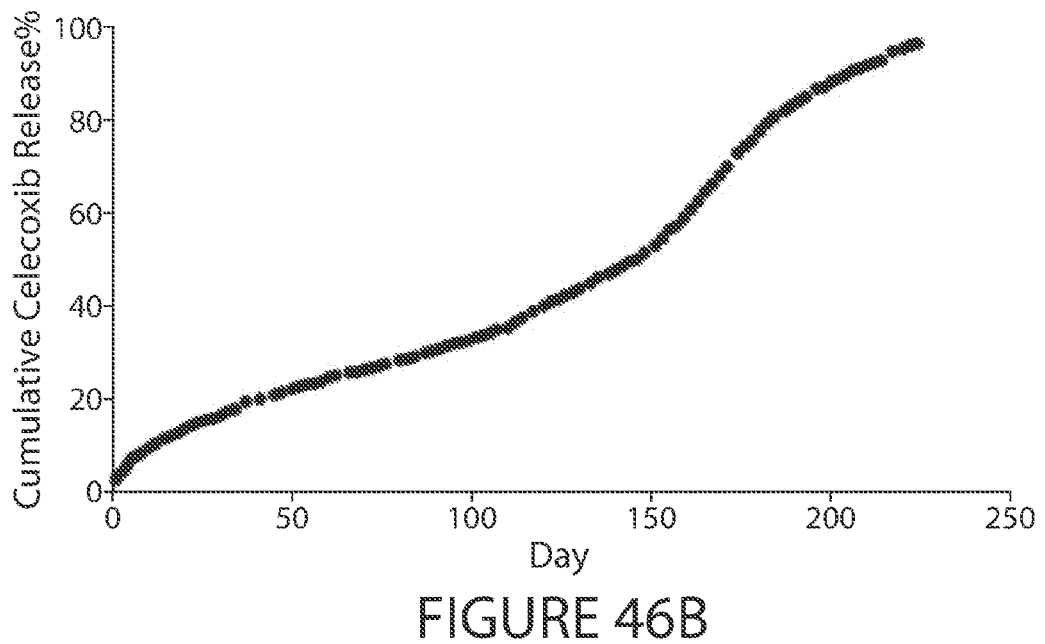

FIGS. 46A and 46B

These figures show 2.5 mg PLGA75:25, 0.6 dl/g, ester-terminated, and 5 mg celecoxib (FIG. 46A) or 6 mg celecoxib (FIG. 46B), dissolved in 200 μl dichloromethane and stirred at 1,000 rpm in PVA (OD230=0.05), resulted in continuous drug release over 180 days.

Figure 47A:
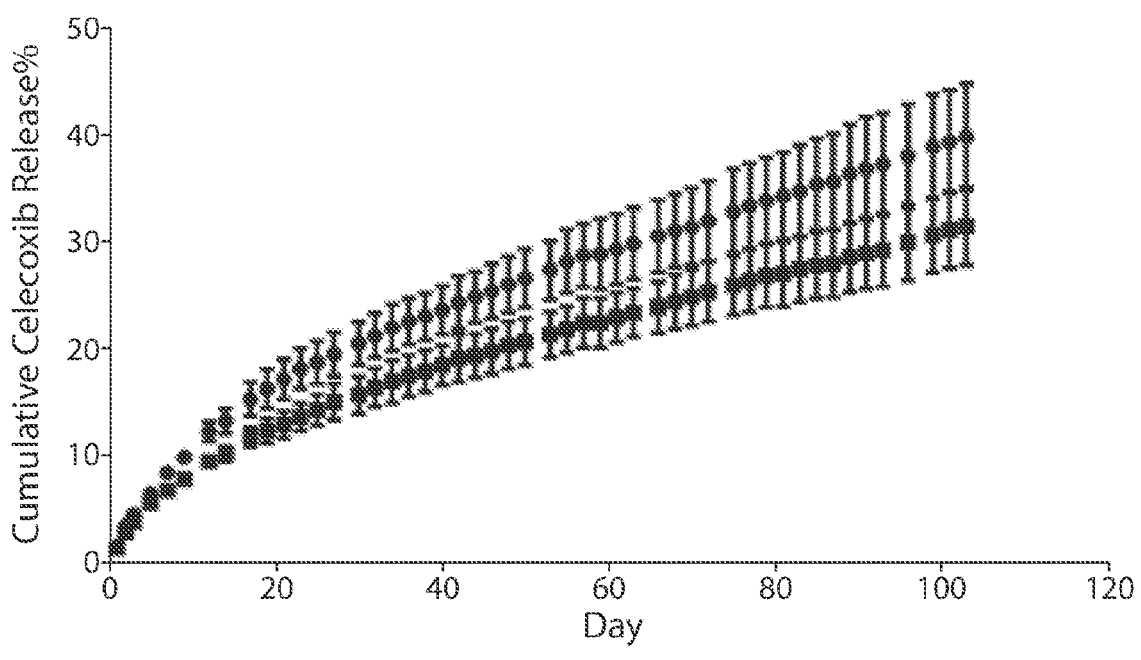
Figure 47B:
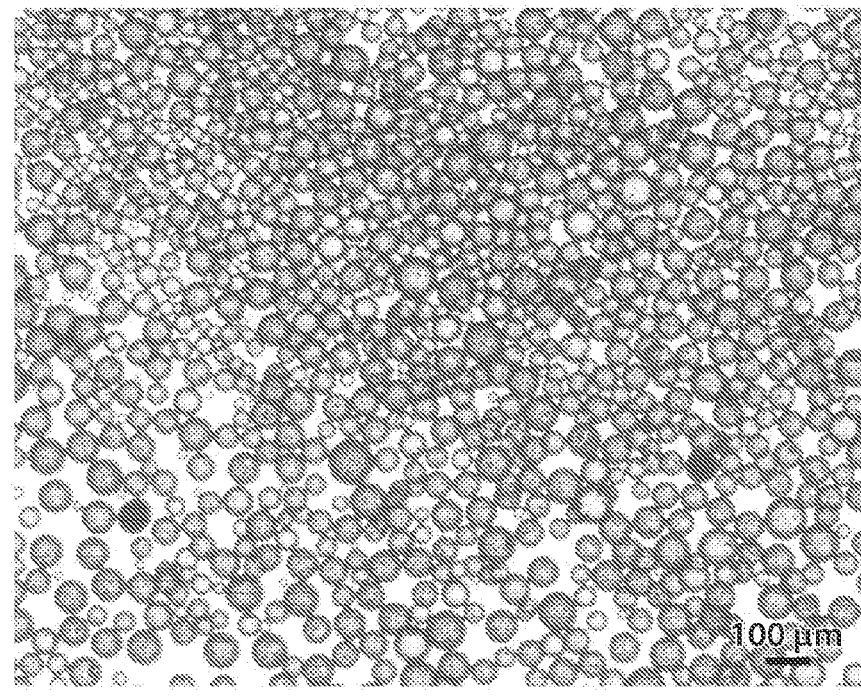

FIGS. 47A and 47B

FIG. 47A shows 2.5 mg PLGA75:25, 0.6 dl/g or 0.9 dl/g, ester-terminated, and 5 mg celecoxib, dissolved in 200 μl dichloromethane and stirred at 1,200 rpm in PVA (OD230=0.160), resulted in continuous drug release over at least 100 days. FIG. 47B shows a microscopic image of microspheres formed by 2.5 mg PLGA75:25, 0.9 dl/g, ester-terminated and 5 mg celecoxib, dissolved in 200 μl dichloromethane and stirred at 1,200 rpm for 2 minutes in 50 ml PVA (OD230=0.160), followed by stirring at 500 rpm for 2 hours, harvesting, washing with water, and lyophilization.

FIG. 48

This figure shows plasma celecoxib concentration after injection of 5 mg of the present formulation into bilateral knees of Lewis rats.

FIGS. 49A-49C

Figure 49A:
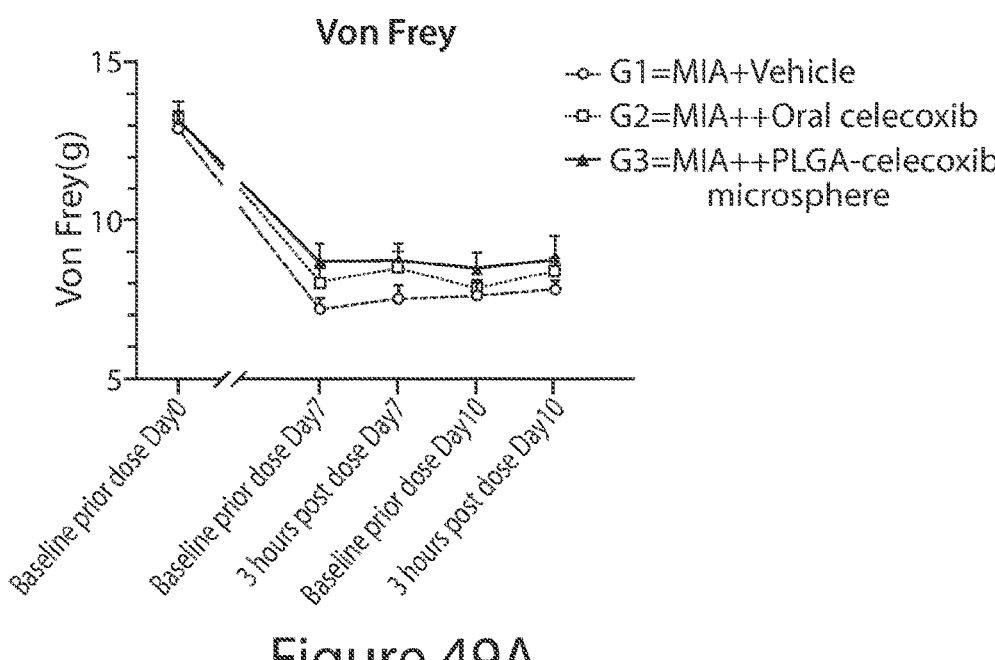
Figures 49B, 49C:
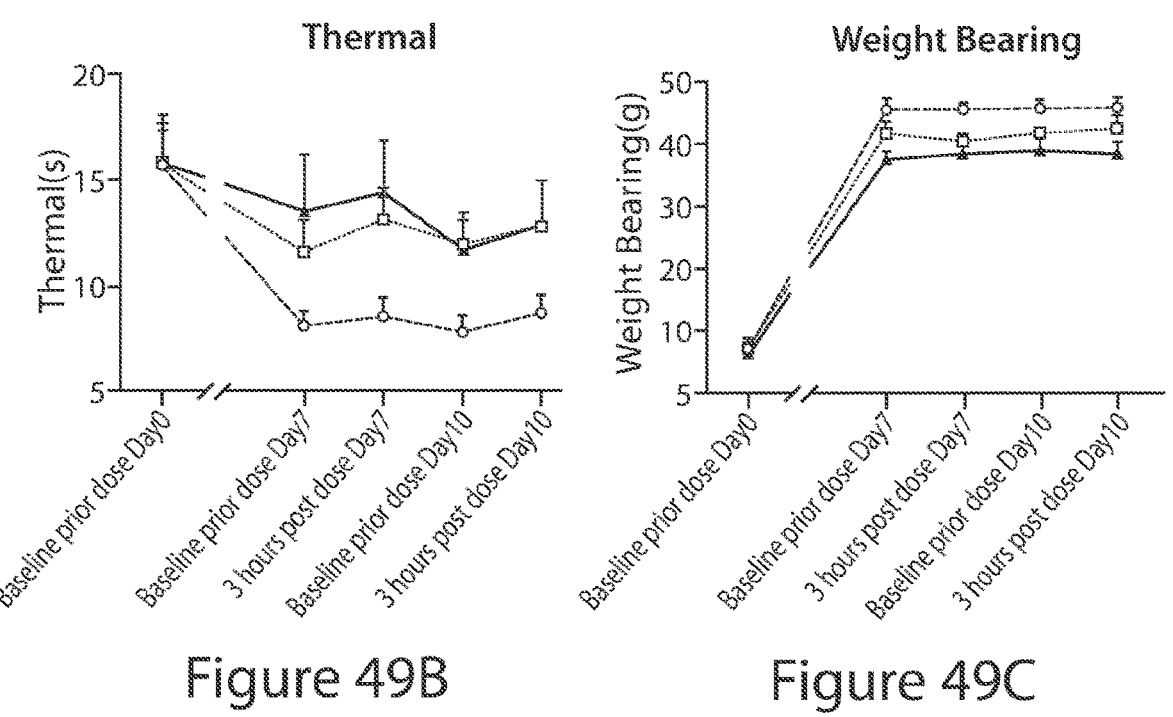

These figures show results from using the present formulation in a rat monoiodoacetate (MIA) osteoarthritis pain model. Specifically, the data shown include results from a Von Frey filament test (FIG. 49A), a thermal hyperalgesia test (FIG. 49B), and a test for differential weight bearing on hind limbs (FIG. 49C).

FIGS. 50A-50D

Figures 50A, 50B:
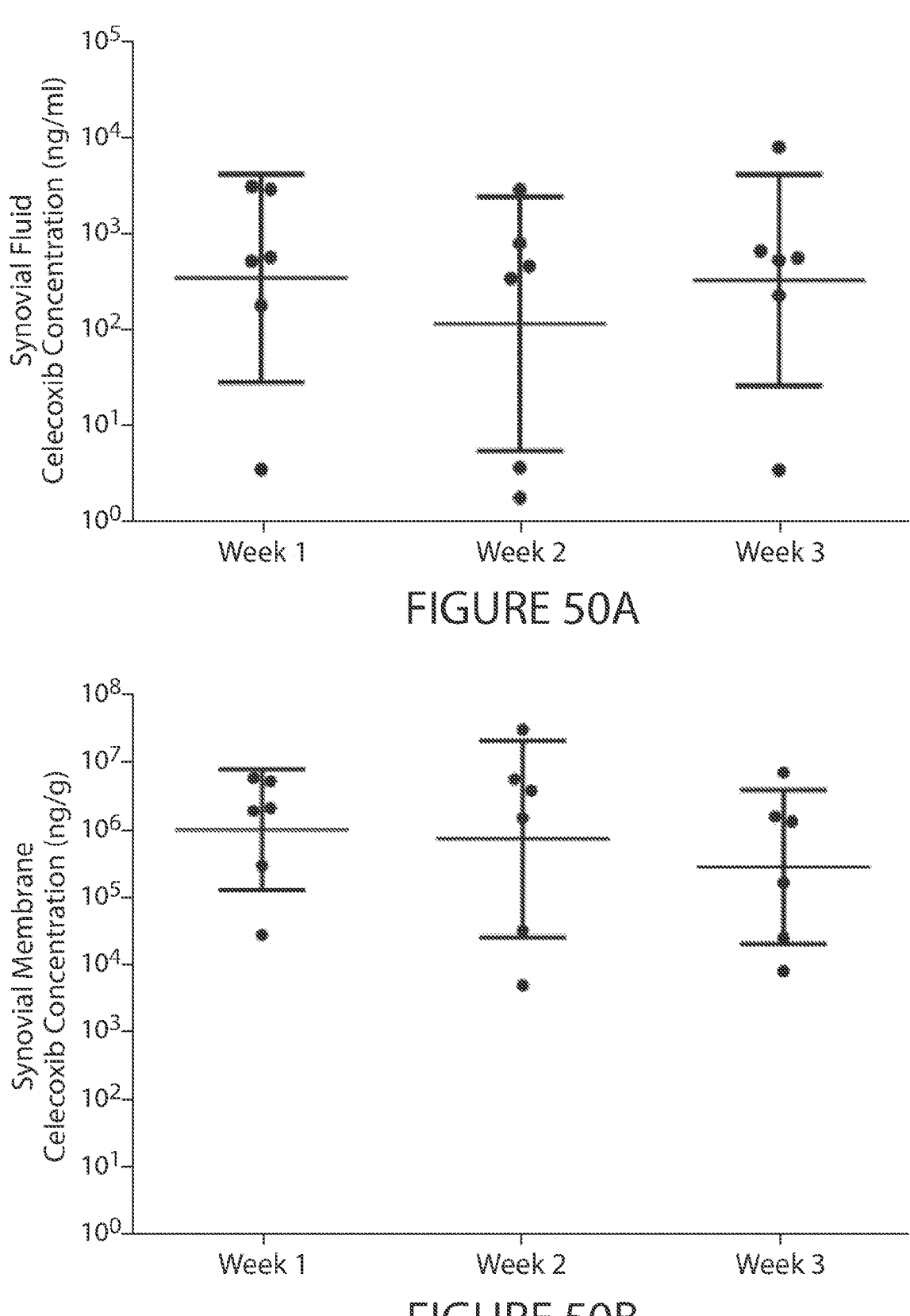
Figures 50C, 50D:
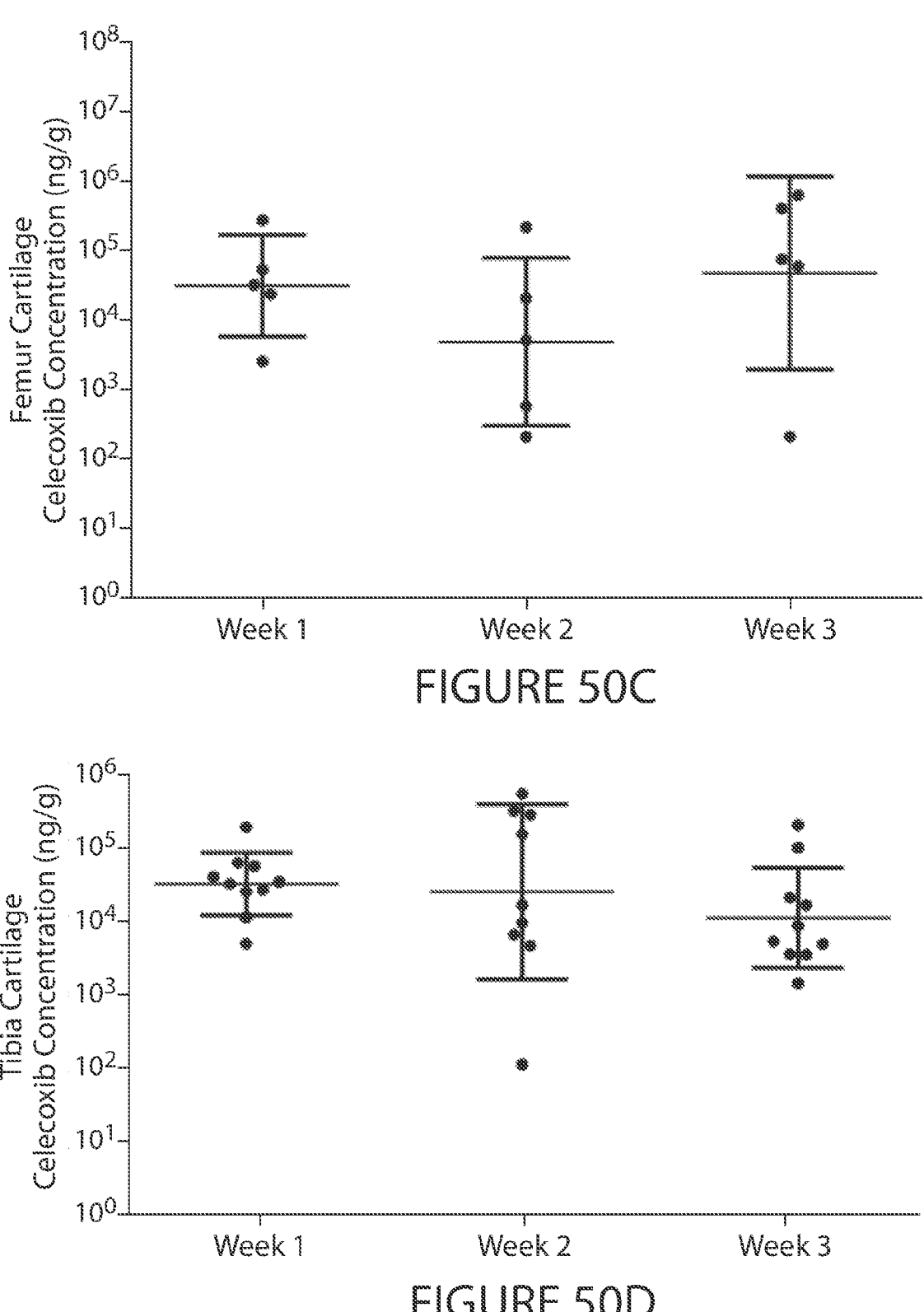

These figures show celecoxib concentration in joint tissues (i.e., synovial fluid (FIG. 50A), synovial membrane (FIG. 50B), femur cartilage (FIG. 50C), and tibia cartilage (FIG. 50D)) after injection of 100 mg PLGA-encapsulated celecoxib formulation into bilateral knees of Beagle dogs.

FIG. 51

This figure shows celecoxib plasma concentration after injection of 100 mg PLGA-encapsulated celecoxib formulation into bilateral knees of Beagle dogs.

FIG. 52

This figure compares celecoxib concentrations in plasma and joint tissues after oral daily 5 mg/kg dosing of celecoxib in Beagle dogs.

FIGS. 53A and 53B

FIG. 53A shows the concentration ratios of celecoxib within joint tissues (i.e., (i) synovial membrane to synovial fluid, and (ii) femur cartilage to synovial fluid) after oral daily 5 mg/kg dosing of celecoxib in Beagle dogs. FIG. 53B shows the concentration ratios of celecoxib within joint tissues (i.e., (i) synovial membrane to synovial fluid, (ii) femur cartilage to synovial fluid, and (iii) tibia cartilage to synovial fluid) after knee injection of 100 mg PLGA-celecoxib oral in Beagle dogs.

DETAILED DESCRIPTION OF THE INVENTION

This invention provides celecoxib-containing biodegradable microspheres and methods for using them to treat joint-related disorders.

Definitions

In this application, certain terms are used which shall have the meanings set forth as follows.

As used herein, a "biodegradable microsphere" comprises a polylactic-co-glycolic acid copolymer (PLGA) matrix, which matrix can include solely polylactic acid (PLA), solely polyglycolic acid (PGA), or a polymeric combination of lactic acid and glycolic acid units. For certain lactic acid to glycolic acid ratios (e.g., 50:50 to 100:0), the higher a microsphere's lactic acid content, the slower it degrades and, thus, the more stable it is. Conversely, for such ratios, the higher a microsphere's glycolic acid content, the faster it degrades and the less stable it is. In one embodiment, the biodegradable microsphere contains a combination of lactic acid and glycolic acid units wherein the molar ratio of lactic acid to glycolic acid units (i.e., the "lactic acid to glycolic acid ratio", or "L:G ratio") is 0:100, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or 100:0. In another embodiment, the biodegradable microsphere contains a combination of lactic acid and glycolic acid units wherein the molar ratio of lactic acid to glycolic acid is from 5:95 to 20:80, from 20:80 to 40:60, from 40:60 to 50:50, from 50:50 to 60:40, from 60:40 to 80:20, from 80:20 to 100:0, from 50:50 to 100:0, from 60:40 to 90:10, from 70:30 to 80:20, from 50:50 to 80:20, from 50:50 to 90:10, from 60:40 to 70:30, from 80:20 to 90:10, or from 90:10 to 100:00. The population of biodegradable microspheres used in this invention can be homogeneous or heterogeneous with respect to the microspheres' molar ratio of lactic acid to glycolic acid. In one embodiment, the population of biodegradable microspheres is homogeneous with respect to the microspheres' molar ratio of lactic acid to glycolic acid (e.g., the population includes only microspheres wherein the molar ratio of lactic acid to glycolic acid is 75:25). In another embodiment, the population of biodegradable microspheres is heterogeneous (e.g., the population includes both (i) microspheres wherein the molar ratio of lactic acid to glycolic acid is 70:30, and (ii) microspheres wherein the molar ratio of lactic acid to glycolic acid is 80:20). In a preferred embodiment, the instant microspheres contain PLGA having an inherent viscosity of 0.1 to 2.4 dl/g (e.g., 0.16 to 1.7 dl/g), and a molecular weight from 1,000 to 600,000 (e.g., from 7,000 to 240,000).

The subject biodegradable microsphere (i) has a diameter from 1 μm to 500 μm, (ii) can non-covalently carry a therapeutic agent (e.g., celecoxib), and (iii) depending on its polymeric composition, degrades over a period lasting, for example, from one month to over six months when placed in suitable joint-related tissue. Microsphere diameters (and $d_{90}$ values) include, for example, the following: (i) from 1 μm to 20 μm, from 20 μm to 40 μm, from 40 μm to 60 μm, from 60 μm to 80 μm, from 80 μm to 100 μm, from 100 μm to 120 μm, from 120 μm to 140 μm, from 140 μm to 160 μm, from 160 μm to 180 μm, from 180 μm to 200 μm, from 200 μm to 250 μm, from 250 μm to 300 μm, from 300 μm to 350 μm, from 350 μm to 400 μm, from 400 μm to 450 μm, or from 450 μm to 500 μm; (ii) 20 μm, 40 μm, 60 μm, 80 μm, 100 μm, 120 μm, 140 μm, 160 μm, 180 μm, 200 μm, 250 μm, 300 μm, 350 μm, 400 μm, 450 μm, or 500 μm; and (iii) from 20 μm to 100 μm, from 20 μm to 150 μm, from 50 μm to 100 μm, or from 50 μm to 150 μm. The subject biodegradable microspheres can further comprise polyethylene glycol (PEG). Biodegradable PLGA microspheres (including homogeneous and heterogeneous populations thereof having defined molar ratios of lactic acid to glycolic acid units) are commercially available from, among other sources, Millipore-Sigma in the form of Degradex® products (Burlington, MA) and Evonik Industries in the form of Resomer® products (Essen, Germany).

As used herein, the term "carry", with respect to pharmaceutical celecoxib and a biodegradable microsphere, means that the pharmaceutical celecoxib is non-covalently bound to, or otherwise contained in or on, the biodegradable microsphere in a manner permitting release from the microsphere during its biodegradation.

As used herein, the term "celecoxib" shall mean 4-[5-(4-methylphenyl)-3-(trifluoromethyl)-1H-pyrazol-1-yl] benzenesulfonamide, with CAS number 169590-42-5. Celecoxib is a nonsteroidal anti-inflammatory drug. It is commercially available, and is sold by Pfizer under the trade name Celebrex®.

As used herein, the term "diluent" includes, without limitation, carboxymethylcellulose sodium, polysorbate 80, mannitol (which can optionally be incorporated on and/or into the microspheres to improve suspendability), and water.

As used herein, the term "$d_{90}$ value", with respect to a population of biodegradable microspheres having a specified size range, means that 90% of the biodegradable microspheres have a diameter in the specified range.

As used herein, "introducing", with respect to biodegradable microspheres, means delivering to a specified part of the body, such as joint fluid. Methods of introducing biodegradable microspheres to joint fluid are known and include, for example, intra-articular injection. See, e.g., the Zilretta® label. Methods for injecting biodegradable microspheres into discs are known and can be performed based on known animal studies. For example, polyester amide microspheres were injected to the intervertebral discs in a canine model of disc degeneration, and were shown to have good cytocompatability and biocompatibility. In a rat discitis model, intra-discal vancomycin-loaded PLGA microspheres were shown to control and reduce infective discitis, with superior efficacy to intravenous vancomycin. See, e.g., Williems, et al., and Wang, et al.

As used herein, a "joint-related disorder" includes, without limitation, osteoarthritis, synovitis, hemophilic arthropathy, rheumatoid arthritis, psoriatic arthritis, juvenile rheumatoid arthritis, gouty arthritis, septic or infectious arthritis, reactive arthritis, reflex sympathetic dystrophy, scleroderma, ankylosing spondylitis, algodystrophy, achondroplasia, Paget's disease, Tietze syndrome or costal chondritis, fibromyalgia, neurogenic or neuropathic arthritis, arthropathy, sarcoidosis, amylosis, cartilage injury, hydarthrosis, periodical disease, rheumatoid spondylitis, osteochondritis dissecans, hypertropic arthritis, *Yersinia* arthritis, pyrophosphate arthritis, an endemic form of arthritis, fibromyalgia, systemic lupus erythematosus, scleroderma, ankylosing spondylitis, degenerative disc disease, chronic lower back pain, chronic neck pain, hip dysplasia, osteochondrosis, elbow dysplasia, joint injury caused by trauma, acute and subacute bursitis, acute and subacute nonspecific tenosynovitis and epicondylitis, acute rheumatic carditis and ankylosing spondylitis, tenosynovitis, epicondylitis, synovitis, sciatica, and other forms of radicular pain. In one embodiment, a joint-related disorder includes discomfort, inflammation, or other indication associated with recovery from a surgical joint procedure such as a total or partial knee replacement, a total or partial hip replacement, a total or partial ankle replacement, an arthroscopic or open joint surgery, a microfracture, an autologous chondrocyte implantation, mosaicplasty, debridement and lavage, a ligament repair, a tendon repair, a rotator cuff repair, meniscus surgery, or synovectomy.

As used herein, the term "pharmaceutical celecoxib" includes, without limitation, celecoxib and pharmaceutical salts (e.g., celecoxib sodium) and esters thereof.

"Pharmaceutically acceptable carriers" are well known and include, without limitation, the diluents described herein.

As used herein, a biodegradable microsphere "releases" celecoxib when some or all of the celecoxib contained by the microsphere is freed into the microsphere's surrounding milieu. Preferably, the release is continuous. For example, in a plurality of celecoxib-carrying biodegradable microspheres having an average release per day of X mg, the celecoxib released per day is, e.g., from 0.1X mg to 10X mg, from 0.2X mg to 5X mg, or from 0.5X mg to 2X mg. In another example, in a plurality of celecoxib-carrying biodegradable microspheres having an average release per week of X mg, the celecoxib released per week is, e.g., from 0.2X mg to 10X mg, or from 0.5X mg to 2X mg. Celecoxib release into the joint-related tissue can precede, and is distinct from, its efficacy in that tissue. For example, biodegradable microspheres that release a therapeutically effective amount of pharmaceutical celecoxib into a joint's synovial fluid for two months might yield a therapeutic effect for three months.

As used herein, the term "subject" includes, without limitation, a mammal such as a human, a non-human primate, a dog, a cat, a horse, a sheep, a goat, a cow, a rabbit, a pig, a rat and a mouse. Preferably, the subject is human. In another preferred embodiment, the subject is a cat, a dog, or a horse.

As used herein, the phrase "suitable joint-related tissue" includes any portion of a joint, the joint's surrounding tissue, an intervertebral disc, or the intervertebral disc's surrounding tissue that is capable of holding the instant celecoxib-containing biodegradable microspheres such that the celecoxib released therefrom can act on the joint. Suitable joint-related tissue includes, without limitation, (i) articular and periarticular spaces; (ii) the bursa, synovial cavity, joint capsule with synovial lining, and the fluids contained therein; and (iii) connective and contractile tissue (e.g., articular cartilage, ligaments, tendons and muscles).

As used herein, a "suitable matrix" for a biodegradable microsphere includes, without limitation, a polylactic-co-glycolic acid copolymer (PLGA) matrix; a hydrogel matrix (e.g., one based on poly D,L-lactide and polyethylene glycol (PEG)); a poly-caprolactone matrix; an ethylcellulose matrix; a PLGA-polythioester matrix; a solid lipid nanoparticle matrix; an acetyl-capped PCLA-PEG-PCLA thermogel matrix; a polyester amide (PEA) matrix; and a chitosan matrix. In the preferred embodiment, the suitable matrix is a polylactic-co-glycolic acid copolymer (PLGA) matrix.

As used herein, the term "therapeutically effective amount", with respect to pharmaceutical celecoxib carried in biodegradable microspheres, refers to the amount of pharmaceutical celecoxib collectively carried by the total dose of biodegradable microspheres introduced in or around one of a subject's joints. In one embodiment, the effective amount is 1 µg, 5 µg, 10 µg, 15 µg, 20 µg, 25 µg, 30 µg, 40 µg, 50 µg, 60 µg, 70 µg, 80 µg, 90 µg, 100 µg, 150 µg, 200 µg, 250 µg, 300 µg, 350 µg, 400 µg, 450 µg, 500 µg, 550 µg, 600 µg, 650 µg, 700 µg, 750 µg, 800 µg, 850 µg, 900 µg, 950 µg, 1 mg, 5 mg, 10 mg, 15 mg, 20 mg, 25 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1,000 mg, 1,050 mg, 1,100 mg, 1,150 mg, 1,200 mg, 1,250 mg, 1,300 mg, 1,350 mg, 1,400 mg, 1,450 mg, 1,500 mg, 1,550 mg, 1,600 mg, 1,650 mg, 1,700 mg, 1,750 mg, 1,800 mg, 1,850 mg, 1,900 mg, 1,950 mg, or 2,000 mg. In another embodiment, the effective amount is from 1 µg to 10 µg, from 10 µg to 50 µg, from 50 µg to 100 µg, from 100 µg to 150 µg, from 150 µg to 200 µg, from 200 µg to 250 µg, from 250 µg to 300 µg, from 300 µg to 350 µg, from 350 µg to 400 µg, from 400 µg to 450 µg, from 450 µg to 500 µg, from 500 µg to 550 µg, from 550 µg to 600 µg, from 600 µg to 650 µg, from 650 µg to 700 µg, from 700 µg to 750 µg, from 750 µg to 800 µg, from 800 µg to 850 µg, from 850 µg to 900 µg, from 900 µg to 950 µg, from 950 µg to 1 mg, 1 mg to 10 mg, from 10 mg to 50 mg, from 50 mg to 100 mg, from 100 mg to 150 mg, from 150 mg to 200 mg, from 200 mg to 250 mg, from 250 mg to 300 mg, from 300 mg to 350 mg, from 350 mg to 400 mg, from 400 mg to 450 mg, from 450 mg to 500 mg, from 500 mg to 550 mg, from 550 mg to 600 mg, from 600 mg to 650 mg, from 650 mg to 700 mg, from 700 mg to 750 mg, from 750 mg to 800 mg, from 800 mg to 850 mg, from 850 mg to 900 mg, from 900 mg to 950 mg, from 950 mg to 1,000 mg, from 1,050 mg to 1,100 mg, from 1,100 mg to 1,150 mg, from 1,150 mg to 1,200 mg, from 1,200 mg to 1,250 mg, from 1,250 mg to 1,300 mg, from 1,300 mg to 1,350 mg, from 1,350 mg to 1,400 mg, from 1,400 mg to 1,450 mg, from 1,450 mg to 1,500 mg, from 1,500 mg to 1,550 mg, from 1,550 mg to 1,600 mg, from 1,600 mg to 1,650 mg, from 1,650 mg to 1,700 mg, from 1,700 mg to 1,750 mg, from 1,750 mg to 1,800 mg, from 1,800 mg to 1,850 mg, from 1,850 mg to 1,900 mg, from 1,900 mg to 1,950 mg, or from 1,950 mg to 2,000 mg. In a further embodiment, the effective amount is from 1 µg to 250 µg, from 250 µg to 500 µg, from 500 µg to 750 µg, from 750 µg to 1 mg, 1 mg to 250 mg, from 250 mg to 500 mg, from 500 mg to 750 mg, from 750 mg to 1,000 mg, from 1,000 mg to 1,250 mg, from 1,250 mg to 1,500 mg, from 1,500 mg to 1,750 mg, or from 1,750 mg to 2,000 mg. In yet a further embodiment, the effective amount is from 1 µg to 500 µg, from 500 µg to 1 mg, 1 mg to 500 mg, from 10 mg to 500 mg, from 500 mg to 1,000 mg, from 1,000 mg to 1,500 mg, or from 1,500 mg to 2,000 mg. In a further embodiment, the therapeutically effective amount of celecoxib is an amount sufficient to achieve a celecoxib concentration in the synovial fluid of, for example, 0.1 ng/ml, 0.2 ng/ml, 0.3 ng/ml, 0.4 ng/ml, 0.5 ng/ml, 0.6 ng/ml, 0.7 ng/ml, 0.8 ng/ml, 0.9 ng/ml, 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 20 ng/ml, 40 ng/ml, 60 ng/ml, 80 ng/ml, 100 ng/ml, 120 ng/ml, 140 ng/ml, 160 ng/ml, 180 ng/ml, 200 ng/ml, 250 ng/ml, 300 ng/ml, 350 ng/ml, 400 ng/ml, 450 ng/ml, 500 ng/ml, 550 ng/ml, 600 ng/ml, 650 ng/ml, 700 ng/ml, 750 ng/ml, 800 ng/ml, 850 ng/ml, 900 ng/ml, 950 ng/ml, 1,000 ng/ml, 2,000 ng/ml, 3,000 ng/ml, 4,000 ng/ml, 5,000 ng/ml, 6,000 ng/ml, 7,000 ng/ml, 8,000 ng/ml, 9,000 ng/ml, 10,000 ng/ml, 20,000 ng/ml, from 0.1 ng/ml to 0.5 ng/ml, from 0.5 ng/ml to 1 ng/ml, from 1 ng/ml to 5 ng/ml, from 5 ng/ml to 10 ng/ml, from 10 ng/ml to 15 ng/ml, from 15 ng/ml to 20 ng/ml, from 20 ng/ml to 25 ng/ml, from 25 ng/ml to 50 ng/ml, from 50 ng/ml to 75 ng/ml, from 75 ng/ml to 100 ng/ml, from 100 ng/ml to 125 ng/ml, from 125 ng/ml to 150 ng/ml, from 150 ng/ml to 200 ng/ml, from 200 ng/ml to 300 ng/ml, from 300 ng/ml to 400 ng/ml, from 400 ng/ml to 500 ng/ml, from 500 ng/ml to 600 ng/ml, from 600 ng/ml to 700 ng/ml, from 700 ng/ml to 800 ng/ml, from 800 ng/ml to 900 ng/ml, from 900 ng/ml to 1,000 ng/ml, from 1,000 ng/ml to 2,000 ng/ml, from 2,000 ng/ml to 3,000 ng/ml, from 3,000 ng/ml to 4,000 ng/ml, from 4,000 ng/ml to 5,000 ng/ml, from 5,000 ng/ml to 6,000 ng/ml, from 6,000 ng/ml to 7,000 ng/ml, from 7,000 ng/ml to 8,000 ng/ml, from 8,000 ng/ml to 9,000 ng/ml, from 9,000 ng/ml to 10,000 ng/ml, or from 10,000 ng/ml to 20,000 ng/ml.

As used herein, "treating" a subject afflicted with a disorder shall include, without limitation, (i) slowing, stopping or reversing the disorder's progression, (ii) slowing, stopping or reversing the progression of the disorder's symptoms (e.g., pain), (iii) reducing the likelihood of the disorder's recurrence, and/or (iv) reducing the likelihood that the disorder's symptoms will recur. In the preferred embodiment, treating a subject afflicted with a disorder means (i) reversing the disorder's progression, ideally to the point of eliminating the disorder, and/or (ii) reversing the progression of the disorder's symptoms, ideally to the point of eliminating the symptoms.

Embodiments of the Invention

This invention solves an unmet need in the art by providing an unexpectedly superior way to treat joint-related disorders using celecoxib. The invention does this via celecoxib-carrying microspheres that release celecoxib over time.

Specifically, this invention provides a biodegradable microsphere, wherein the microsphere (i) has a diameter of from 1 µm to 500 µm; (ii) comprises a polylactic-co-glycolic acid copolymer (PLGA) matrix; (iii) carries pharmaceutical celecoxib; and (iv) when present in a suitable joint-related tissue, releases celecoxib for at least one month.

In one embodiment of the instant biodegradable microsphere, it has a lactic acid to glycolic acid molar ratio of from 100:0 to 50:50. Preferably, the instant microsphere (i) has a diameter of from 20 µm to 200 µm; and (ii) has a lactic acid to glycolic acid molar ratio of 75:25.

In another embodiment of the instant biodegradable microsphere, it further comprises polyethylene glycol (PEG). The PEG can be any type suitable for use in forming biodegradable microspheres (e.g., PEG1450 (Polysciences, Inc., Warrington, PA)). Moreover, the ratio of PEG to PLGA can be any ratio suitable for use in forming biodegradable microspheres (e.g., 25:100, 50:100, 75:100 or 100:100).

In yet another embodiment of the instant biodegradable microsphere, when it is present in a suitable joint-related tissue, it releases celecoxib for longer than one month. Preferably, the microsphere, when present in a suitable joint-related tissue, releases celecoxib for at least two months, at least three months, at least four months, at least five months, at least six months, at least seven months, at least eight months, at least nine months, at least ten months, at least eleven months, or at least twelve months.

The following celecoxib-containing biodegradable microspheres are preferred embodiments of this invention. The microsphere population comprises PLGA75:25 (i.e., wherein the L:G ratio is 75:25), 0.5-1.0 dl/g, ester-terminated, with celecoxib loading of 50%-75% (calculated as celecoxib/(celecoxib+PLGA)). For example, for each 2.5 mg of PLGA75:25, 0.6 dl/g, ester-terminated, 5 mg celecoxib is encapsulated to form 7.5 mg microspheres. In another example, for each 2.5 mg of PLGA75:25, 0.9 dl/g, ester-terminated, 5 mg celecoxib is encapsulated to form 7.5 mg microspheres. For each 2.5 mg PLGA and 5 mg celecoxib, the microspheres are prepared by dissolving the PLGA and celecoxib in 200 μl of dichloromethane, injected into the center of 50 ml of 0.5-1.5% poly-vinyl-alcohol (PVA, w/v, molecular weight 31-50K, 98-99% hydrolyzed), stirred with a magnetic stir bar (2 cm in length, 0.7 cm in diameter) at 1,200 rpm for 2 minutes in a 50 ml beaker and then at about 500 rpm for 2 hours. The PVA concentration is adjusted to have an absorption of 0.160 at 230 nm wavelength.

This invention also provides a plurality of biodegradable microspheres, wherein the microspheres (i) have a $d_{90}$ value from 1 μm to 500 μm; (ii) comprise a polylactic-co-glycolic acid copolymer (PLGA) matrix; (iii) carry a therapeutically effective amount of pharmaceutical celecoxib; and (iv) when present in a suitable joint-related tissue, release celecoxib for at least one month.

In an embodiment of the instant plurality of biodegradable microspheres, the microspheres further comprise polyethylene glycol (PEG).

In another embodiment of the instant plurality of biodegradable microspheres, the microspheres, when present in a suitable joint-related tissue, release celecoxib for longer than one month. Preferably, the microspheres, when present in a suitable joint-related tissue, release celecoxib for at least two months, at least three months, at least four months, at least five months, at least six months, at least seven months, at least eight months, at least nine months, at least ten months, at least eleven months, or at least twelve months.

In a further embodiment of the instant plurality of biodegradable microspheres, the microspheres (i) have a $d_{90}$ value from 20 μm to 200 μm; (ii) have a lactic acid to glycolic acid molar ratio of from 100:0 to 50:50; and (iii) carry from 1 μg to 500 mg of pharmaceutical celecoxib.

This invention further provides an injectable formulation comprising (a) a pharmaceutically acceptable carrier and (b) a plurality of biodegradable microspheres wherein the microspheres (i) have a $d_{90}$ value from 1 μm to 500 μm; (ii) comprise a polylactic-co-glycolic acid copolymer (PLGA) matrix; (iii) carry a therapeutically effective amount of pharmaceutical celecoxib; and (iv) when present in a suitable joint-related tissue, release celecoxib for at least one month.

In an embodiment of the instant formulation, the microspheres further comprise polyethylene glycol (PEG).

In another embodiment of the instant formulation, the microspheres, when present in a suitable joint-related tissue, release celecoxib for longer than one month. Preferably, the microspheres, when present in a suitable joint-related tissue, release celecoxib for at least two months, at least three months, at least four months, at least five months, at least six months, at least seven months, at least eight months, at least nine months, at least ten months, at least eleven months, or at least twelve months.

This invention still further provides a method for treating a joint-related disorder in a subject comprising introducing biodegradable microspheres into suitable tissue in or around one or more of the subject's joints, wherein the microspheres (i) have a $d_{90}$ value from 1 μm to 500 μm; (ii) comprise a polylactic-co-glycolic acid copolymer (PLGA) matrix; (iii) carry a therapeutically effective amount of pharmaceutical celecoxib; and (iv) when present in a suitable joint-related tissue, release celecoxib for at least one month.

In an embodiment of the instant method, the microspheres further comprise polyethylene glycol (PEG).

In a preferred embodiment of the instant method, the subject is human. In another preferred embodiment of the instant method, the subject is a cat, a dog, or a horse. In another preferred embodiment of the instant method, the disorder is arthritis (e.g., osteoarthritis or rheumatoid arthritis).

In this invention, the biodegradable microspheres can be introduced into the suitable tissue in or around one or more of the subject's joints using any known method appropriate for the tissue in question. For example, in a preferred embodiment of the instant method where the tissue is synovial fluid in the knee joint, the method comprises intra-articularly injecting the biodegradable microspheres into the synovial fluid of one or both of the subject's knees. In another embodiment, the instant method is performed a plurality of times (e.g., two times, three times, four times, five times, or more). In that embodiment, each subsequent time the method is performed, it is performed after a suitable period has lapsed since the preceding time the method was performed. This suitable time can be, for example, one month, two months, three months, four months, five months, six months, one year, or longer. Microsphere-based drug products and methods of delivering them are known, at least generally (e.g., Zilretta® (triamcinolone acetonide extended-release injectable suspension for intra-articular use (Flexion)); and Sandostatin LAR® Depot (octreotide acetate for injectable suspension) (Novartis)).

In a further preferred embodiment of the instant method, the microspheres (i) have a $d_{90}$ value from 20 μm to 200 μm (e.g., from 20 μm to 150 μm); (ii) have a lactic acid to glycolic acid molar ratio of from 100:0 to 50:50 (e.g., 75:25); and (iii) carry from 1 μg to 500 mg of pharmaceutical celecoxib.

In yet another embodiment of the instant method, the microspheres, when present in a suitable joint-related tissue, release celecoxib for longer than one month. Preferably, the microspheres, when present in a suitable joint-related tissue, release celecoxib for at least two months, at least three months, at least four months, at least five months, at least six months, at least seven months, at least eight months, at least nine months, at least ten months, at least eleven months, or at least twelve months.

This invention further provides an article of manufacture (kit) comprising, in separate compartments, (a) one of, and ideally both of, (i) a diluent and (ii) a label instructing the user to introduce the biodegradable microspheres (described below) into suitable tissue in or around one or more of a subject's joints, and (b) a plurality of biodegradable microspheres, wherein the microspheres (i) have a $d_{90}$ value from 1 μm to 500 μm (e.g., from 20 μm to 200 μm, or from 20 μm to 150 μm); (ii) comprise a polylactic-co-glycolic acid copolymer (PLGA) matrix (preferably having a lactic acid to glycolic acid molar ratio of from 100:0 to 50:50 (e.g., 75:25)); (iii) carry a therapeutically effective amount of pharmaceutical celecoxib (e.g., from 1 μg to 500 mg of pharmaceutical celecoxib); and (iv) when present in a suitable joint-related tissue, release celecoxib for at least one month (and optionally release celecoxib for at least two months, at least three months, at least four months, at least five months, at least six months, at least seven months, at least eight months, at least nine months, at least ten months, at least eleven months, or at least twelve months). In one embodiment of the instant kit, the microspheres further comprise polyethylene glycol (PEG). Where applicable, the embodiments described above for the instant methods are also envisioned for this article of manufacture.

In a preferred embodiment, the instant kit is supplied as a single-dose kit, and contains (i) a single dose vial of celecoxib-carrying biodegradable microspheres, and (ii) a single dose vial of diluent (e.g., sterile, clear liquid solution of 0.9% w/w sodium chloride, 0.5%-1% w/w sodium carboxymethylcellulose, and 0.1% w/w polysorbate-80).

This invention provides a biodegradable microsphere, wherein the microsphere (i) has a diameter of from 1 μm to 500 μm; (ii) comprises a suitable matrix (e.g., a polylactic-co-glycolic acid copolymer (PLGA) matrix); (iii) carries pharmaceutical celecoxib; and (iv) when present in a suitable joint-related tissue, releases celecoxib for at least one month, wherein the celecoxib so released is characterized (e.g., when measured at 14 days post-injection) by (i) a synovial membrane to synovial fluid celecoxib concentration ratio (i.e., the ratio of synovial membrane celecoxib concentration to synovial fluid celecoxib concentration) of at least 20, and/or (ii) a joint cartilage to synovial fluid celecoxib concentration ratio (i.e., the ratio of joint cartilage (e.g., femur cartilage or tibia cartilage) celecoxib concentration to synovial fluid celecoxib concentration) of at least 10. The biodegradable microsphere components, dimensions, features, and celecoxib release duration described above are envisioned, mutatis mutandis, for this biodegradable microsphere. In a preferred embodiment, the synovial membrane to synovial fluid celecoxib concentration ratio is at least 100, at least 500, at least 1,000, at least 1,500, at least 2,000, at least 2,500, at least 3,000, at least 3,500, at least 4,000, or at least 5,000. In another preferred embodiment, the joint cartilage (i.e., femur cartilage) to synovial fluid celecoxib concentration ratio is at least 15, at least 20, at least 25, at least 30, at least 35, at least 40, at least 45, at least 50, at least 60, at least 70, at least 80, at least 90, or at least 100. In a further preferred embodiment, the joint cartilage (i.e., tibia cartilage) to synovial fluid celecoxib concentration ratio is at least 15, at least 20, at least 25, at least 30, at least 35, at least 40, at least 45, at least 50, at least 60, at least 70, at least 80, at least 90, or at least 100. Methods for measuring celecoxib concentrations in synovial membrane, synovial fluid, and joint cartilage are known, and are exemplified by a number of references. For example, methods for measuring celecoxib concentration in plasma and synovial fluid are exemplified by Hunter et al. (2004). Methods for measuring celecoxib concentration in synovial membrane are exemplified by G. Gaudriault, et al.

This invention also provides a plurality of biodegradable microspheres, wherein the microspheres (i) have a $d_{90}$ value from 1 μm to 500 μm; (ii) comprise a suitable matrix (e.g., a polylactic-co-glycolic acid copolymer (PLGA) matrix); (iii) carry a therapeutically effective amount of pharmaceutical celecoxib; and (iv) when present in a suitable joint-related tissue, release celecoxib for at least one month, wherein the celecoxib so released is characterized (e.g., when measured at 14 days post-injection) by (i) a synovial membrane to synovial fluid celecoxib concentration ratio of at least 20, and/or (ii) a joint cartilage to synovial fluid celecoxib concentration ratio of at least 10. The biodegradable microsphere components, dimensions, features, celecoxib dosing, and celecoxib release duration described above are envisioned, mutatis mutandis, for this plurality of biodegradable microspheres. In a preferred embodiment, the synovial membrane to synovial fluid celecoxib concentration ratios and the joint cartilage to synovial fluid celecoxib concentration ratios are as described above.

This invention further provides an injectable formulation comprising (a) a pharmaceutically acceptable carrier and (b) a plurality of biodegradable microspheres wherein the microspheres (i) have a $d_{90}$ value from 1 μm to 500 μm; (ii) comprise a suitable matrix (e.g., a polylactic-co-glycolic acid copolymer (PLGA) matrix); (iii) carry a therapeutically effective amount of pharmaceutical celecoxib; and (iv) when present in a suitable joint-related tissue, release celecoxib for at least one month, wherein the celecoxib so released is characterized (e.g., when measured at 14 days post-injection) by (i) a synovial membrane to synovial fluid celecoxib concentration ratio of at least 20, and/or (ii) a joint cartilage to synovial fluid celecoxib concentration ratio of at least 10. The biodegradable microsphere components, dimensions, features, celecoxib dosing, and celecoxib release duration described above are envisioned, mutatis mutandis, for this injectable formulation. In a preferred embodiment, the synovial membrane to synovial fluid celecoxib concentration ratios and the joint cartilage to synovial fluid celecoxib concentration ratios are as described above.

This invention still further provides a method for treating a joint-related disorder in a subject comprising introducing biodegradable microspheres into suitable tissue in or around one or more of the subject's joints, wherein the microspheres (i) have a $d_{90}$ value from 1 μm to 500 μm; (ii) comprise a suitable matrix (e.g., a polylactic-co-glycolic acid copolymer (PLGA) matrix); (iii) carry a therapeutically effective amount of pharmaceutical celecoxib; and (iv) when present in a suitable joint-related tissue, release celecoxib for at least one month, wherein the celecoxib so released is characterized (e.g., when measured at 14 days post-injection) by (i) a synovial membrane to synovial fluid celecoxib concentration ratio of at least 20, and/or (ii) a joint cartilage to synovial fluid celecoxib concentration ratio of at least 10. The (i) biodegradable microsphere components, dimensions, features, celecoxib dosing, and celecoxib release duration, and (ii) therapeutic indications, subjects, and modes of administration described above are envisioned, mutatis mutandis, for this method. In a preferred embodiment, the synovial membrane to synovial fluid celecoxib concentration ratios and the joint cartilage to synovial fluid celecoxib concentration ratios are as described above.

Finally, this invention provides a kit comprising, in separate compartments, (a) a diluent, and (b) plurality of biodegradable microspheres, wherein the microspheres (i) have a $d_{90}$ value from 1 μm to 500 μm; (ii) comprise a suitable matrix (e.g., a polylactic-co-glycolic acid copolymer (PLGA) matrix); (iii) carry a therapeutically effective amount of pharmaceutical celecoxib; and (iv) when present in a suitable joint-related tissue, release celecoxib for at least one month, wherein the celecoxib so released is characterized (e.g., when measured at 14 days post-injection) by (i) a synovial membrane to synovial fluid celecoxib concentration ratio of at least 20, and/or (ii) a joint cartilage to synovial fluid celecoxib concentration ratio of at least 10. The diluents, biodegradable microsphere components, dimensions, features, celecoxib dosing, and celecoxib release duration described above are envisioned, mutatis mutandis, for this kit. In a preferred embodiment, the synovial membrane to synovial fluid celecoxib concentration ratios and the joint cartilage to synovial fluid celecoxib concentration ratios are as described above.

The subject biodegradable microspheres, formulations, methods, and kits are envisioned in this invention for (a) administration to (i) epidural and perineural spaces, (ii) the foramenal space at or near the site of a patient's pain or inflammation, and (iii) sites of injury or surgery, as well as (b) treatment of non-joint-related indications such as post-surgical pain relief (e.g., relief of pain due to hernia repair, abdominoplasty, or bunionectomy), mutatis mutandis, as they are for suitable joint-related tissue.

This invention will be better understood by reference to the examples which follow, but those skilled in the art will readily appreciate that the specific examples detailed are only illustrative of the invention as described more fully in the claims which follow thereafter.

EXAMPLES

Example 1. Experimental Materials and Methods Generally

PLGA refers to poly-lactic-co-glycolic acid; PDLA refers to poly-D-lactic acid, which is one kind of poly-lactic acid (PLA); DMSO refers to dimethyl sulfoxide; PVA refers to poly-vinyl-alcohol, molecular weight: 31-50K, 98-99% hydrolyzed; PBS refers to phosphate buffered saline, pH 7.4; and MW refers to molecular weight. The magnetic stir bar used in all of the following examples is 2 cm in length and 0.7 cm in diameter.

(i) PDLA, 0.4 dl/g, ester-terminated: Intrinsic viscosity=0.35-0.45 dl/g. MW: 20,000-30,000; (ii) PDLA, 0.6 dl/g, ester-terminated: Intrinsic viscosity=0.55-0.65 dl/g; (iii) PDLA, 2 dl/g, ester-terminated: Intrinsic viscosity=1.6-2.4 dl/g. MW: 300,000-600,000; (iv) PLGA50:50, 0.2 dl/g, acid-terminated: Intrinsic viscosity=0.16-0.24 dl/g. MW: 7,000-17,000; (v) PLGA50:50, 0.2 dl/g, ester-terminated: Intrinsic viscosity=0.16-0.24 dl/g. MW: 7,000-17,000; (vi) PLGA50:50, 0.4 dl/g, acid-terminated: Intrinsic viscosity=0.32-0.44 dl/g. MW: 24,000-38,000; (vii) PLGA50:50, 0.4 dl/g, ester-terminated: Intrinsic viscosity=0.32-0.44 dl/g. MW: 24,000-38,000; (viii) PLGA50:50, 0.5 dl/g, acid-terminated: Intrinsic viscosity=0.45-0.6 dl/g. MW: 38,000-54,000; (ix) PLGA50:50, 0.5 dl/g, ester-terminated: Intrinsic viscosity=0.45-0.6 dl/g. MW: 38,000-54,000; (x) PLGA50:50, 0.6 dl/g, ester-terminated: Intrinsic viscosity=0.50-0.65 dl/g; (xi) PLGA50:50, 0.7 dl/g, ester-terminated: Intrinsic viscosity=0.61-0.74 dl/g. MW: 54,000-69,000; (xii) PLGA65:35, 0.4 dl/g, acid-terminated: Intrinsic viscosity=0.32-0.44 dl/g. MW: 24,000-38,000; (xiii) PLGA75:25, 0.2 dl/g, acid-terminated: Intrinsic viscosity=0.15-0.25 dl/g. MW: 10,000-18,000; (xiv) PLGA75:25, 0.2 dl/g, ester-terminated: Intrinsic viscosity=0.16-0.24 dl/g; (xv) PLGA75:25, 0.4 dl/g, acid-terminated: Intrinsic viscosity=0.32-0.44 dl/g; (xvi) PLGA75:25, 0.6 dl/g, ester-terminated: Intrinsic viscosity=0.5-0.7 dl/g; (xvii) PLGA75:25, 0.65 dl/g, ester-terminated: Intrinsic viscosity=0.55-0.75 dl/g. MW: about 97,000; (xviii) PLGA75:25, 0.9 dl/g, ester-terminated: Intrinsic viscosity=0.71-1.0 dl/g. MW: 76,000-115,000; (xix) PLGA75:25, 1.2 dl/g, ester-terminated: Intrinsic viscosity=0.9-1.3 dl/g; (xx) PLGA85:15, 0.6 dl/g, ester-terminated: Intrinsic viscosity=0.55-0.75 dl/g. MW: 190,000-240,000; and (xxi) PLGA85:15, 1.5 dl/g, ester-terminated: Intrinsic viscosity=1.3-1.7 dl/g.

In experiments described herein, one type of PVA (i.e., of one molecular weight and degree of hydrolysis) at one concentration (i.e., 1%) is used to produce microspheres. However, in this invention, other types of PVA (for example, EMRPOVE PVA 4-88, Millipore Sigma) and other PVA concentrations are also envisioned to yield the same microspheres. For example, where 1% PVA, 200 μl dichloromethane, and 1,000 rpm stirring, is used to produce a certain population of microspheres, 0.5% PVA, 300 μl dichloromethane, and 1,400 rpm stirring, can also be used to produce essentially the same population of microspheres. Surfactants other than PVA can also be used in this invention to produce microspheres. These other surfactants include, for example, the commonly known surfactants vitamin E, Tween-20, Tween-80, poloxamers, poloxamines, pluronic polymers (such as F68 and F127), and sodium cholate. Similarly, in experiments described herein, dichloromethane is used to produce microspheres. However, in this invention, other types of organic solvents (e.g., ethyl acetate, chloroform, acetone, propylene carbonate, and tetrahydrofuran) may be used instead of dichloromethane to yield essentially the same microspheres, assuming other experimental parameters are adjusted accordingly. Moreover, in this invention, any of a plurality of physical methods for preparing PLGA microspheres (e.g., spinning disk, spray drying, and microfluidics) may be used to yield the subject microspheres.

Example 2. Microsphere Formulations of Diclofenac Acid: Effects of Polymer Composition on Diclofenac Acid Release (I)

A pharmaceutical depot was prepared comprised of the NSAID, diclofenac acid (2-[2-(2,6-dichloroanilino)phenyl] acetic acid), incorporated into microspheres. Formulations were prepared by dissolving 50 mg of PLGA or PDLA and 20 mg of diclofenac acid in 440 μl of dichloromethane and 60 μl of DMSO. The 500 μl of solution was injected into the center of 200 ml of 1% PVA (w/v, pH adjusted to 2) in a 250 ml beaker, stirred at 2,000 rpm with a magnetic stir bar to form an emulsion. The emulsion was stirred at 2,000 rpm for 2 minutes and stirred at about 500 rpm for 2 hours to evaporate the dichloromethane. The microspheres were harvested by centrifugation at 4,000 g for 5 minutes, washed with water for three times.

For testing diclofenac acid release from the microspheres, all prepared microspheres were added to 250 ml of 10 mM PBS and shaken at 80 rpm at 37° C. At each time point in the release study, microspheres were allowed to settle, and an aliquot of 650 μl was taken for measuring UV absorption and added back to the original solution. Diclofenac acid concentration was determined by UV absorption at a wavelength of 276 nm.

FIG. 1 shows the release of diclofenac acid in a range of PLGA and PDLA microspheres. The PLGA50:50, 0.6 dl/g, ester-terminated formulation showed complete diclofenac acid release within 30 days. The PLGA75:25, 0.65 dl/g, ester-terminated formulation showed little diclofenac acid release from day 6 to day 16, which is unsuitable for continuous drug delivery. The PLGA85:15, 0.6 dl/g, ester-terminated formulation showed little diclofenac acid release from day 10 to day 16, which is unsuitable for continuous drug delivery. The PDLA, 2 dl/g, ester-terminated formulation showed little diclofenac acid release from day 6 to day 16, which is unsuitable for continuous drug delivery.

Figure 2:
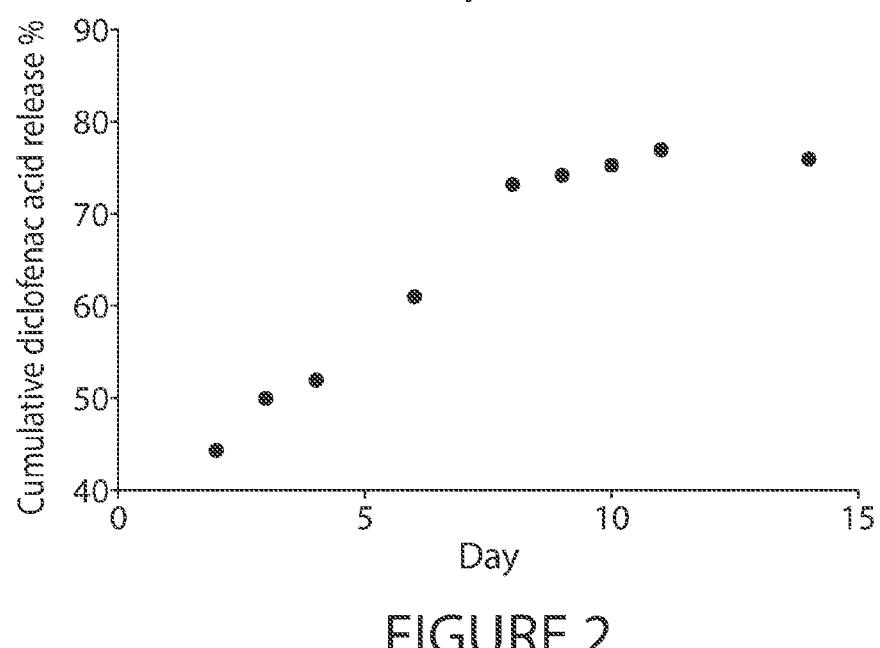

FIG. 2 shows the release of diclofenac acid in PLGA50: 50, 0.2 dl/g, acid-terminated microspheres. Release was complete by day 14, which is unsuitable for continuous drug delivery over multiple months. In some experiments, cumulative drug release may not reach 100%, due to minor variations in instrumental readings.

Example 3. Microsphere Formulations of Diclofenac Acid: Effects of Polymer Composition on Diclofenac Acid Release (II)

In another set of experiments, formulations were prepared by dissolving 5 mg of PLGA or PDLA and 2 mg of diclofenac acid in 180 µl of dichloromethane and 20 µl DMSO. The 200 µl of solution was injected into the center of 50 ml of 1% PVA (w/v, pH adjusted to 2) in a 50 ml beaker, stirred at 1,000 rpm with a magnetic stir bar to form an emulsion. The emulsion was stirred at 1,000 rpm for 2 minutes and stirred at about 500 rpm for 2 hours to evaporate the dichloromethane. The microspheres were harvested by centrifugation at 4,000 g for 5 minutes, washed with 50 ml water for three times.

For testing diclofenac acid release from the microspheres, all prepared microspheres were added to 250 ml of 10 mM PBS and shaken at 80 rpm at 37° C. At each time point in the release study, microspheres were allowed to settle, and an aliquot of 650 µl was taken for measuring UV absorption and added back to the original solution. Diclofenac acid concentration was determined by UV absorption at a wavelength of 276 nm.

Figure 3:
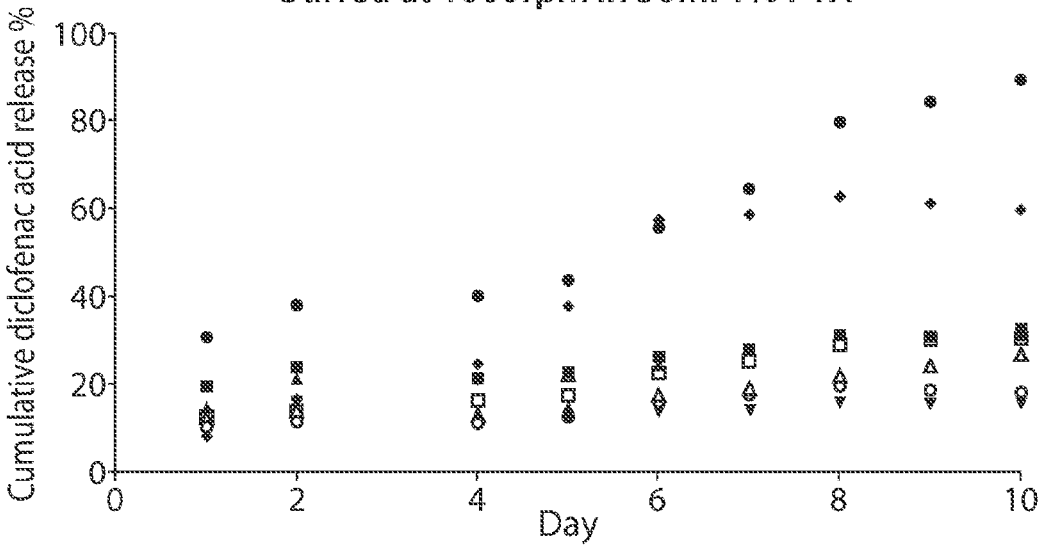

FIG. 3 shows the diclofenac acid release from a range of PLGA and PDLA formulations. The PLGA50:50, 0.2 dl/g, acid-terminated formulation resulted in complete drug release in about 10 days. All other formulations resulted in little drug release from day 7 to day 10. None of these formulations is suitable for continuous drug delivery over multiple months.

Example 4. Microsphere Formulations of Diclofenac Acid: Effects of Mixed PLGA or PDLA on Diclofenac Acid Release Since PLGA50:50, 0.2 dl/g, acid-terminated formulations released diclofenac acid very quickly within 15 days, and some other formulations (such as PLGA75:25, 0.65 dl/g, ester-terminated, PLGA85:15, 0.6 dl/g, ester-terminated, PDLA, 0.4 dl/g, ester-terminated) released diclofenac acid too slowly, or stopped drug release after day 7, mixed PLGA or PDLA formulations were tested to obtain formulations that may achieve continuous drug release over 30 days.

Formulations were prepared by dissolving 5 mg of PLGA or PDLA and 2 mg of diclofenac acid in 180 µl of dichloromethane and 20 µl DMSO. The 5 mg of PLGA or PDLA was comprised of various ratios of PLGA50:50, 0.2 dl/g, acid-terminated, PLGA85:15, 0.6 dl/g, ester-terminated, PLGA75:25, 0.65 dl/g, ester-terminated, and PDLA, 0.4 dl/g, ester-terminated. The 200 µl of solution was injected into the center of 50 ml of 1% PVA (w/v, pH adjusted to 2) in a 50 ml beaker, stirred at 1,000 rpm with a magnetic stir bar to form an emulsion. The emulsion was stirred at 1,000 rpm for 2 minutes and stirred at about 500 rpm for 2 hours to evaporate the dichloromethane. The microspheres were harvested by centrifugation at 4,000 g for 5 minutes, washed with 50 ml water for three times.

For testing diclofenac acid release from the microspheres, all prepared microspheres were added to 250 ml of 10 mM PBS and shaken at 80 rpm at 37° C. At each time point in the release study, microspheres were allowed to settle, and an aliquot of 650 µl was taken for measuring UV absorption and added back to the original solution. Diclofenac acid concentration was determined by UV absorption at a wavelength of 276 nm.

Figure 4:
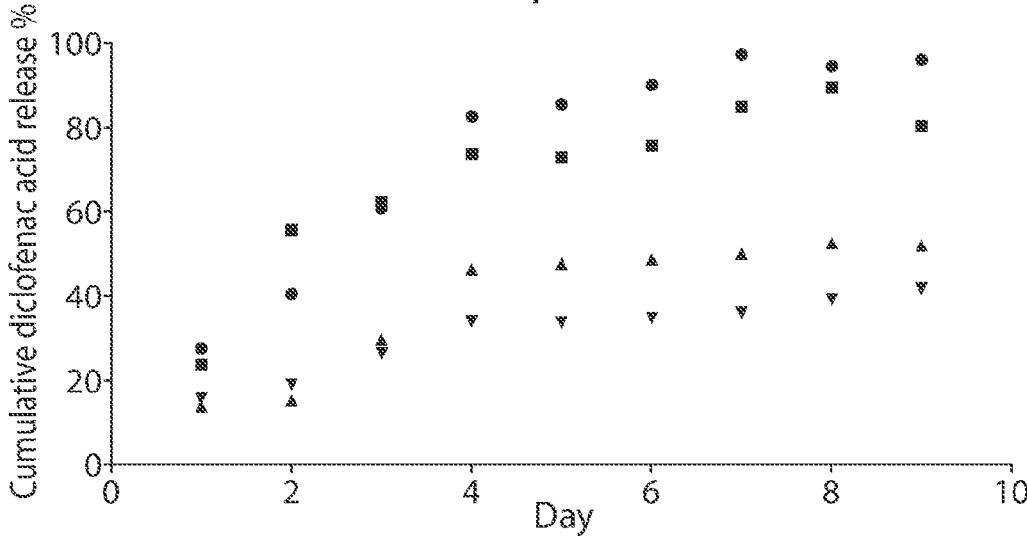
Figure 5:
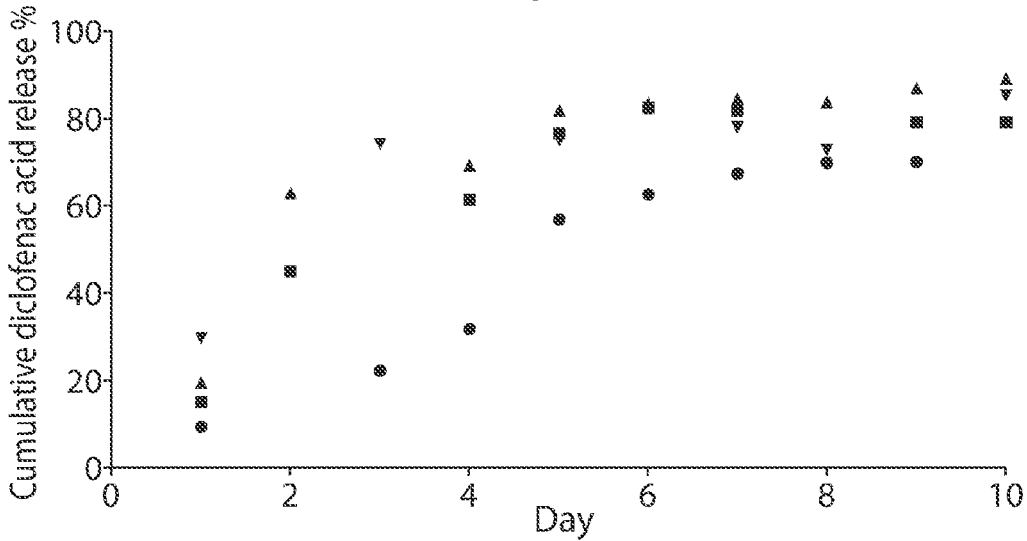

FIG. 4 shows that both formulations involving PLGA85: 15, 0.6 dl/g, ester-terminated resulted in complete diclofenac acid release within 10 days. Both formulation involving PDLA, 0.4 dl/g, ester-terminated released little diclofenac acid from day 4 to day 9. FIG. 5 shows complete diclofenac acid release in 10 days. None of these formulations is suitable for continuous drug release over multiple months.

Example 5. Microsphere Formulations of Lornoxicam

Microsphere formulations of another NSAID, lornoxicam (6-chloro-4-hydroxy-2-methyl-1,1-dioxo-N-pyridin-2-yl-thieno[2,3-e]thiazine-3-carboxamide), were prepared with various PLGA and PDLA polymers, including PLGA50:50, 0.2 dl/g, acid-terminated, PLGA75:25, 0.65 dl/g, ester-terminated, PLGA50:50, 0.6 dl/g, ester-terminated, PLGA85:15, 0.6 dl/g, ester-terminated, PDLA, 0.4 dl/g, ester-terminated, and PDLA, 2 dl/g, ester-terminated. Formulations were prepared by dissolving 20 mg of PLGA or PDLA and 2 mg lornoxicam in 900 µl dichloromethane and 100 µl methanol. The 1 ml of solution was injected into the center of 50 ml of 1% PVA (w/v, pH adjusted to 2) in a 50 ml beaker, stirred at 800 rpm with a magnetic stir bar to form an emulsion. The emulsion was stirred at 800 rpm for 2 minutes and stirred at about 500 rpm for 2 hours to evaporate the dichloromethane.

Figure 6:
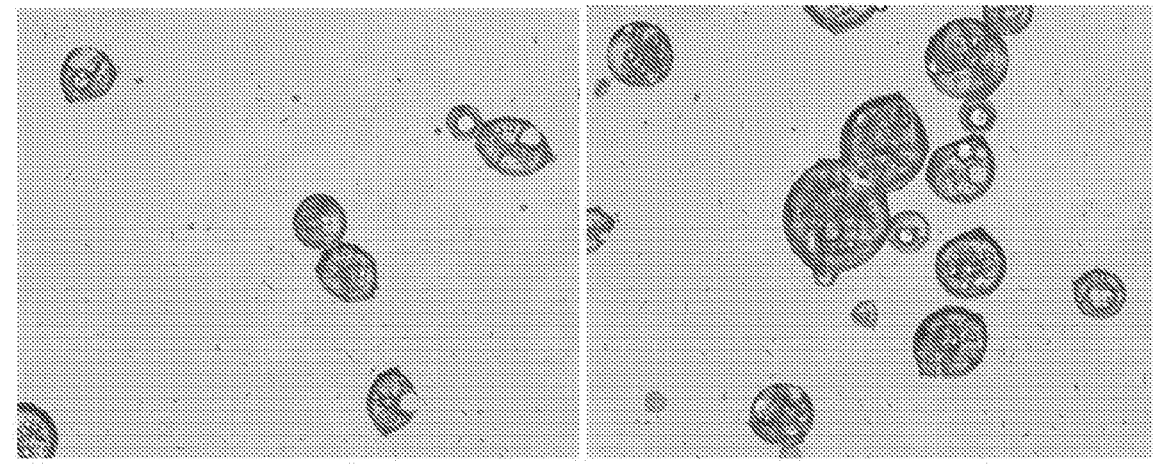

FIG. 6 shows the microsphere formation of lornoxicam-PLGA microspheres (PLGA50:50, 0.2 dl/g, acid-terminated). Crystal rods and spikes formed during evaporation of dichloromethane and precipitation of lornoxicam. The rods and spikes of lornoxicam crystals prevented the formation of microspheres. These formulations are unsuitable for continuous drug delivery of lorxicam over multiple months.

Example 6. Microsphere Formulations of Celecoxib: Effects of Polymer Composition on Celecoxib Release Formulations were prepared by dissolving 2.5 mg PLGA and 1 mg celecoxib in 100 µl dichloromethane. The 100 µl of solution was injected into the center of 50 ml of 1% PVA (w/v) in a 50 ml beaker, stirred at 1,000 rpm with a magnetic stir bar to form an emulsion. The emulsion was stirred at 1,000 rpm for 2 minutes and stirred at about 500 rpm for 2 hours to evaporate the dichloromethane. The microspheres were harvested by centrifugation at 4,000 g for 5 minutes, washed with 50 ml water for three times.

For testing celecoxib release from the microspheres, all prepared microspheres were added to 250 ml of 10 mM PBS and shaken at 80 rpm at 37° C. At each time point in the release study, microspheres were allowed to settle, and an aliquot of 650 µl was taken for measuring UV absorption and added back to the original solution. If the released celecoxib in PBS reached about one third of the fully saturated concentration, 200 ml out of the 250 ml of PBS (without microspheres) was taken out and replaced with fresh 200 ml of PBS. Celecoxib concentration was determined by UV absorption at a wavelength of 230 nm.

FIG. 7 shows cumulative celecoxib release for a range of PLGA formulations. PLGA50:50, 0.2 dl/g, acid-terminated, PLGA50:50, 0.4 dl/g, acid-terminated, PLGA50:50, 0.5 dl/g, acid-terminated, and PLGA65:35, 0.4 dl/g, acid-terminated resulted in continuous celecoxib release over 7 days, 20 days, 24 days, and 25 days, respectively, which are unsuitable for continuous drug release over multiple months.

PLGA50:50, 0.4 dl/g, ester-terminated resulted in continuous celecoxib release over 30 days, and PLGA50:50, 0.6 dl/g, ester-terminated resulted in continuous celecoxib release over 37 days. Low molecular weight and correspondingly low inherent viscosity PLGA is known to allow for more complete and faster release of pharmaceutical agents incorporated into microparticles than their higher molecular weight and higher inherent viscosity counterparts. (Anderson, et al. "Biodegradation and biocompatibility of PLA and PLGA microspheres." *Advanced Drug Delivery* 28(1997): 5-24; Bouissou et al., "Poly(lactic-co-glycolic-acid) Microspheres." *Polymer in Drug Delivery* (2006): Chapter 7). Unexpectedly, PLGA50:50, 0.5 dl/g, ester-terminated resulted in slower celecoxib release than the PLGA50:50, 0.6 dl/g, ester-terminated formulation. Also, the PLGA50:50, 0.5 dl/g, ester-terminated formulation resulted in little celecoxib release from day 9 to day 15, which is unsuitable for continuous drug release over months.

PLGA75:25, 0.4 dl/g, acid-terminated resulted in continuous celecoxib release over 35 days. Unexpectedly, compared to the release curve of PLGA50:50, 0.6 dl/g, ester-terminated formulation, the celecoxib release rate was more uniform throughout the entire period of drug release for PLGA75:25, 0.4 dl/g, acid-terminated. In other words, the release rate between day 1 and day 23 was higher for PLGA75:25, 0.4 dl/g, acid-terminated, and the release rate between day 24 to day 35 was lower for PLGA75:25, 0.4 dl/g, acid-terminated. A more uniform drug release is desirable for a pharmaceutical depot formulation because it would require a lower total dosage of drug administration in order to maintain the same efficacious drug concentration throughout the entire release period in vivo.

Example 7. Microsphere Formulations of Celecoxib: Effects of Celecoxib Loading on Drug Release Formulations were prepared by dissolving 2.5 mg PLGA and different amounts of celecoxib in 200 µl dichloromethane. The 200 µl of solution was injected into the center of 50 ml of 1% PVA (w/v) in a 50 ml beaker, stirred at 1,000 rpm with a magnetic stir bar to form an emulsion. The emulsion was stirred at 1,000 rpm for 2 minutes and stirred at about 500 rpm for 2 hours to evaporate the dichloromethane. The microspheres were harvested by centrifugation at 4,000 g for 5 minutes, washed with 50 ml water for three times.

For testing celecoxib release from the microspheres, all prepared microspheres were added to 250 ml of 10 mM PBS and shaken at 80 rpm at 37° C. At each time point in the release study, microspheres were allowed to settle, and an aliquot of 650 µl was taken for measuring UV absorption and added back to the original solution. If the released celecoxib in PBS reached about one third of the fully saturated concentration, 200 ml out of the 250 ml of PBS (without microspheres) was taken out and replaced with fresh 200 ml of PBS. Celecoxib concentration was determined by UV absorption at a wavelength of 230 nm.

FIG. 8 shows that the celecoxib-loading amount from 1 mg to 2.5 mg, mixed with 2.5 mg PLGA, did not change drug release significantly. FIG. 9 shows that increasing celecoxib loading to 3-3.5 mg, mixed with 2.5 mg PLGA50:50, 0.5 dl/g, ester-terminated, resulted in continuous celecoxib release, which is different from the little drug release seen in day 9 to day 15 in formulations with lower (1 mg) celecoxib loading. Furthermore, the two PLGA50:50, 0.7 dl/g, ester-terminated formulations showed continuous celecoxib release till at least day 50. In comparison, both PLGA75:25, 0.6 dl/g, ester-terminated formulations had little celecoxib release from day 30 to day 45, which is unsuitable for continuous celecoxib release over multiple months.

Example 8. Microsphere Formulations of Celecoxib: Effects of Mixed PLGA Polymers on Celecoxib Release Since a PLGA50:50, 0.5 dl/g, acid-terminated formulation resulted in continuous celecoxib release over 24 days (FIG. 7), mixing with other PLGA polymers may accelerate their respective celecoxib release. Formulations were prepared by dissolving 2.5 mg PLGA and different amounts (1 mg, 2.5 mg, or 3.5 mg) of celecoxib in 200 µl dichloromethane. 2.5 mg PLGA was comprised of various ratios of PLGA50:50, 0.5 dl/g, acid-terminated, and other PLGA/PDLA polymers. The 200 µl of solution was injected into the center of 50 ml of 1% PVA (w/v) in a 50 ml beaker, stirred at 1,000 rpm with a magnetic stir bar to form an emulsion. The emulsion was stirred at 1,000 rpm for 2 minutes and stirred at about 500 rpm for 2 hours to evaporate the dichloromethane. The microspheres were harvested by centrifugation at 4,000 g for 5 minutes, washed with 50 ml water for three times.

For testing celecoxib release from the microspheres, all prepared microspheres were added to 250 ml of 10 mM PBS and shaken at 80 rpm at 37° C. At each time point in the release study, microspheres were allowed to settle, and an aliquot of 650 µl was taken for measuring UV absorption and added back to the original solution. If the released celecoxib in PBS reached about one third of the fully saturated concentration, 200 ml out of the 250 ml of PBS (without microspheres) was taken out and replaced with fresh 200 ml of PBS. Celecoxib concentration was determined by UV absorption at a wavelength of 230 nm.

Figure 10:
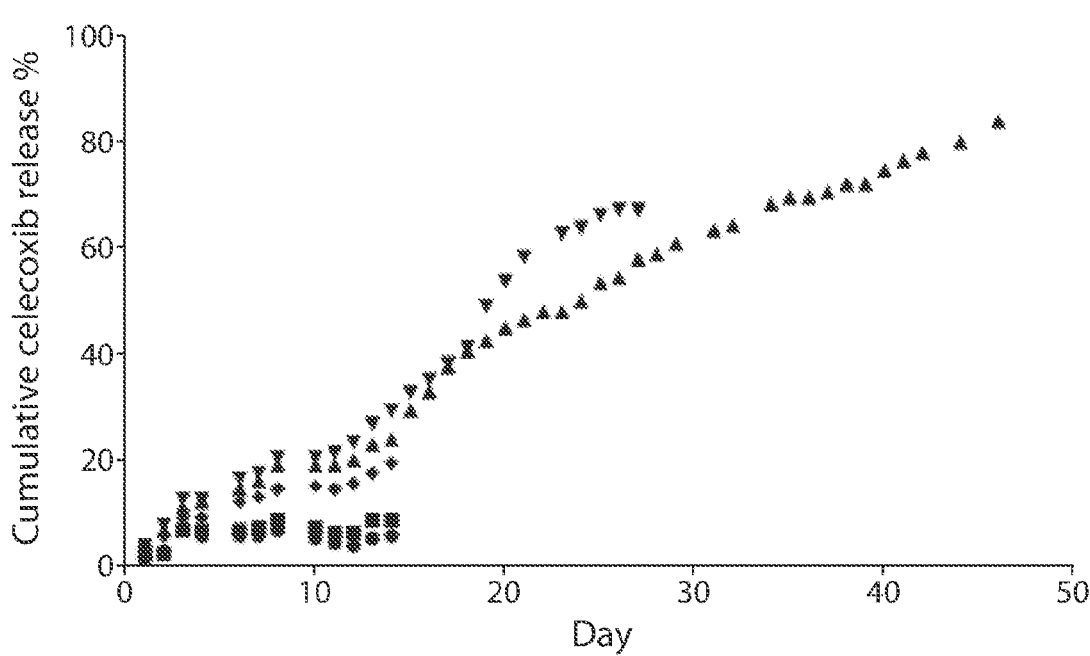

In FIG. 10, 2.5 mg of 50% of PLGA50:50, 0.5 dl/g, acid-terminated, and 50% of PDLA, 0.4 dl/g, ester-terminated, with 1 mg celecoxib loading, resulted in continuous celecoxib release over 45 days.

In FIG. 11, 2.5 mg of PLGA with all ratios of PLGA50:50, 0.5 dl/g, acid-terminated, mixed with PLGA50:50, 0.4 dl/g, ester-terminated, and PLGA50:50, 0.5 dl/g, ester-terminated, resulted in continuous drug release at celecoxib loading of 1 mg.

In FIG. 12, 2.5 mg of PLGA with 2.5 mg celecoxib loading was tested. 25% PDLA, 0.4 dl/g, ester-terminated, with 75% PLGA50:50, 0.5 dl/g, acid-terminated, resulted in continuous celecoxib release over 25 days.

Figure 13:
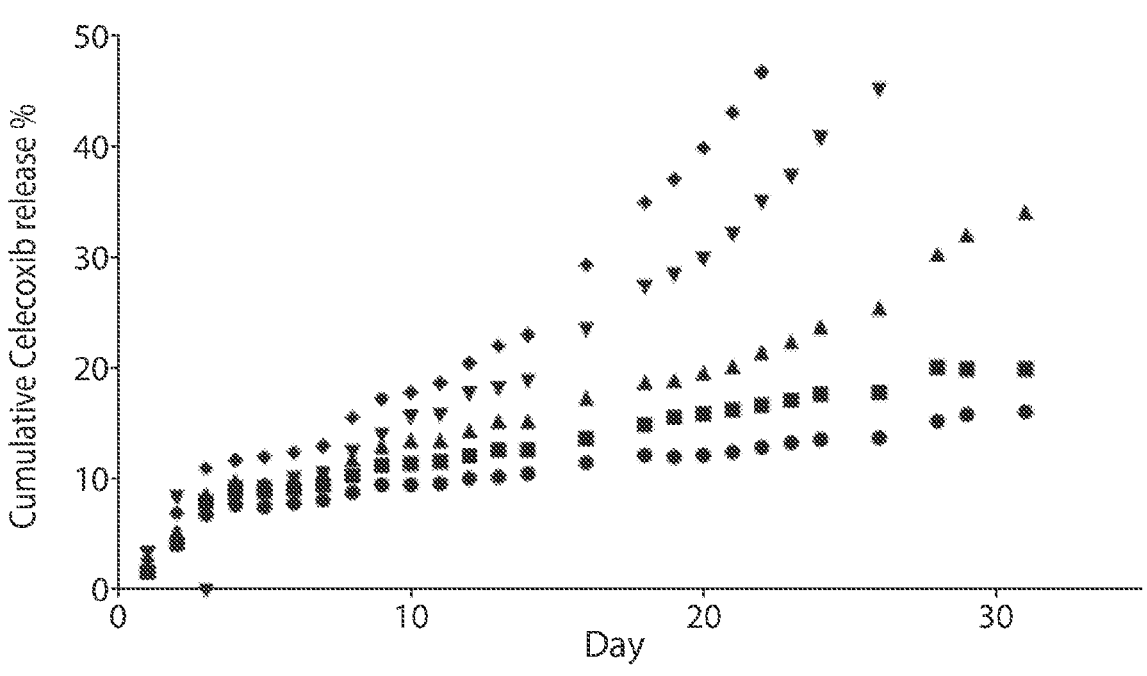

In FIG. 13, 2.5 mg of PLGA with 3.5 mg celecoxib loading was tested. 50-75% of PLGA50:50, 0.5 dl/g, acid-terminated, mixed with PLGA75:25, 0.6 dl/g, ester-terminated, resulted in continuous celecoxib release over 25 days.

Example 9. Microsphere Formulations of Celecoxib: Effects of Poly-Ethylene Glycol (PEG) on Celecoxib Release PEG/PLGA blends are known to allow for more complete and faster release of pharmaceutical agents incorporated into microparticles than PLGA alone (Cleek et al., "Microparticles of poly(DL-lactic-coglycolic acid)/poly(ethylene glycol) blends for controlled drug delivery." *J Control Release* 48(1997):259-268; Morlock, et al., "Erythropoietin loaded microspheres prepared from biodegradable LPLG-PEO-LPLG triblock copolymers: protein stabilization and in vitro release properties." *J Control Release,* 56(1-3) (1998): 105-15; Yeh, "The stability of insulin in biodegradable microparticles based on blends of lactide polymers and polyethylene glycol." *J Microencapsul,* 17(6) (2000): 743-56.).

Formulations were prepared by dissolving 2.5 mg PLGA50:50, 0.5 dl/g, ester-terminated, 2.5 mg of celecoxib, and 0.625 mg, 1.25 mg, or 2.5 mg PEG1450 in 200 μl dichloromethane. The 200 μl of solution was injected into the center of 50 ml of 1% PVA (w/v) in a 50 ml beaker, stirred at 1,000 rpm with a magnetic stir bar to form an emulsion. The emulsion was stirred at 1,000 rpm for 2 minutes and stirred at about 500 rpm for 2 hours to evaporate the dichloromethane. The microspheres were harvested by centrifugation at 4,000 g for 5 minutes, washed with 50 ml water for three times.

For testing celecoxib release from the microspheres, all prepared microspheres were added to 250 ml of 10 mM PBS and shaken at 80 rpm at 37° C. At each time point in the release study, microspheres were allowed to settle, and an aliquot of 650 μl was taken for measuring UV absorption and added back to the original solution. If the released celecoxib in PBS reached about one third of the fully saturated concentration, 200 ml out of the 250 ml of PBS (without microspheres) was taken out and replaced with fresh 200 ml of PBS. Celecoxib concentration was determined by UV absorption at a wavelength of 230 nm.

Figure 14:
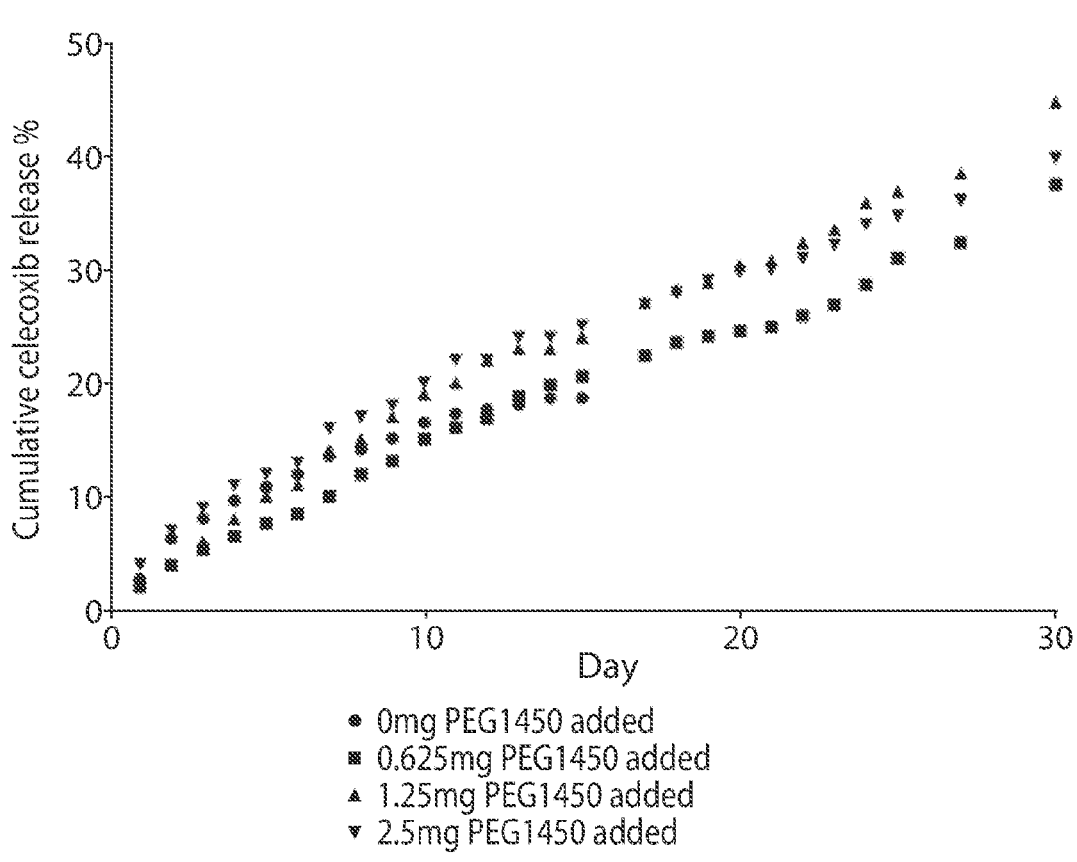

FIG. 14 shows that PEG1450 blending with PLGA slightly increased celecoxib release. With 0 mg of PEG1450, celecoxib release was minimal from day 11 to day 15, whereas all three formulation with PEG1450 blending showed continuous celecoxib release until day 30.

Example 10. Microsphere Formulations of Celecoxib: Microsphere Formulations Based on PLGA75:25, 0.4 dl/q, Acid-Terminated Formulations were prepared by dissolving 2.5 mg PLGA and different amounts (1 mg-5 mg) of celecoxib in 100 μl or 200 μl dichloromethane. The solution was injected into the center of 50 ml of 1% PVA (w/v) in a 50 ml beaker, stirred at 1,000 rpm or 1,200 rpm with a magnetic stir bar to form an emulsion. The emulsion was stirred at 1,000 rpm or 1,200 rpm for 2 minutes and stirred at about 500 rpm for 2 hours to evaporate the dichloromethane. The microspheres were harvested by centrifugation at 4,000 g for 5 minutes, washed with 50 ml water for three times.

For testing celecoxib release from the microspheres, all prepared microspheres were added to 250 ml of 10 mM PBS and shaken at 80 rpm at 37° C. At each time point in the release study, microspheres were allowed to settle, and an aliquot of 650 μl was taken for measuring UV absorption and added back to the original solution. If the released celecoxib in PBS reached about one third of the fully saturated concentration, 200 ml out of the 250 ml of PBS (without microspheres) was taken out and replaced with fresh 200 ml of PBS. Celecoxib concentration was determined by UV absorption at a wavelength of 230 nm.

Figure 15:
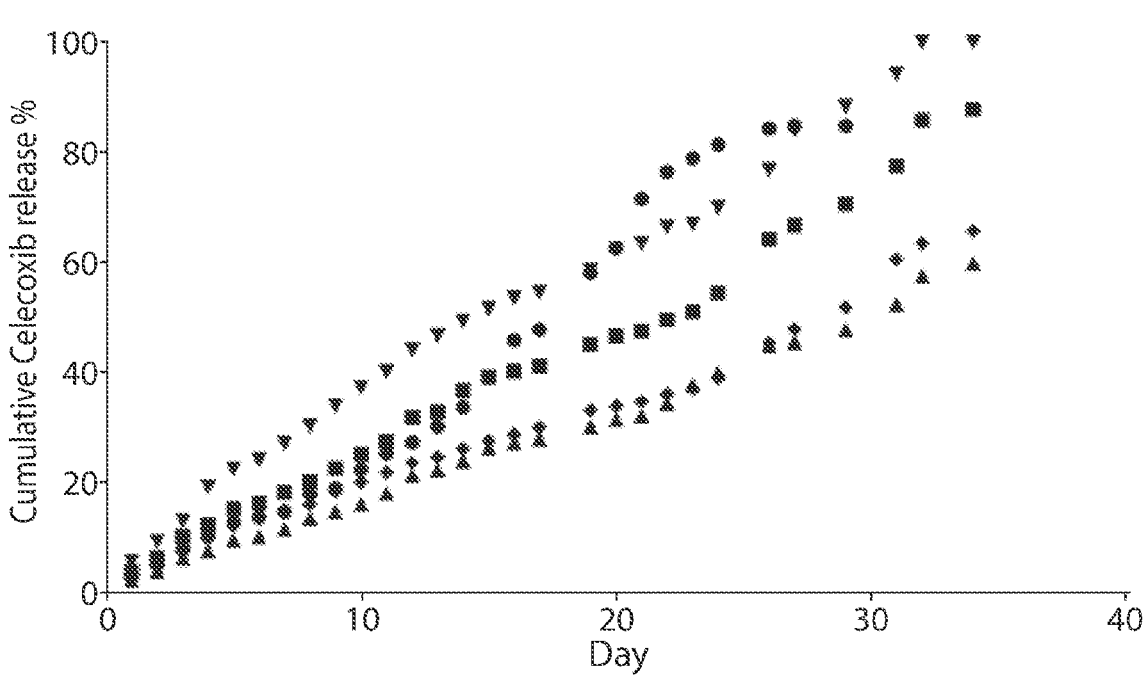

FIG. 15 shows that celecoxib loading of 1-2.5 mg with 2.5 mg PLGA75:25, 0.4 dl/g, acid-terminated, dissolved in 100 μl dichloromethane and stirred at 1,000 rpm, resulted in continuous drug release over 30 days.

Figure 16:
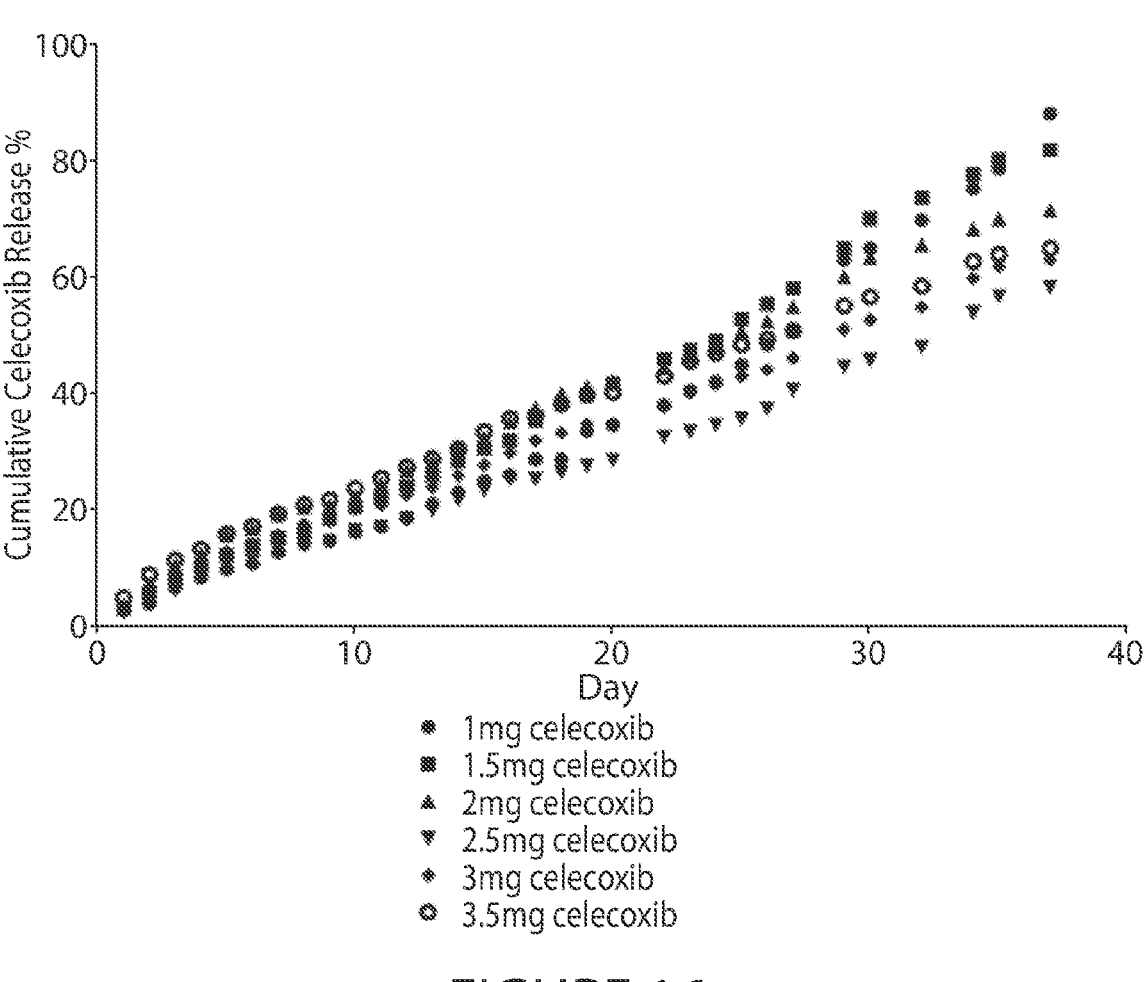

FIG. 16 shows that celecoxib loading of 1-3.5 mg with 2.5 mg PLGA75:25, 0.4 dl/g, acid-terminated, dissolved in 200 μl dichloromethane and stirred at 1,000 rpm, resulted in continuous drug release over 30 days.

Figure 17:
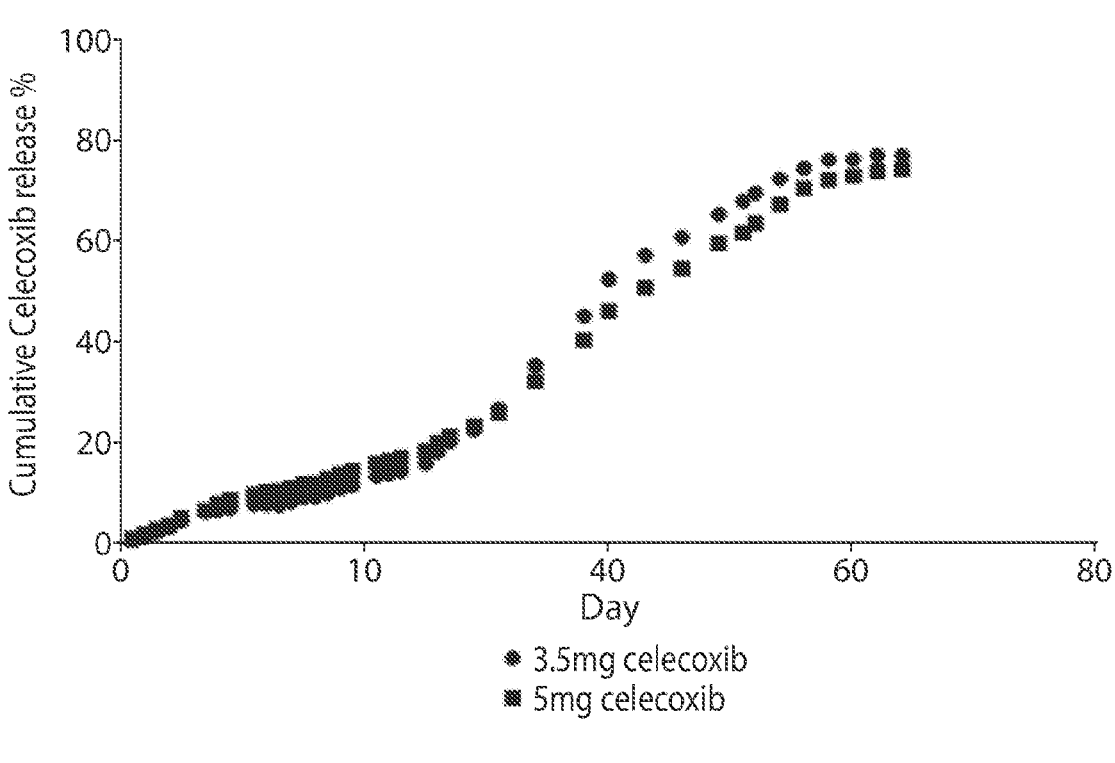

FIG. 17 shows that celecoxib loading of 3.5 mg and 5 mg with 2.5 mg PLGA75:25, 0.4 dl/g, acid-terminated, dissolved in 200 μl dichloromethane and stirred at 1,000 rpm, resulted in continuous drug release over 60 days.

Figure 18:
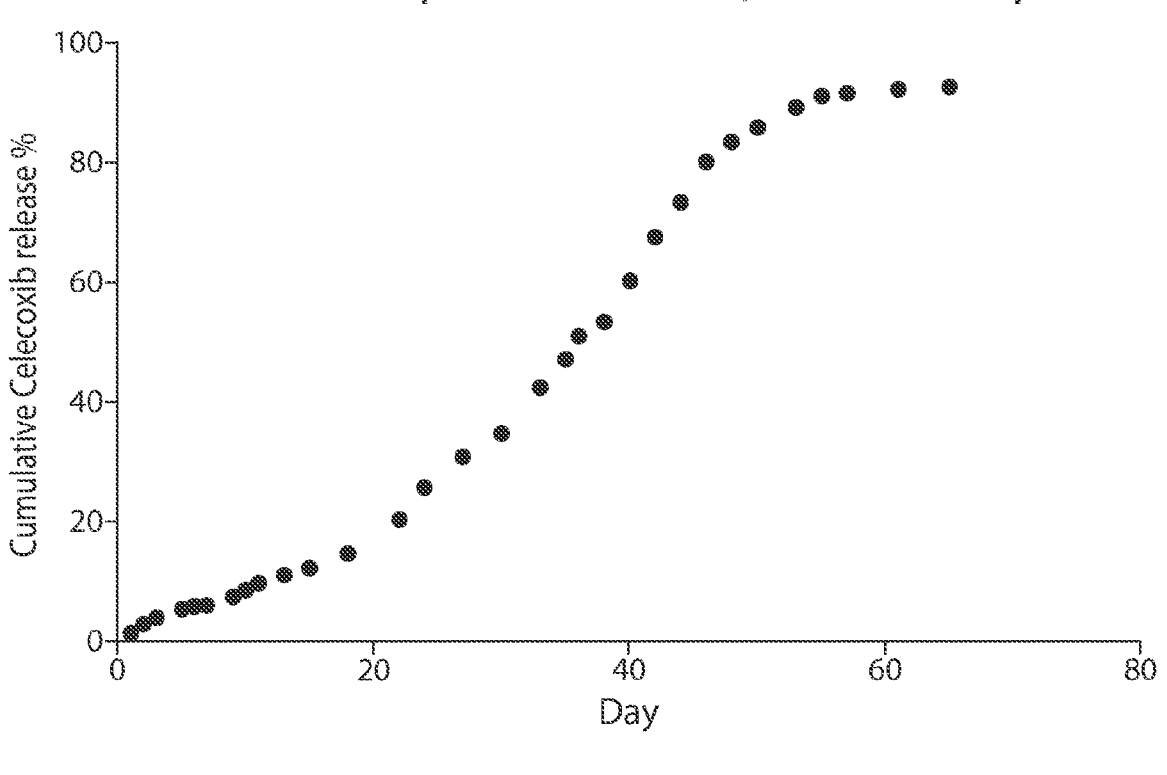

FIG. 18 shows that celecoxib loading of 5 mg and 2.5 mg PLGA75:25, 0.4 dl/g, acid-terminated, dissolved in 200 μl dichloromethane and stirred at 1,200 rpm, resulted in continuous drug release over 60 days.

Figure 19:
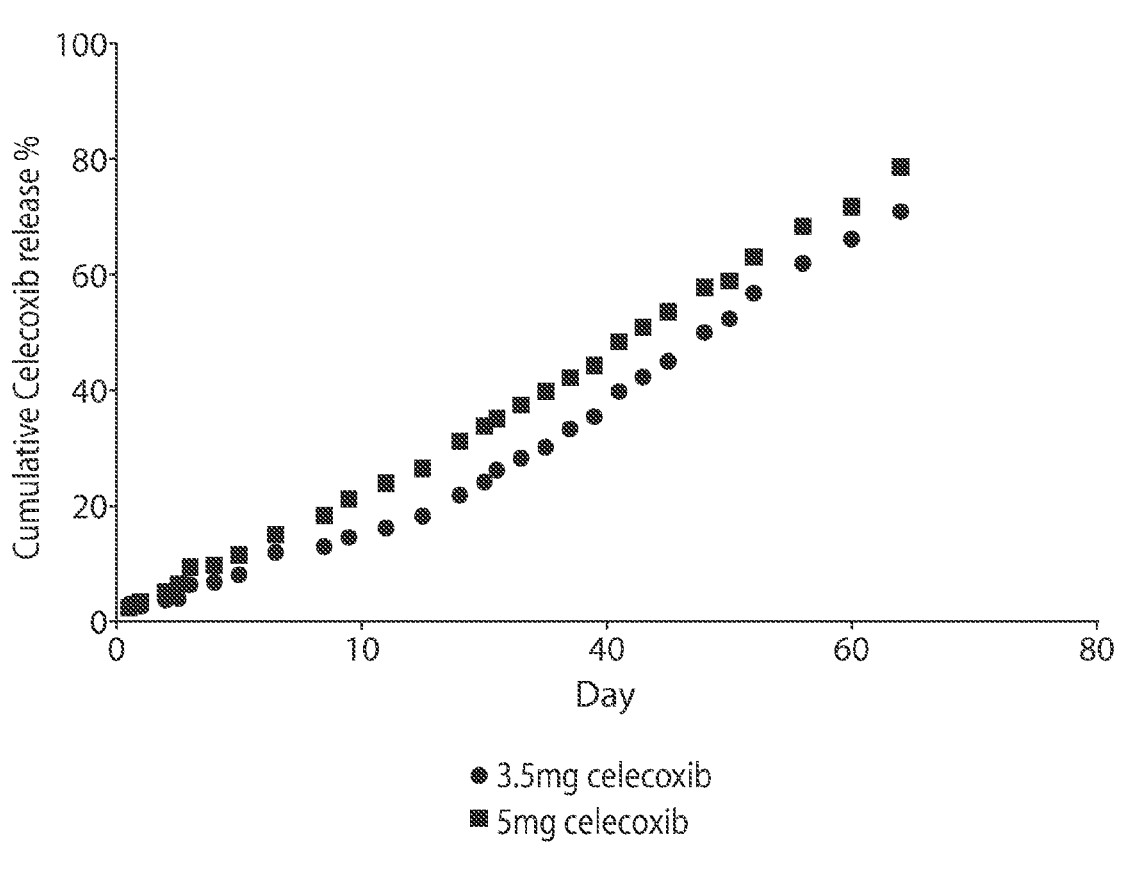

FIG. 19 shows that celecoxib loading of 3.5 mg and 5 mg, and 2.5 mg PLGA75:25, 0.4 dl/g, acid-terminated, dissolved in 200 μl dichloromethane and stirred at 1,200 rpm, resulted in continuous drug release over 60 days.

Example 11. Microsphere Formulations of Celecoxib (I)

Formulations were prepared by dissolving 2.5 mg PLGA and different amounts (4 mg-7.5 mg) of celecoxib in 200 μl dichloromethane. The solution was injected into the center of 50 ml of 1% PVA (w/v) in a 50 ml beaker, stirred at 1,000 rpm with a magnetic stir bar to form an emulsion. The emulsion was stirred at 1,000 rpm for 2 minutes and stirred at about 500 rpm for 2 hours to evaporate the dichloromethane. The microspheres were harvested by centrifugation at 4,000 g for 5 minutes, washed with 50 ml water for three times.

For testing celecoxib release from the microspheres, all prepared microspheres were added to 250 ml of 10 mM PBS and shaken at 80 rpm at 37° C. At each time point in the release study, microspheres were allowed to settle, and an aliquot of 650 μl was taken for measuring UV absorption and added back to the original solution. If the released celecoxib in PBS reached about one third of the fully saturated concentration, 200 ml out of the 250 ml of PBS (without microspheres) was taken out and replaced with fresh 200 ml of PBS. Celecoxib concentration was determined by UV absorption at a wavelength of 230 nm.

Figure 20:
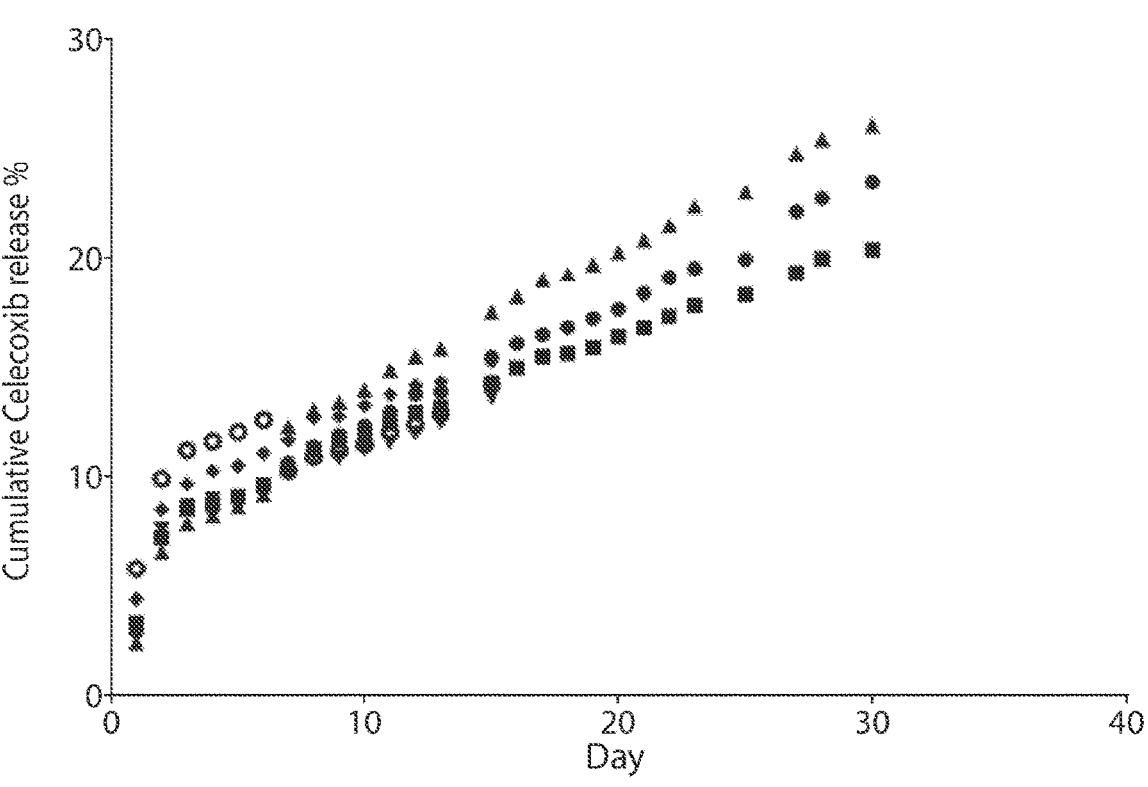

FIG. 20 shows that celecoxib loading at 4 mg, 5 mg, and 6 mg, mixed with PLGA50:50, 0.5 dl/g, ester-terminated, and PLGA50:50, 0.6 dl/g, ester-terminated, dissolved in 200 μl dichloromethane and stirred at 1,000 rpm, resulted in continuous celecoxib release over 30 days.

Figure 21:
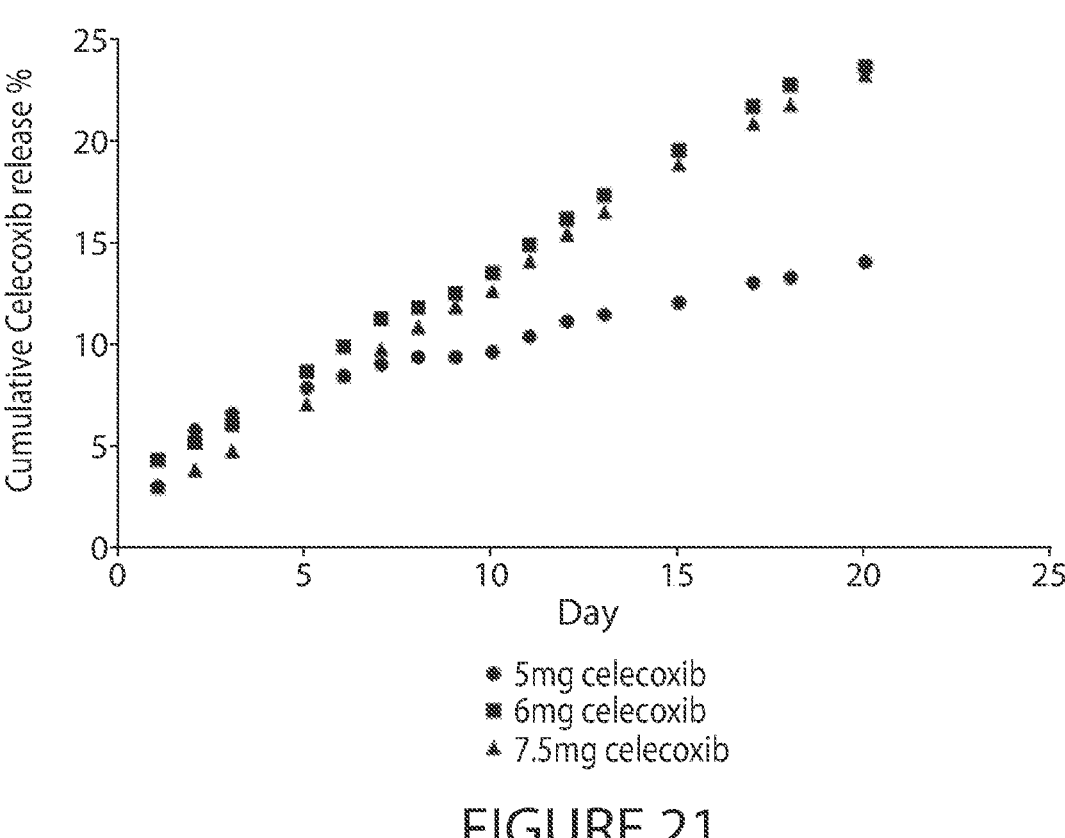

FIG. 21 shows that celecoxib loading at 6 mg and 7.5 mg, mixed with PLGA50:50, 0.5 dl/g, ester-terminated, dissolved in 200 μl dichloromethane and stirred at 1,000 rpm, resulted in continuous celecoxib release over 20 days.

Figure 22:
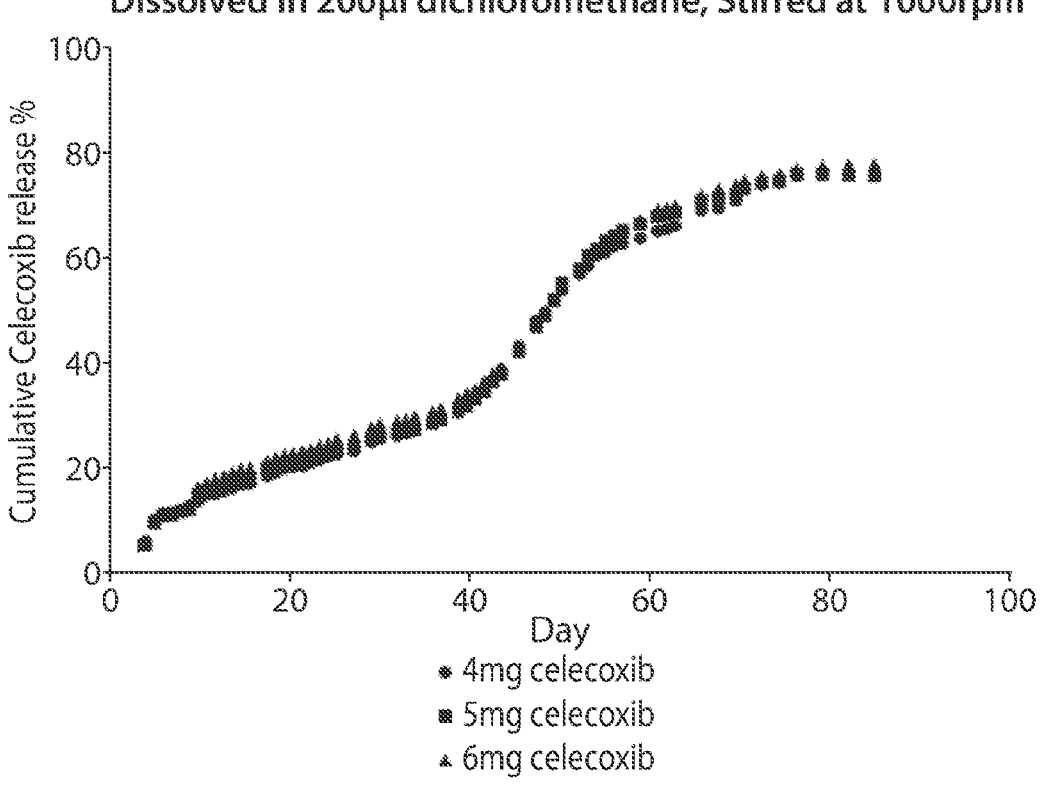

FIG. 22 shows that celecoxib loading at 4 mg, 5 mg, and 6 mg, mixed with PLGA50:50, 0.7 dl/g, ester-terminated, dissolved in 200 μl dichloromethane and stirred at 1,000 rpm, resulted in continuous celecoxib release over 70 days. Unexpectedly, increased loading ratio did not result in higher release rate.

Example 12. Microsphere Formulations of Celecoxib (II)

Formulations were prepared by dissolving 2.5 mg PLGA and different amounts (4 mg-7.5 mg) of celecoxib in 200 μl-400 μl dichloromethane. The solution was injected into the center of 50 ml of 1% PVA (w/v) in a 50 ml beaker, stirred at 1,000 rpm with a magnetic stir bar to form an emulsion. The emulsion was stirred at 1,000 rpm for 2 minutes and stirred at about 500 rpm for 2 hours to evaporate the dichloromethane. The microspheres were harvested by centrifugation at 4,000 g for 5 minutes, washed with 50 ml water for three times.

For testing celecoxib release from the microspheres, all prepared microspheres were added to 250 ml of 10 mM PBS and shaken at 80 rpm at 37° C. At each time point in the release study, microspheres were allowed to settle, and an aliquot of 650 µl was taken for measuring UV absorption and added back to the original solution. If the released celecoxib in PBS reached about one third of the fully saturated concentration, 200 ml out of the 250 ml of PBS (without microspheres) was taken out and replaced with fresh 200 ml of PBS. Celecoxib concentration was determined by UV absorption at a wavelength of 230 nm.

Figure 23:
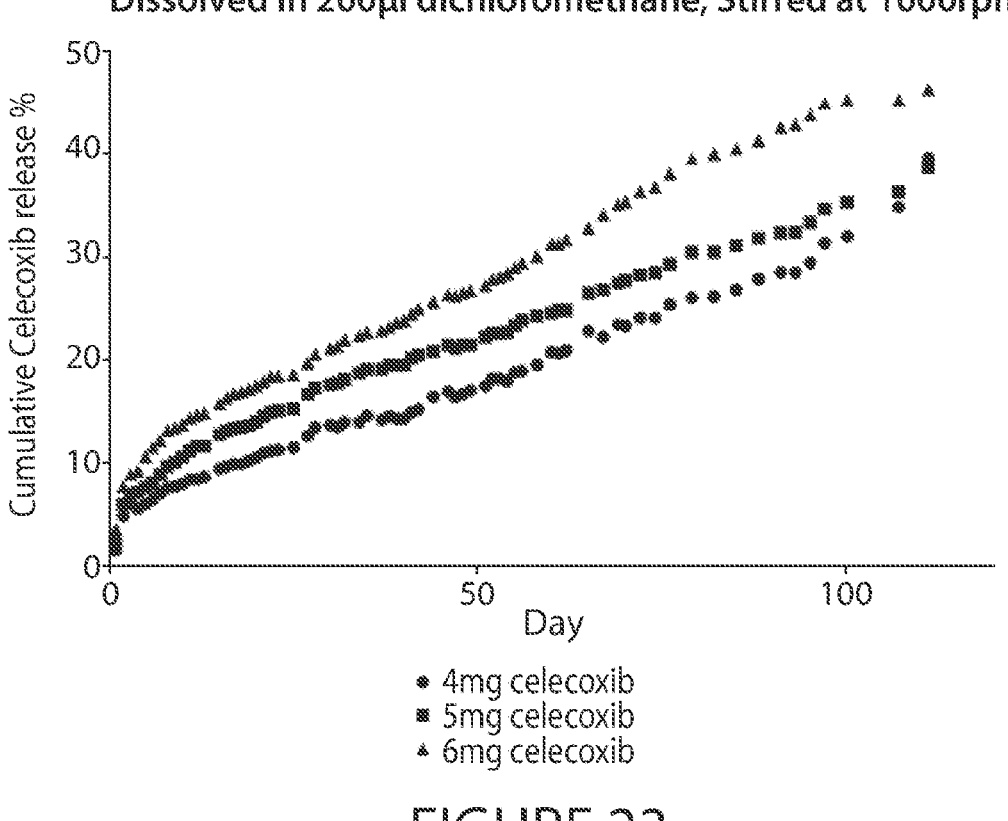

FIG. 23 shows that celecoxib loading at 4 mg, 5 mg, and 6 mg, mixed with 2.5 mg PLGA75:25, 0.6 dl/g, ester-terminated, dissolved in 200 µl dichloromethane and stirred at 1,000 rpm, resulted in continuous celecoxib release over 111 days. Higher celecoxib loading was associated with faster drug release.

Figure 24:
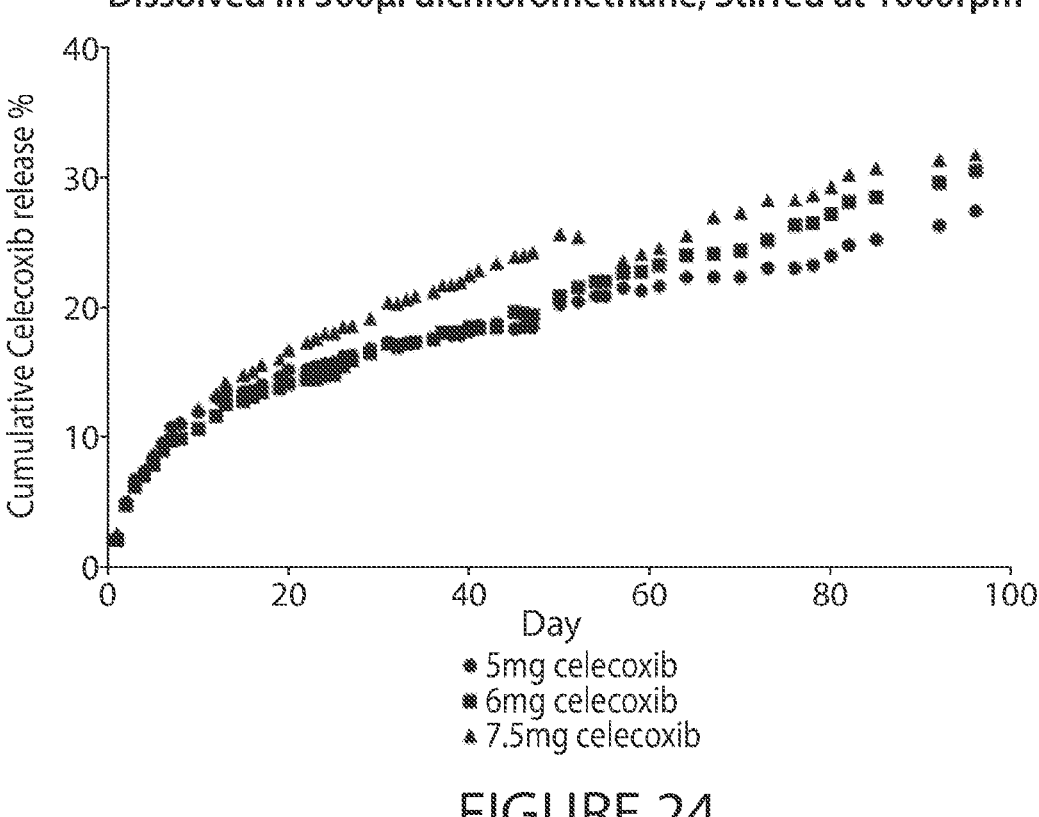

FIG. 24 shows that celecoxib loading at 5 mg, 6 mg, and 7.5 mg, mixed with 2.5 mg PLGA75:25, 0.6 dl/g, ester-terminated, dissolved in 300 µl dichloromethane and stirred at 1,000 rpm, resulted in continuous celecoxib release over 92 days. Higher celecoxib loading was associated with faster drug release.

Figure 25:
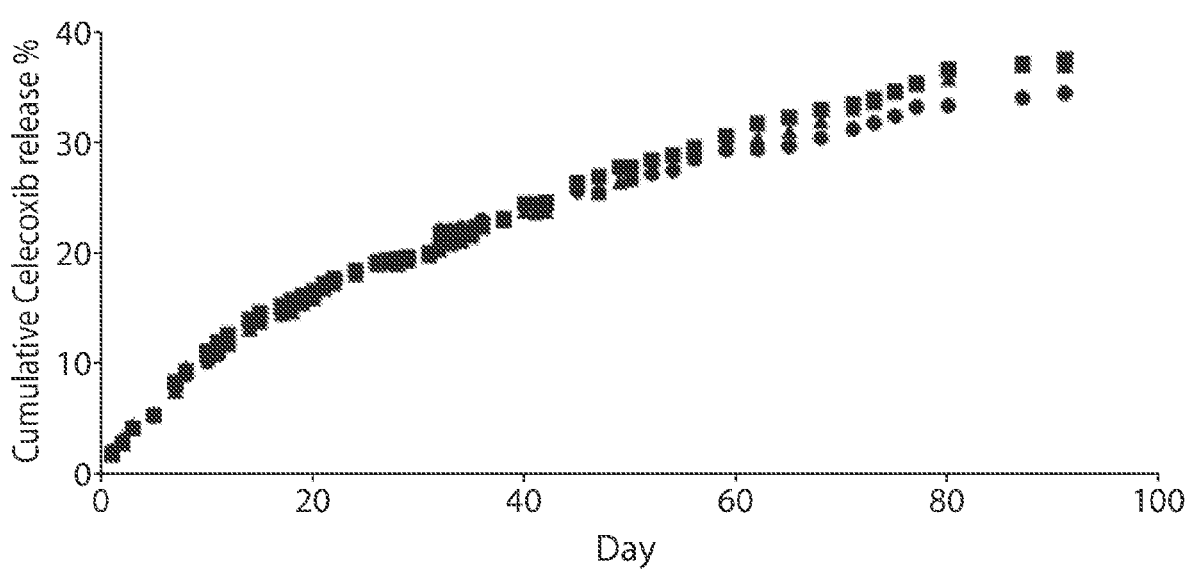

FIG. 25 shows that celecoxib loading at 5 mg and 6 mg, mixed with 2.5 mg PLGA75:25, 0.6 dl/g, ester-terminated, dissolved in 300 µl or 400 µl and stirred at 1,000 rpm, resulted in continuous celecoxib release over 90 days.

Example 13. Microsphere Formulations of Celecoxib (III)

Formulations were prepared by dissolving 2.5 mg PLGA and different amounts (5 mg-7.5 mg) of celecoxib in 300 µl or 400 µl dichloromethane. The solution was injected into the center of 50 ml of 1% PVA (w/v) in a 50 ml beaker, stirred at 1,000 rpm with a magnetic stir bar to form an emulsion. The emulsion was stirred at 1,000 rpm for 2 minutes and stirred at about 500 rpm for 2 hours to evaporate the dichloromethane. The microspheres were harvested by centrifugation at 4,000 g for 5 minutes, washed with 50 ml water for three times.

For testing celecoxib release from the microspheres, all prepared microspheres were added to 250 ml of 10 mM PBS and shaken at 80 rpm at 37° C. At each time point in the release study, microspheres were allowed to settle, and an aliquot of 650 µl was taken for measuring UV absorption and added back to the original solution. If the released celecoxib in PBS reached about one third of the fully saturated concentration, 200 ml out of the 250 ml of PBS (without microspheres) was taken out and replaced with fresh 200 ml of PBS. Celecoxib concentration was determined by UV absorption at a wavelength of 230 nm.

Figure 26:
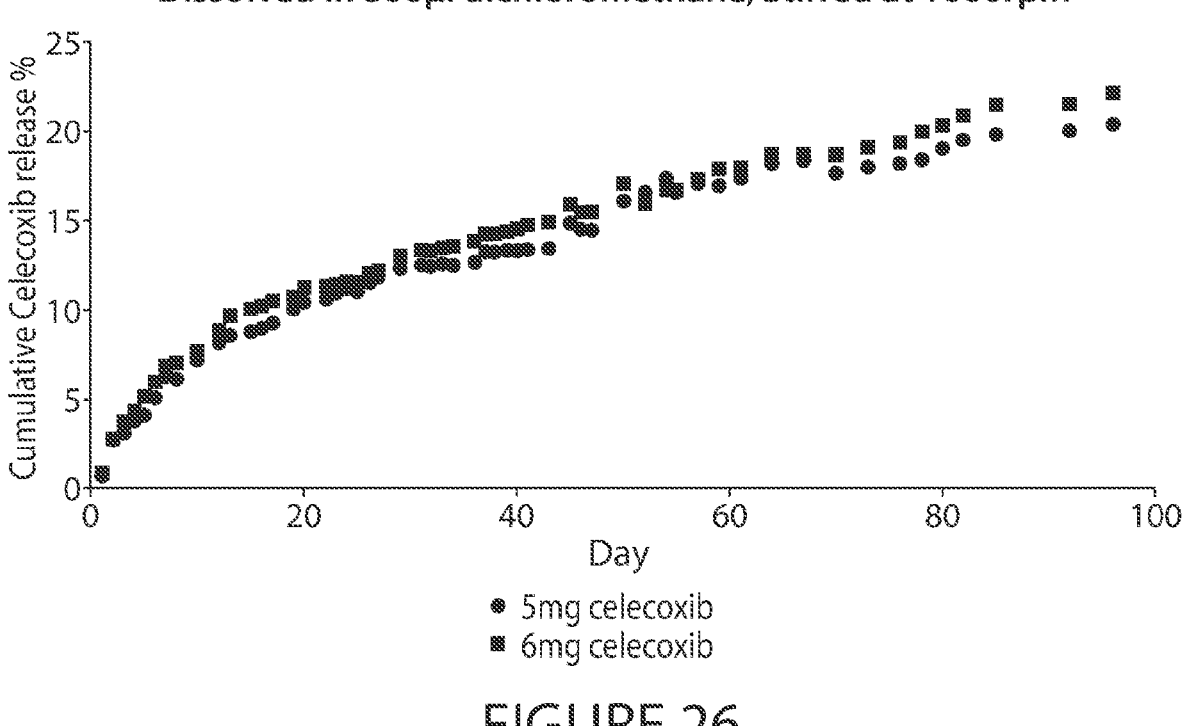
Figure 27:
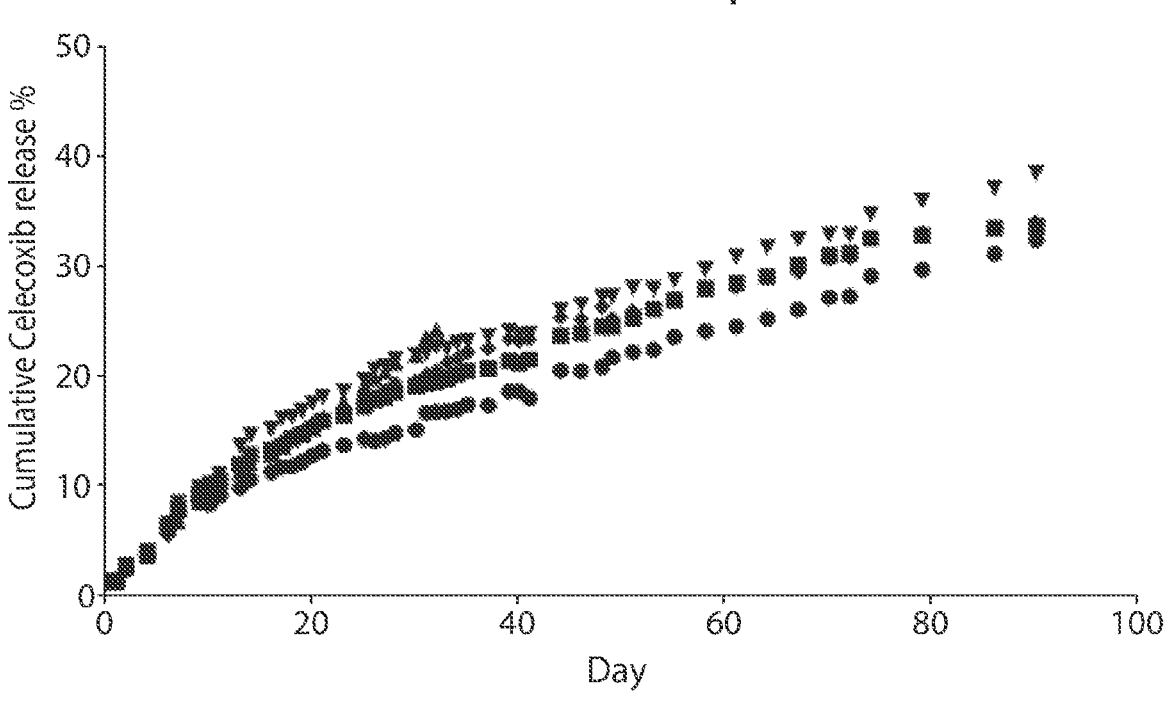
Figure 28:
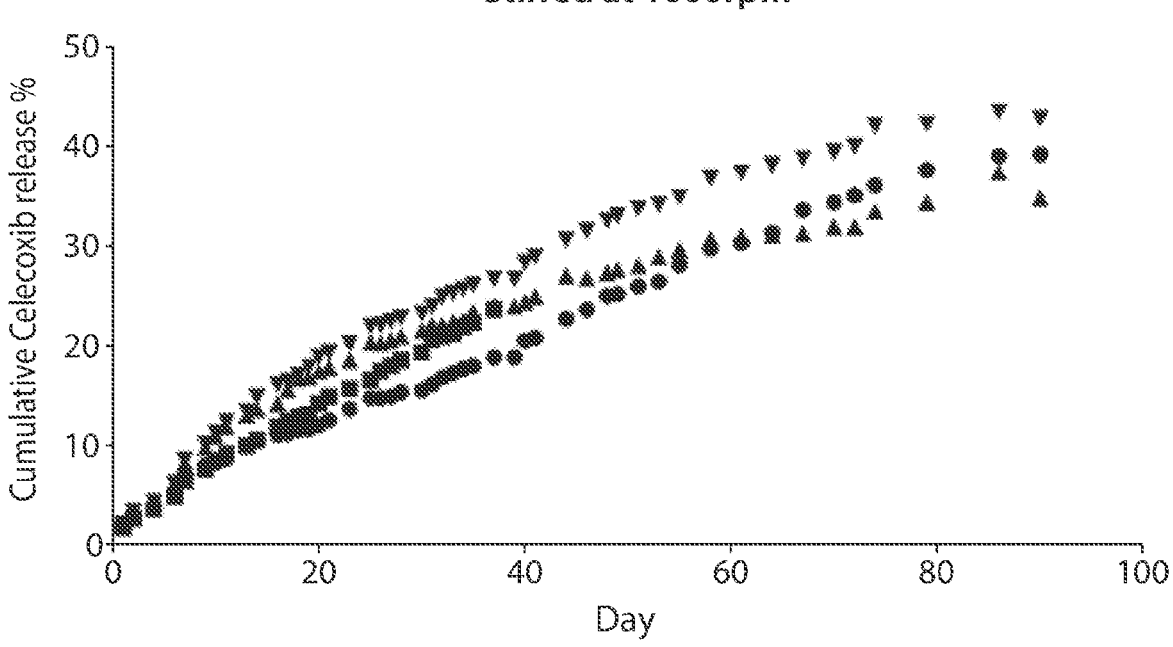
Figure 29:
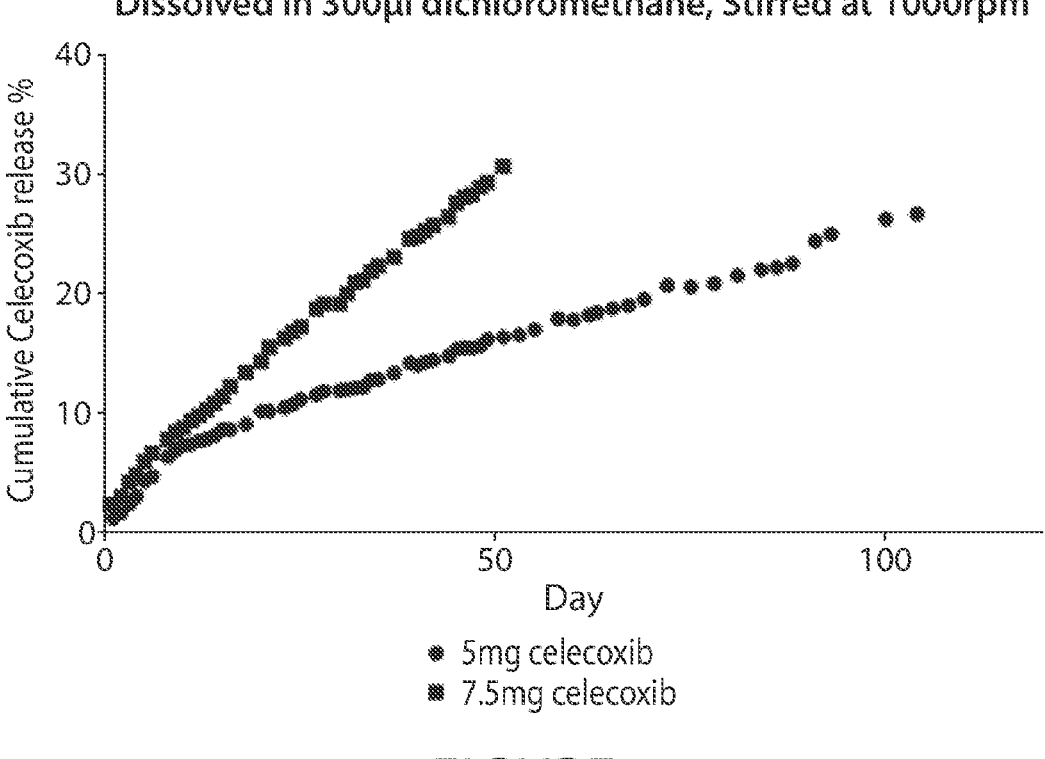
Figure 30:
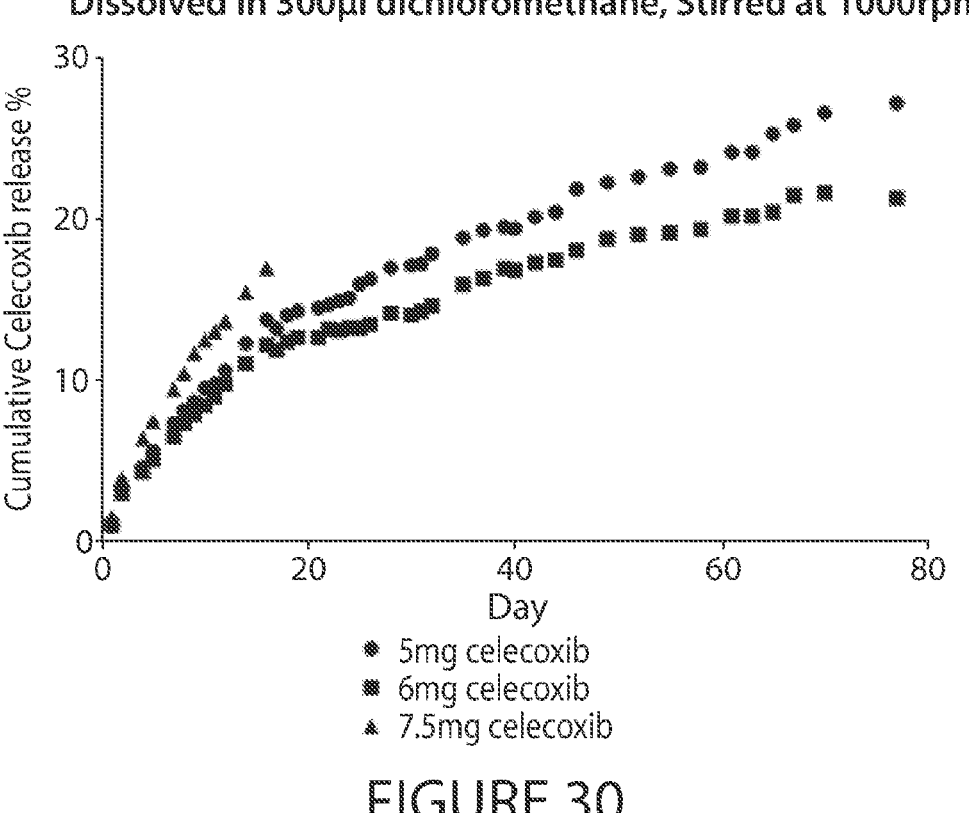

FIG. 26 shows celecoxib loading of 5 mg and 6 mg, mixed with 2.5 mg PLGA75:25, 0.9 dl/g, ester-terminated, dissolved in 300 µl dichloromethane and stirred at 1,000 rpm, resulted in continuous celecoxib release over 90 days.

FIGS. 27, 28, 29, and 30 show that celecoxib loading of 5 mg, 6 mg, and 7.5 mg, mixed with PLGA75:25, 0.9 dl/g, ester-terminated, dissolved in 300 µl or 400 µl dichloromethane and stirred at 1,000 rpm, resulted in continuous celecoxib release over 80 days.

Figure 31:
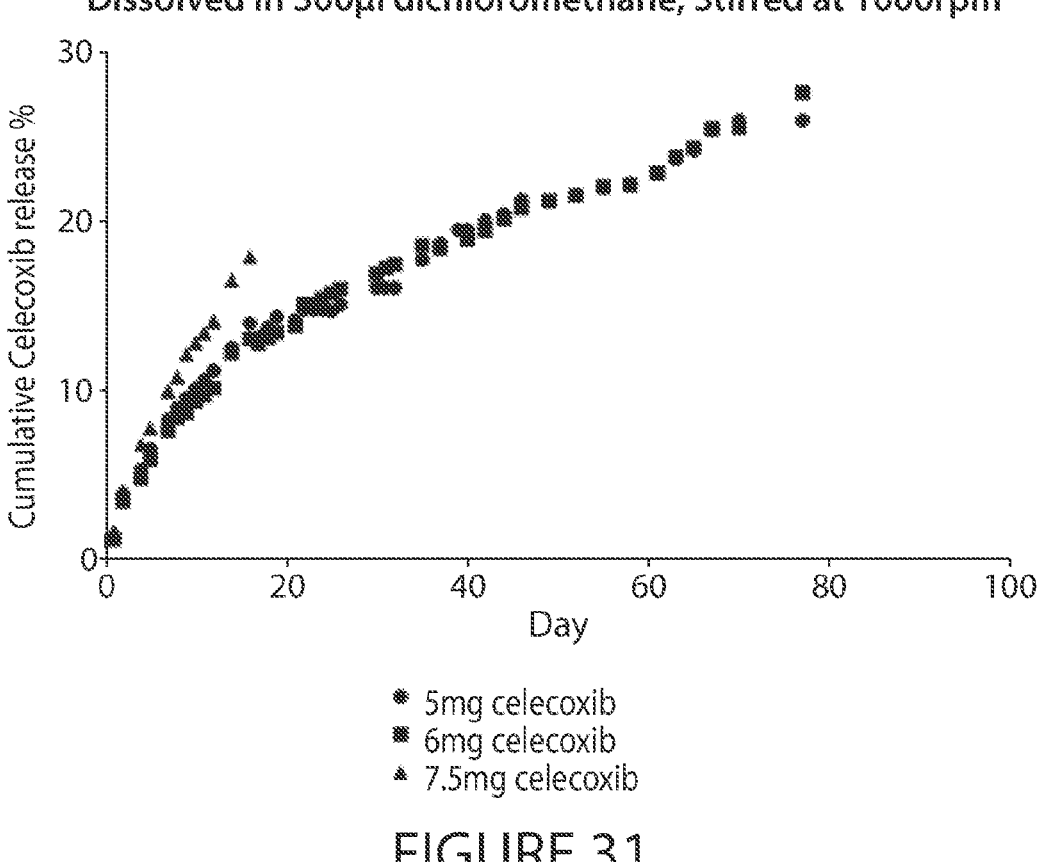

FIG. 31 shows that celecoxib loading of 5 mg and 6 mg, mixed with PLGA75:25, 1.2 dl/g, ester-terminated, dissolved in 300 µl dichloromethane and stirred at 1,000 rpm, resulted in continuous celecoxib release over 70 days.

Example 14. Microsphere Formulations of Celecoxib (IV)

Formulations were prepared by dissolving 2.5 mg PLGA or PDLA and different amounts (5 mg-7.5 mg) of celecoxib in 200 µl, 300 µl or 400 µl dichloromethane. The solution was injected into the center of 50 ml of 1% PVA (w/v) in a 50 ml beaker, stirred at 1,000 rpm with a magnetic stir bar for 2 minutes to form an emulsion. The emulsion was stirred at about 500 rpm for 2 hours to evaporate the dichloromethane. The microspheres were harvested by centrifugation at 4,000 g for 5 minutes, washed with 50 ml water for three times.

For testing celecoxib release from the microspheres, all prepared microspheres were added to 250 ml of 10 mM PBS and shaken at 80 rpm at 37° C. At each time point in the release study, microspheres were allowed to settle, and an aliquot of 650 µl was taken for measuring UV absorption and added back to the original solution. If the released celecoxib in PBS reached about one third of the fully saturated concentration, 200 ml out of the 250 ml of PBS (without microspheres) was taken out and replaced with fresh 200 ml of PBS. Celecoxib concentration was determined by UV absorption at a wavelength of 230 nm.

Figure 32:
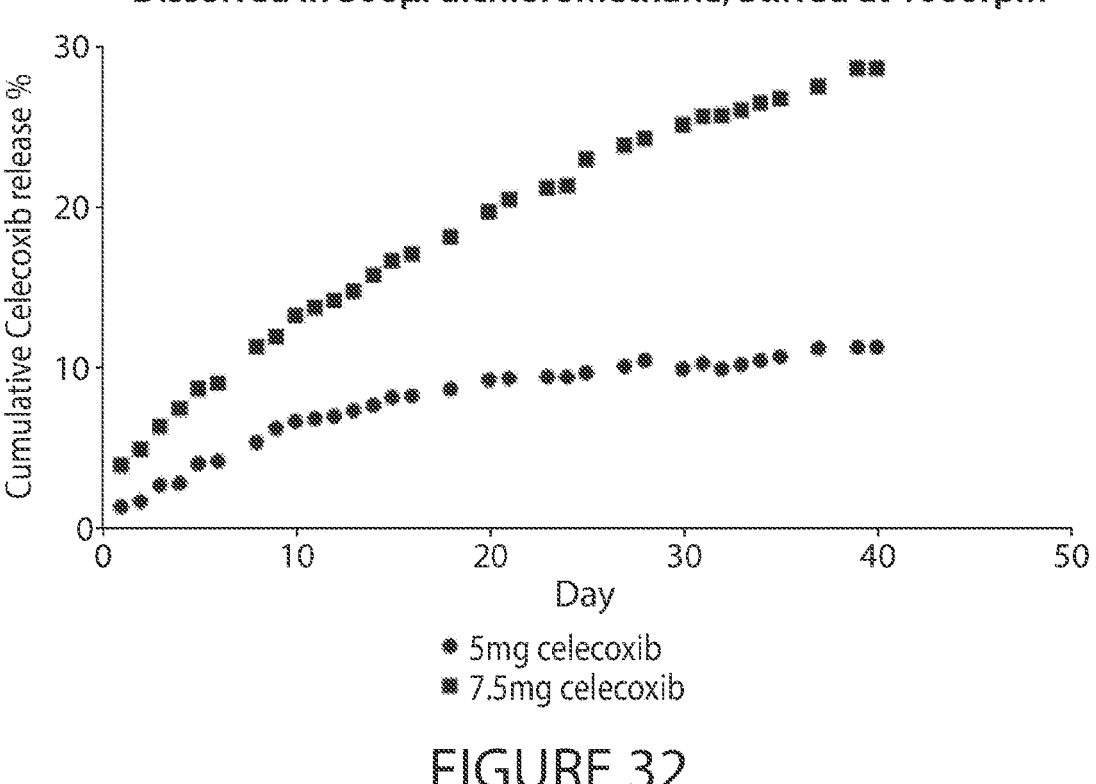

FIG. 32 shows that 7.5 mg of celecoxib, mixed with 2.5 mg PLGA85:15, 0.6 dl/g, ester-terminated, dissolved in 300 µl dichloromethane and stirred at 1,000 rpm, resulted in continuous celecoxib release over 40 days.

Figure 33:
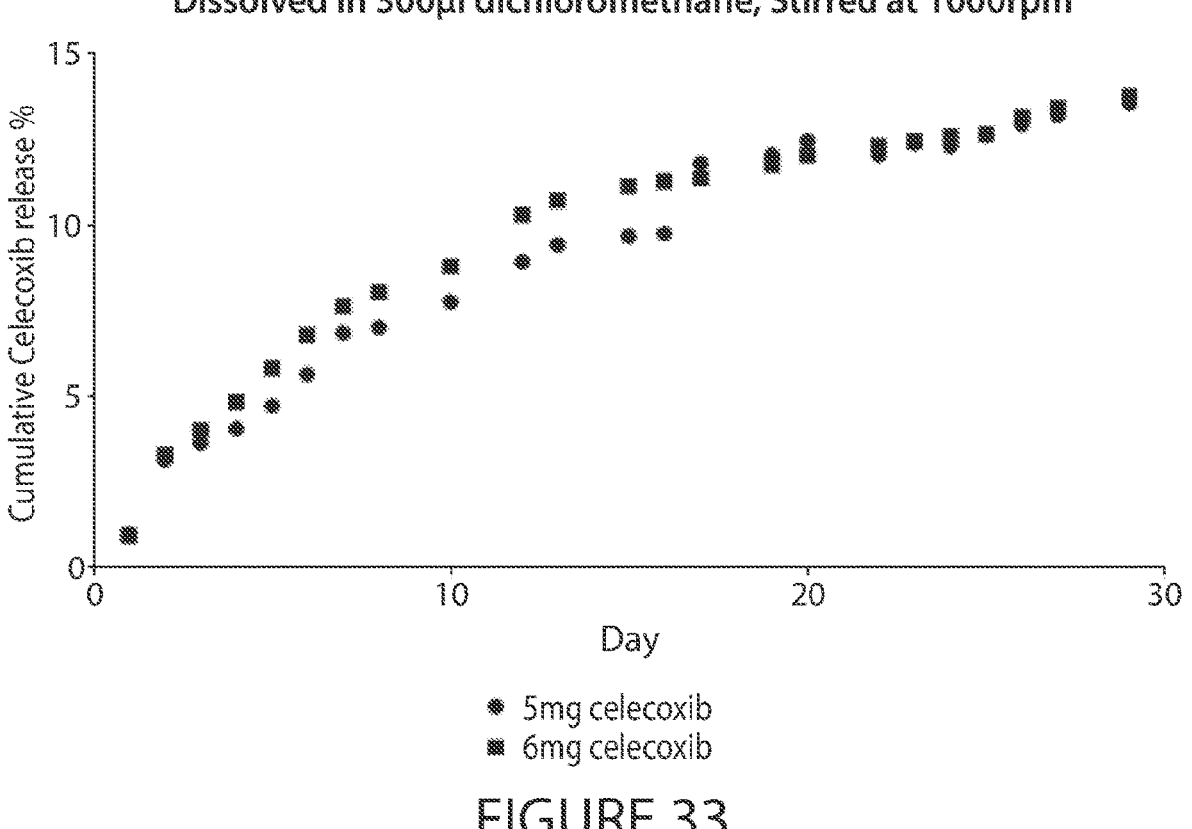

FIG. 33 shows that 6 mg of celecoxib, mixed with 2.5 mg PLGA85:15, 0.6 dl/g, ester-terminated, dissolved in 300 µl dichloromethane and stirred at 1,000 rpm, resulted in continuous celecoxib release over about 30 days.

Figure 34:
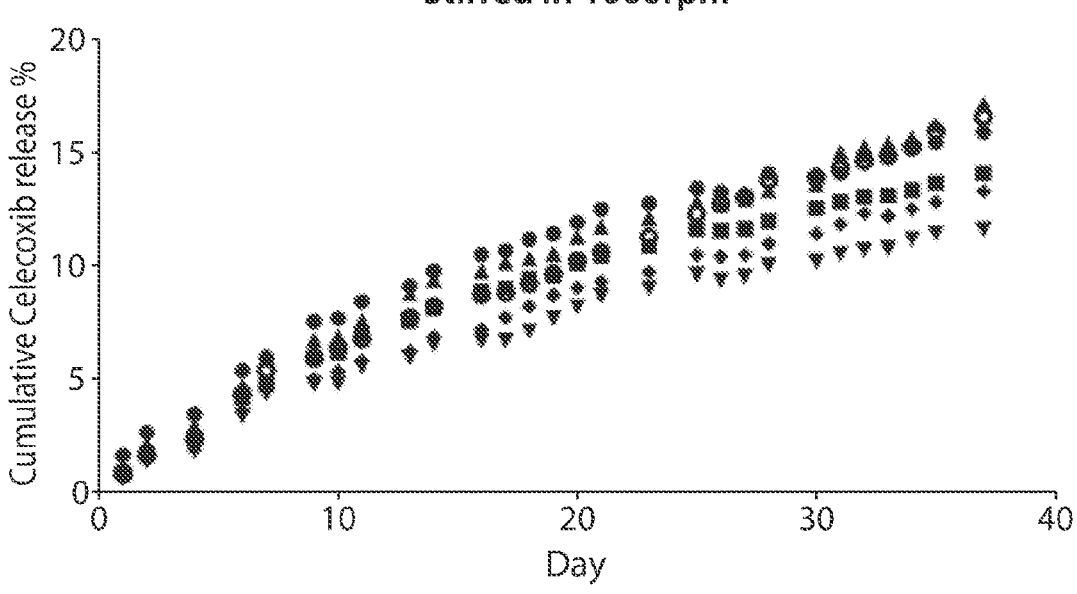

FIG. 34 shows that celecoxib loading of 7.5 mg, mixed with 2.5 mg of PLGA85:15, 1.5 dl/g, ester-terminated, dissolved in 300 µl or 400 µl dichloromethane and stirred at 1,000 rpm, resulted in continuous celecoxib release over 35 days.

Figure 35:
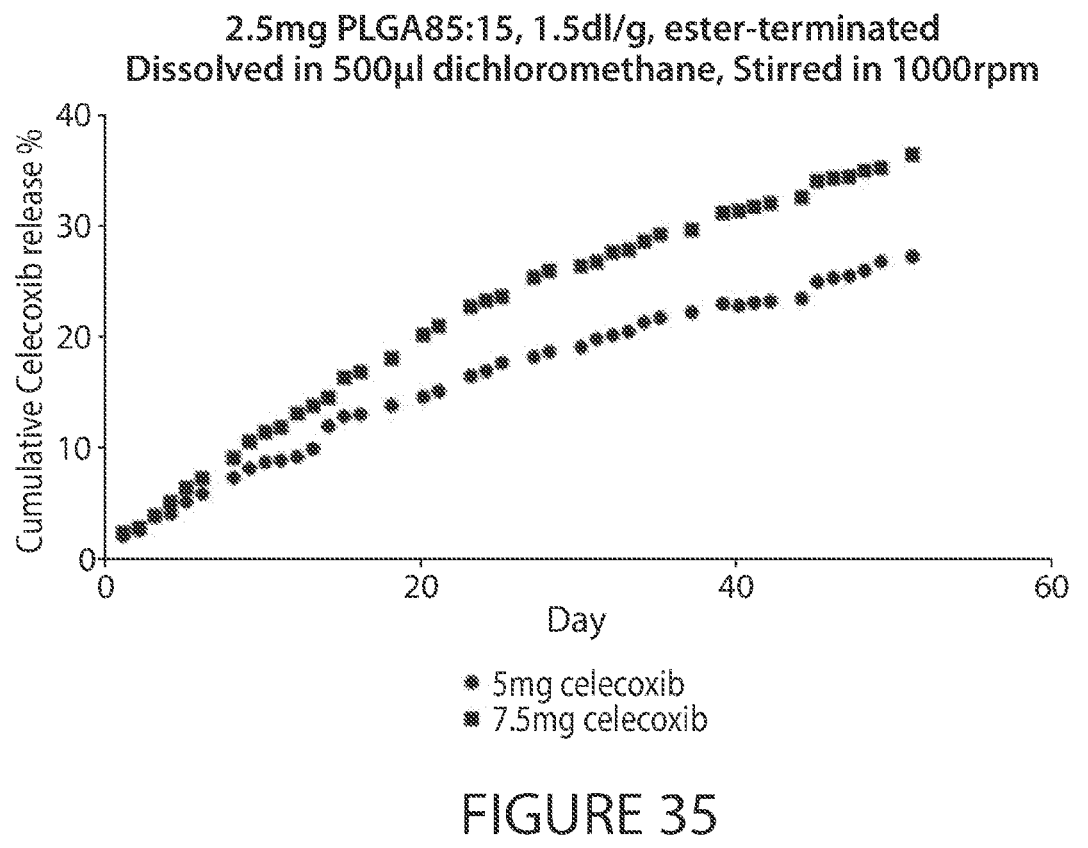

FIG. 35 shows that celecoxib loading of 5 mg and 7.5 mg, mixed with 2.5 mg of PLGA85:15, 1.5 dl/g, ester-terminated, dissolved in 500 µl dichloromethane and stirred at 1,000 rpm, resulted in continuous celecoxib release over 50 days.

Figure 36:
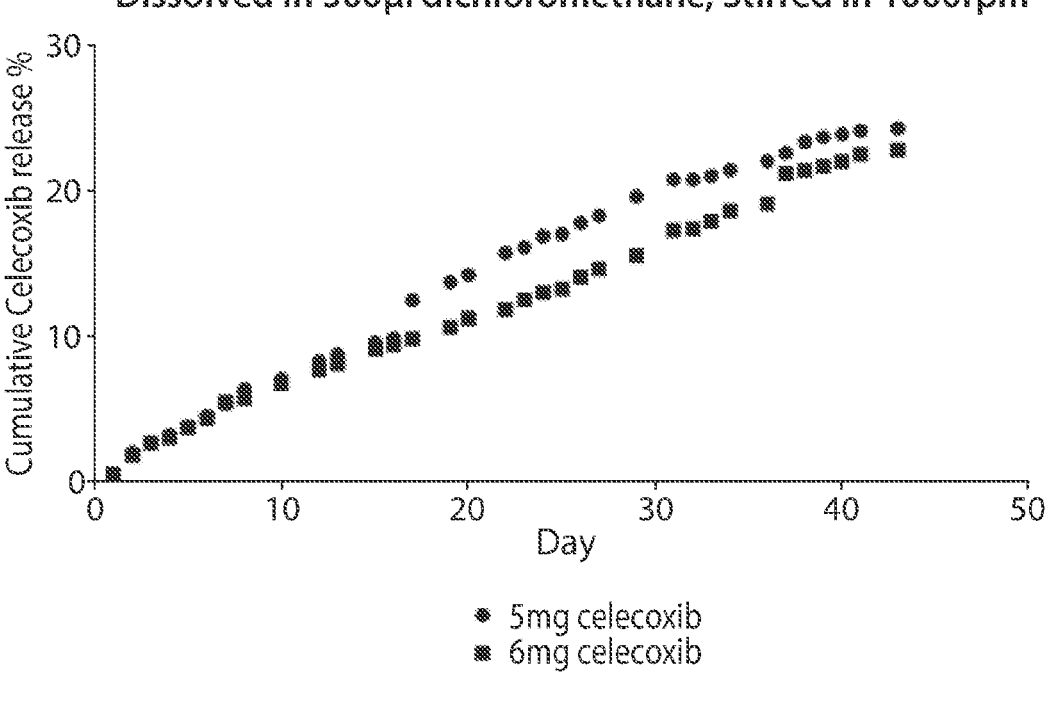

FIG. 36 shows that celecoxib loading of 5 mg and 6 mg, mixed with 2.5 mg PDLA, 0.6 dl/g, ester-terminated, dissolved in 300 µl dichloromethane and stirred at 1,000 rpm, resulted in continuous celecoxib release over 40 days.

Figure 37:
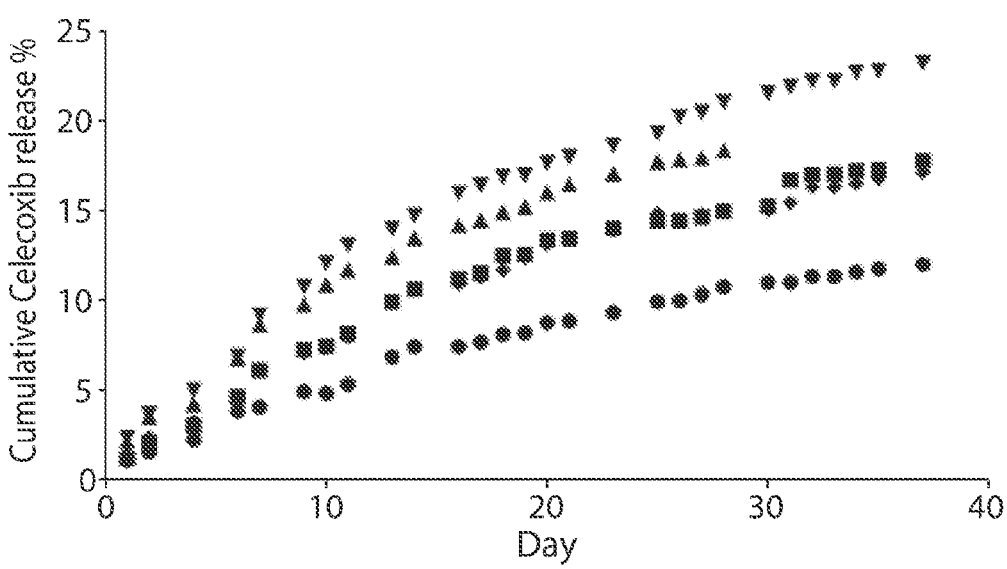

FIG. 37 shows that celecoxib loading of 5 mg and 6 mg, mixed with 2.5 mg PDLA, 0.6 dl/g, ester-terminated, dissolved in 300 µl or 400 µl dichloromethane and stirred at 1,000 rpm, resulted in continuous celecoxib release over 35 days.

Figure 38:
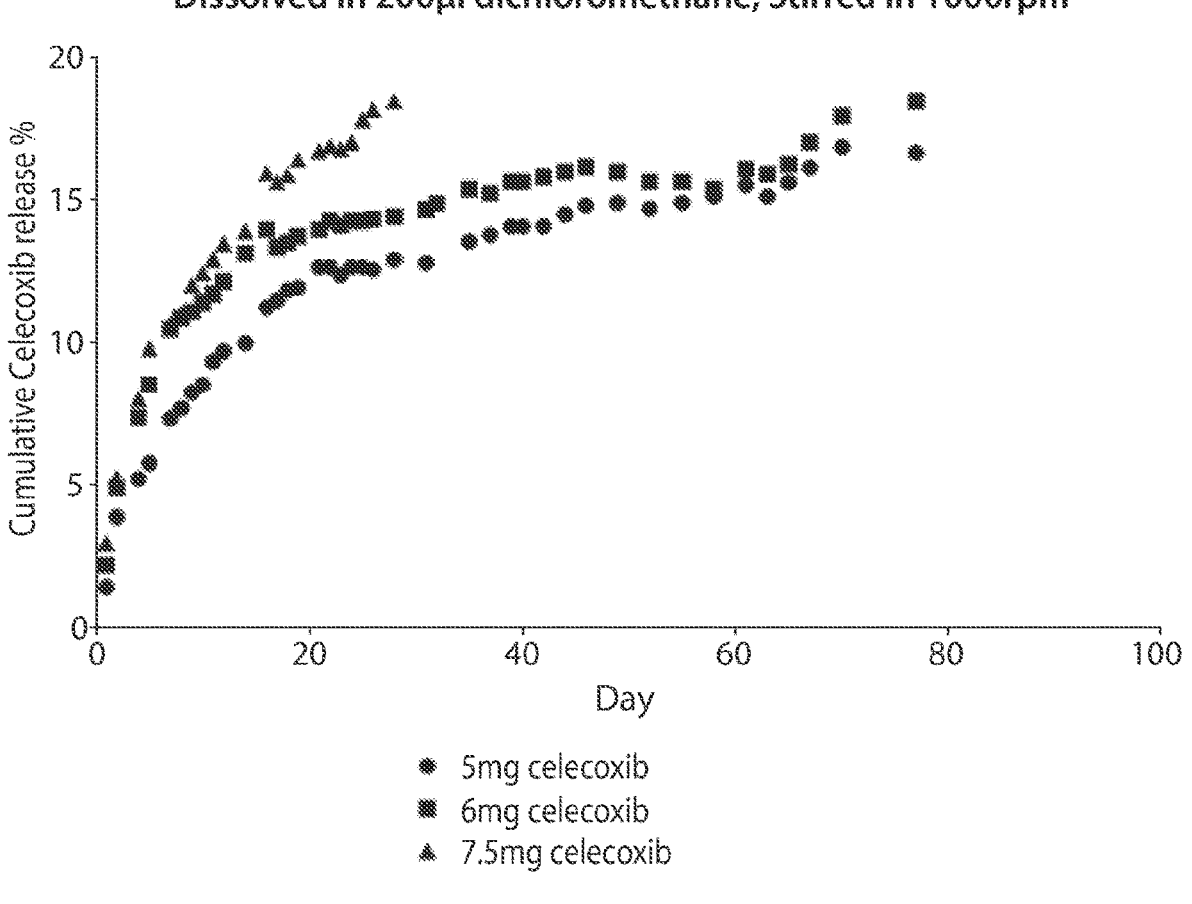

FIG. 38 shows that celecoxib loading of 5 mg and 6 mg, mixed with 2.5 mg PDLA, 0.4 dl/g, ester-terminated, dissolved in 200 µl dichloromethane and stirred at 1,000 rpm, resulted in little celecoxib release from day 20 to day 30 and from day 50 to day 60, which is unsuitable for continuous celecoxib release over multiple months.

Example 15. Microsphere Formulations of Celecoxib: Effects of Mixed PLGA Compositions on Celecoxib Release Formulations were prepared by dissolving 2.5 mg PLGA (comprising of different proportions of mixed polymers) and different amounts (3.5 mg-5 mg) of celecoxib in 200 μl or 300 μl dichloromethane. The solution was injected into the center of 50 ml of 1% PVA (w/v) in a 50 ml beaker, stirred at 1,000 rpm or 1,200 rpm with a magnetic stir bar to form an emulsion. The emulsion was stirred at 1,000 rpm or 1,200 rpm for 2 minutes and stirred at about 500 rpm for 2 hours to evaporate the dichloromethane. The microspheres were harvested by centrifugation at 4,000 g for 5 minutes, washed with 50 ml water for three times.

For testing celecoxib release from the microspheres, all prepared microspheres were added to 250 ml of 10 mM PBS and shaken at 80 rpm at 37° C. At each time point in the release study, microspheres were allowed to settle, and an aliquot of 650 μl was taken for measuring UV absorption and added back to the original solution. If the released celecoxib in PBS reached about one third of the fully saturated concentration, 200 ml out of the 250 ml of PBS (without microspheres) was taken out and replaced with fresh 200 ml of PBS. Celecoxib concentration was determined by UV absorption at a wavelength of 230 nm.

Figure 39:
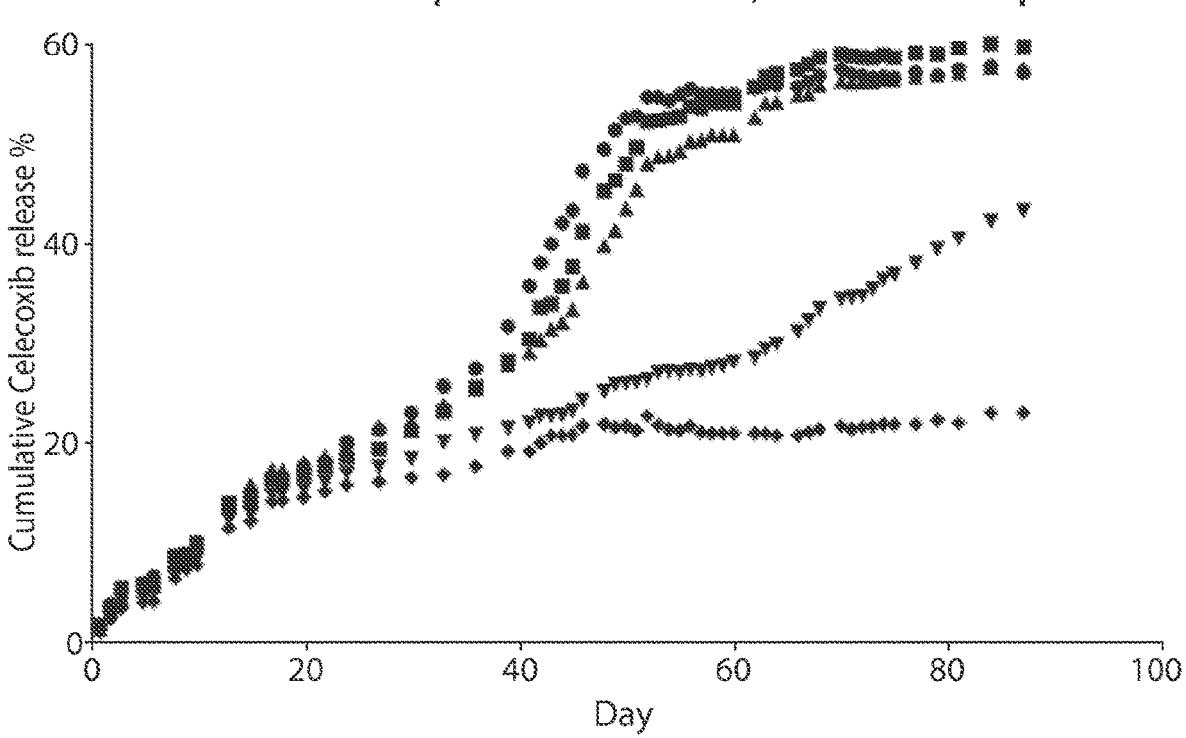

FIG. 39 shows that mixing PLGA50:50, 0.7 dl/g, ester-terminated, with PLGA75:25, 0.6 dl/g, ester-terminated, slowed down celecoxib release and prolonged duration of continuous drug release. With increasing proportion of PLGA75:25, 0.6 dl/g, ester-terminated, the duration of continuous drug release was longer, until the proportion reached 75%, which resulted in continuous drug release for at least 87 days.

Figure 40:
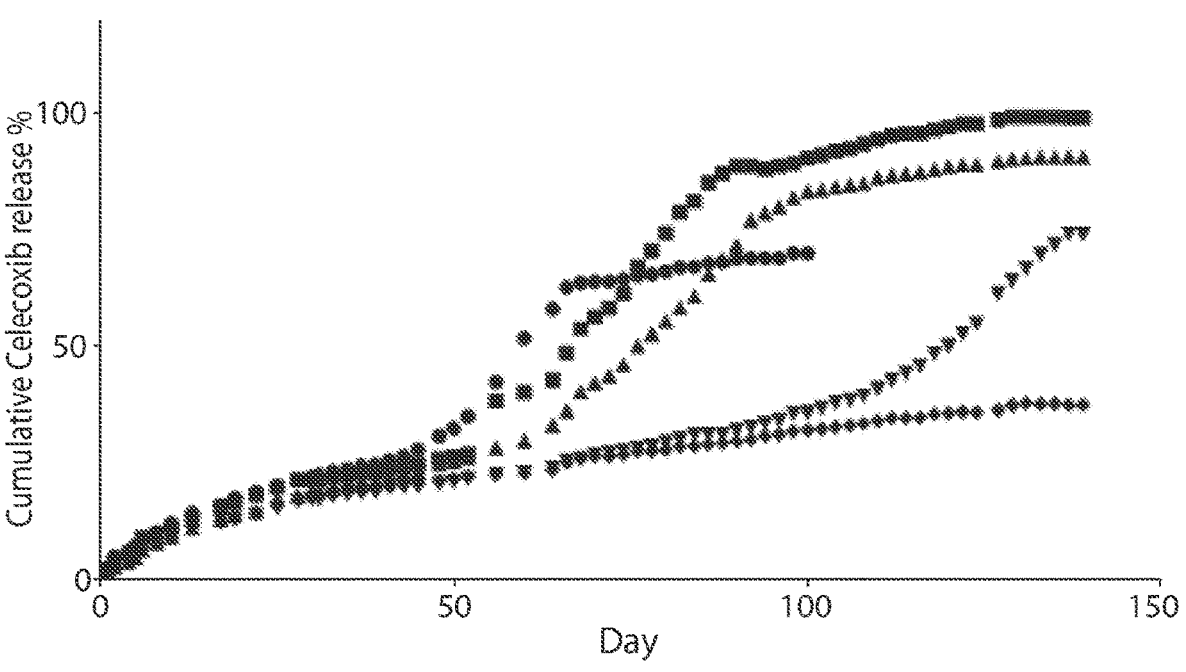

FIG. 40 shows that mixing PLGA50:50, 0.7 dl/g, ester-terminated, with PLGA75:25, 0.6 dl/g, ester-terminated, slowed down celecoxib release. 25% PLGA50:50, 0.7 dl/g, ester-terminated+75% PLGA75:25, 0.6 dl/g, ester-terminated, had continuous celecoxib release over 130 days.

Figure 41:
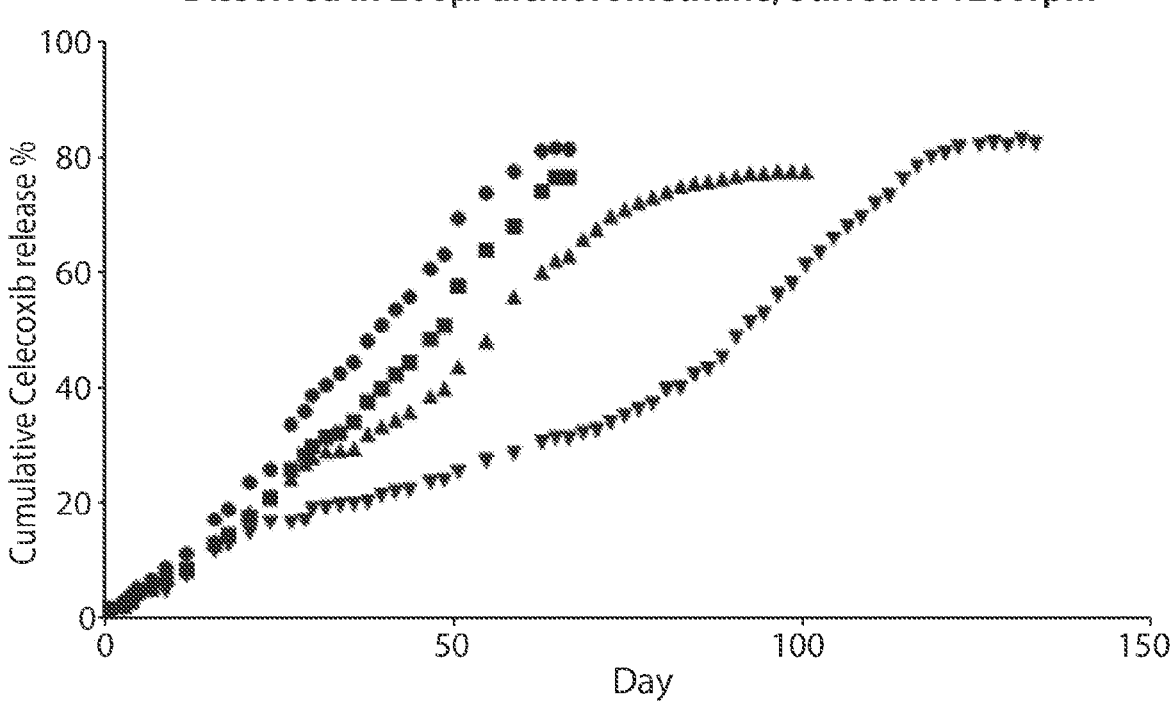

FIG. 41 shows that mixing PLGA75:25, 0.4 dl/g, acid-terminated, with PLGA75:25, 0.6 dl/g, ester-terminated, slowed down celecoxib release. 25% PLGA75:25, 0.4 dl/g, acid-terminated+75% PLGA75:25, 0.6 dl/g, ester-terminated, had continuous celecoxib release over 120 days.

Example 16. Microsphere Formulations of Celecoxib With Lyophilization (I)

Formulations were prepared by dissolving 2.5 mg PLGA75:25, 0.6 dl/g, ester-terminated, and 5 mg, 6 mg, or 7.5 mg celecoxib in 200 μl or 300 μl dichloromethane. The solution was injected into the center of 50 ml of PVA (concentration adjusted to have absorption at 230 nm of 0.160) in a 50 ml beaker, stirred at 1,000 rpm or 1,200 rpm for 2 minutes and stirred at about 500 rpm for 2 hours to evaporate the dichloromethane. The microspheres were harvested by centrifugation at 4,000 g for 5 minutes, washed with 50 ml water for three times, and lyophilized overnight to form a dry powder.

To determine the encapsulation efficiency of celecoxib into the microspheres (encapsulated celecoxib in the microspheres/total celecoxib input), the absorption of the PVA at 230 nm wavelength was measured after microsphere harvesting and normalized against the background absorption of 0.160. This differential was due to the "leaked" celecoxib into the PVA. By subtracting the amount of leaked celecoxib into the PVA from total celecoxib, the amount of encapsulated celecoxib was determined.

To determine the loading ratio of celecoxib in the microspheres (celecoxib/(celecoxib+PLGA)), 10 mg of dry microspheres were added to 40 ml ethanol and shaken overnight to allow complete dissolution of celecoxib in ethanol. Celecoxib concentration in ethanol was analyzed by UV absorption at 230 nm.

For testing celecoxib release from the microspheres, 8 mg of dry microspheres were added to 250 ml of 10 mM PBS and shaken at 80 rpm at 37° C. At each time point in the release study, microspheres were allowed to settle, and an aliquot of 650 μl was taken for measuring UV absorption and added back to the original solution. If the released celecoxib in PBS reached about one third of the fully saturated concentration, 200 ml out of the 250 ml of PBS (without microspheres) was taken out and replaced with fresh 200 ml of PBS. Celecoxib concentration was determined by UV absorption at a wavelength of 230 nm.

Figure 42A:
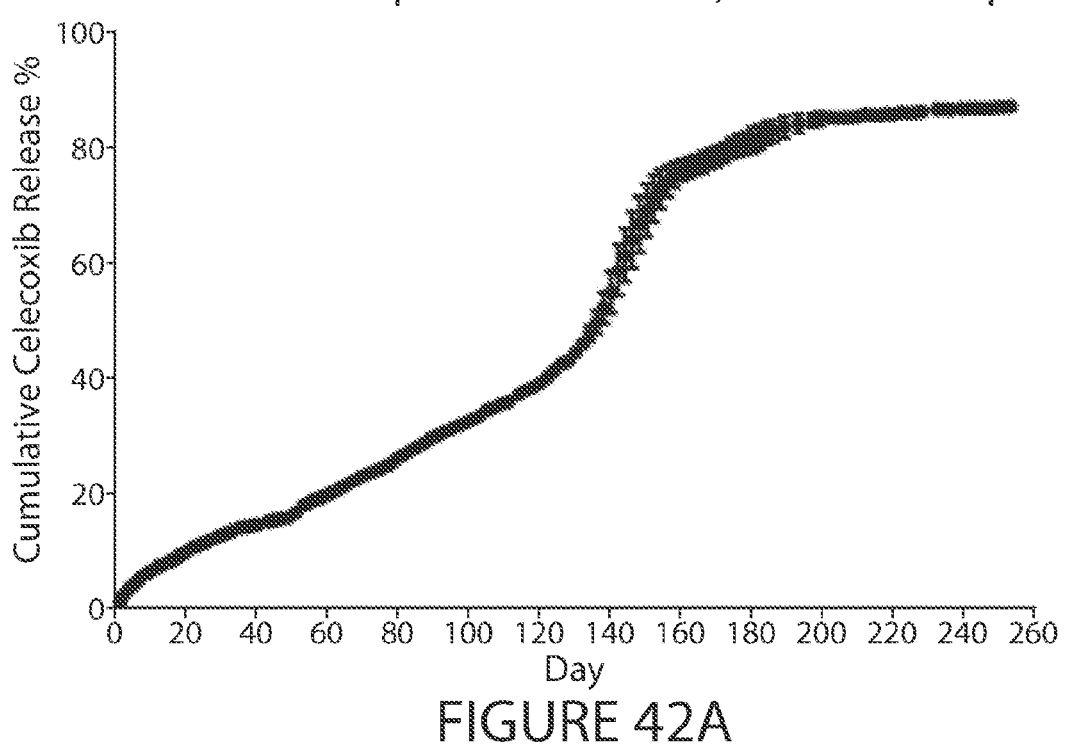
Figure 42B:
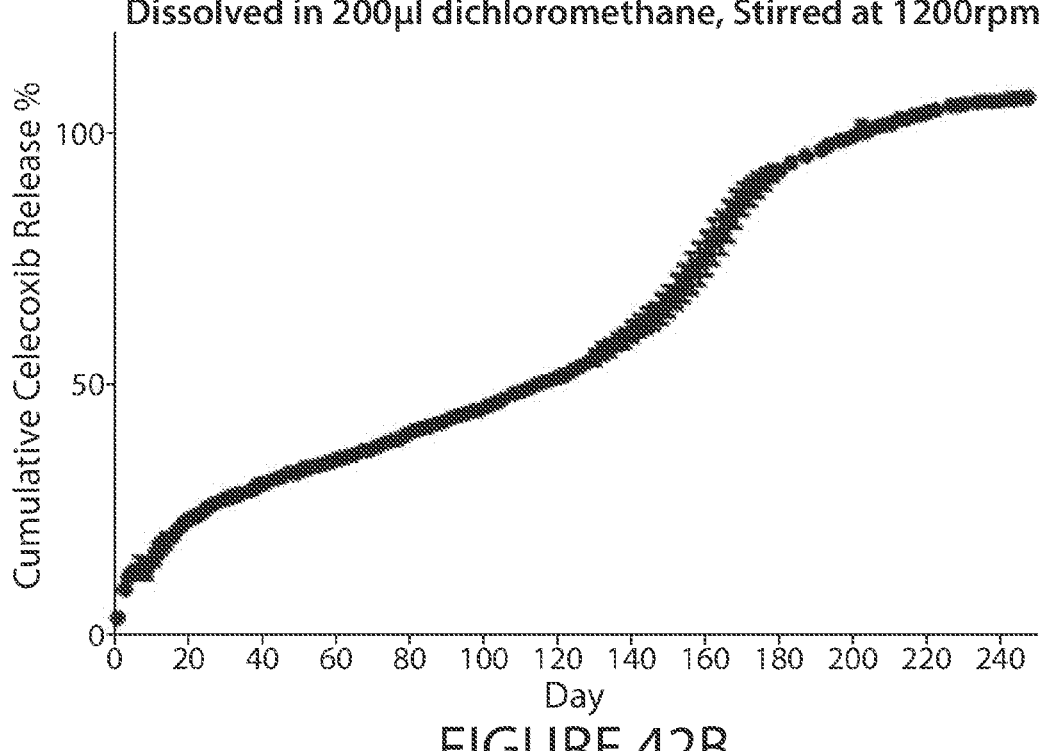
Figure 42C:
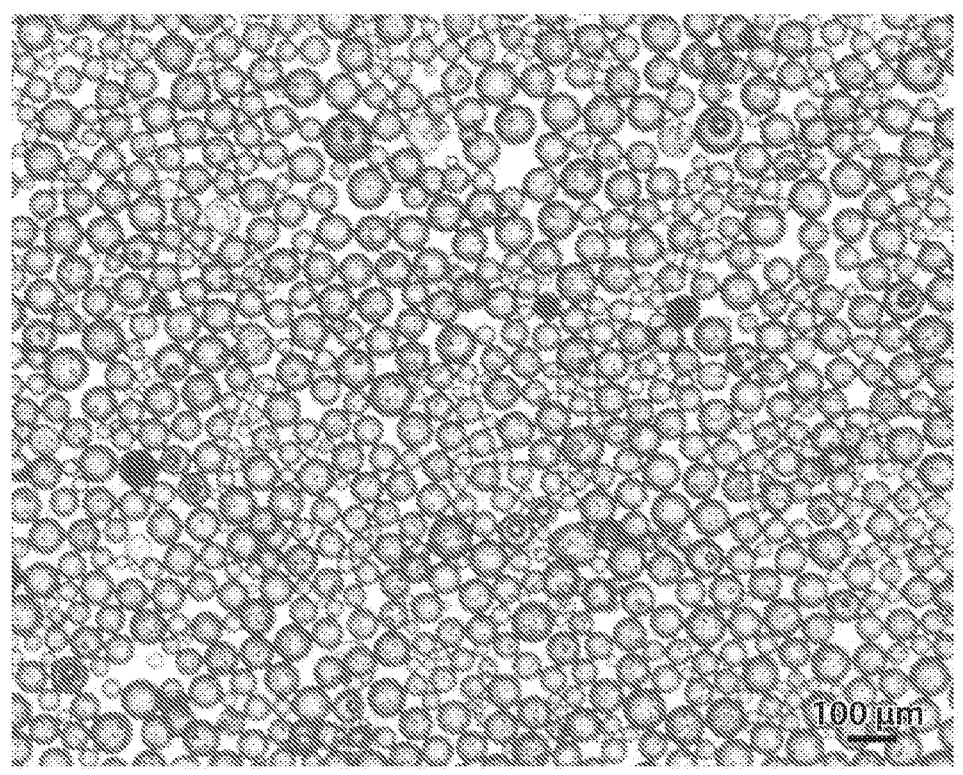
Figure 42D:
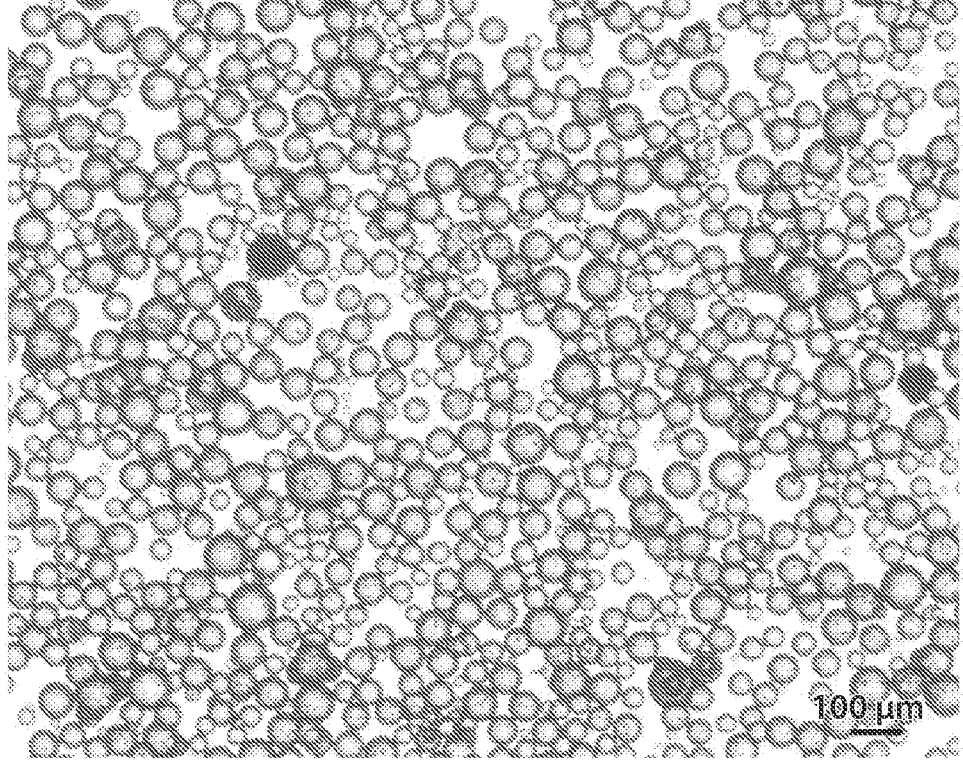

FIGS. 42A and 42B show that 2.5 mg PLGA75:25, 0.6 dl/g, ester-terminated, and 5 mg (FIG. 42A) or 6 mg (FIG. 42B) celecoxib, dissolved in 200 μl dichloromethane and stirred at 1,200 rpm resulted in continuous celecoxib release over at least 180 days. The encapsulation efficiencies for the 5 mg and 6 mg group were 94.4% and 93.8%, respectively. This indicates near complete encapsulation of celecoxib into the microspheres. The loading ratios for the 5 mg and 6 mg group were 62.7% and 62.8%, respectively. FIGS. 42C and 42D show microscopic images of microspheres formed by 2.5 mg PLGA75:25, 0.6 dl/g, ester-terminated and 5 mg (FIG. 42C) or 6 mg (FIG. 42D) celecoxib, dissolved in 200 μl dichloromethane and stirred at 1,200 rpm for 2 minutes, followed by stirring at 500 rpm for 2 hours, harvesting, washing with water, and lyophilization.

Figure 43:
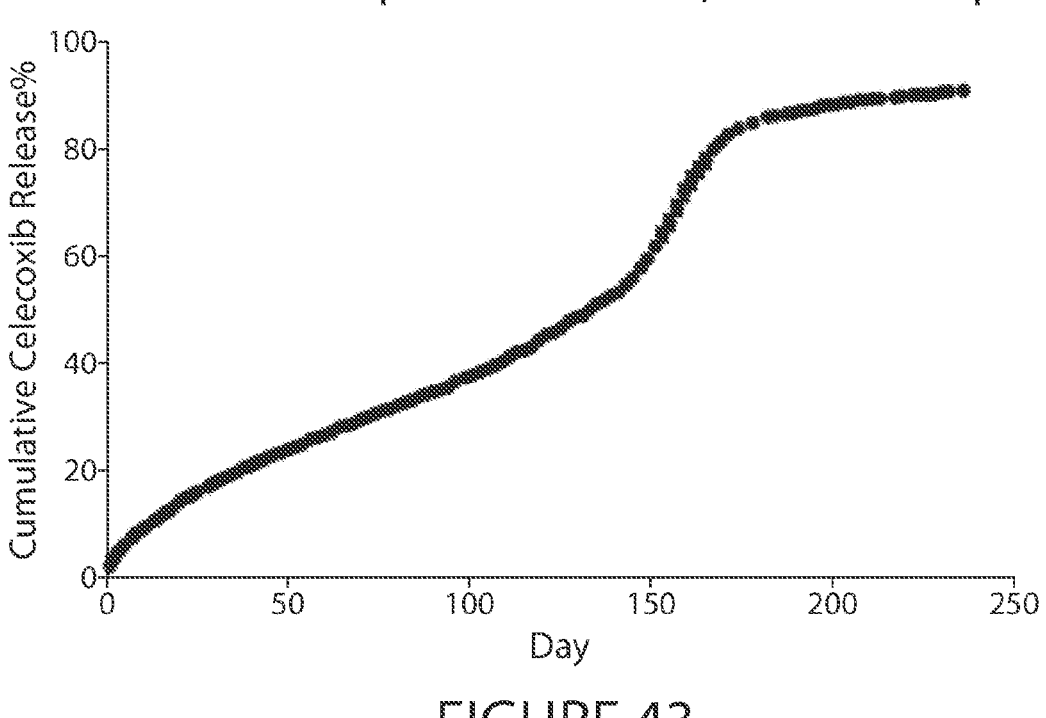
Figure 44:
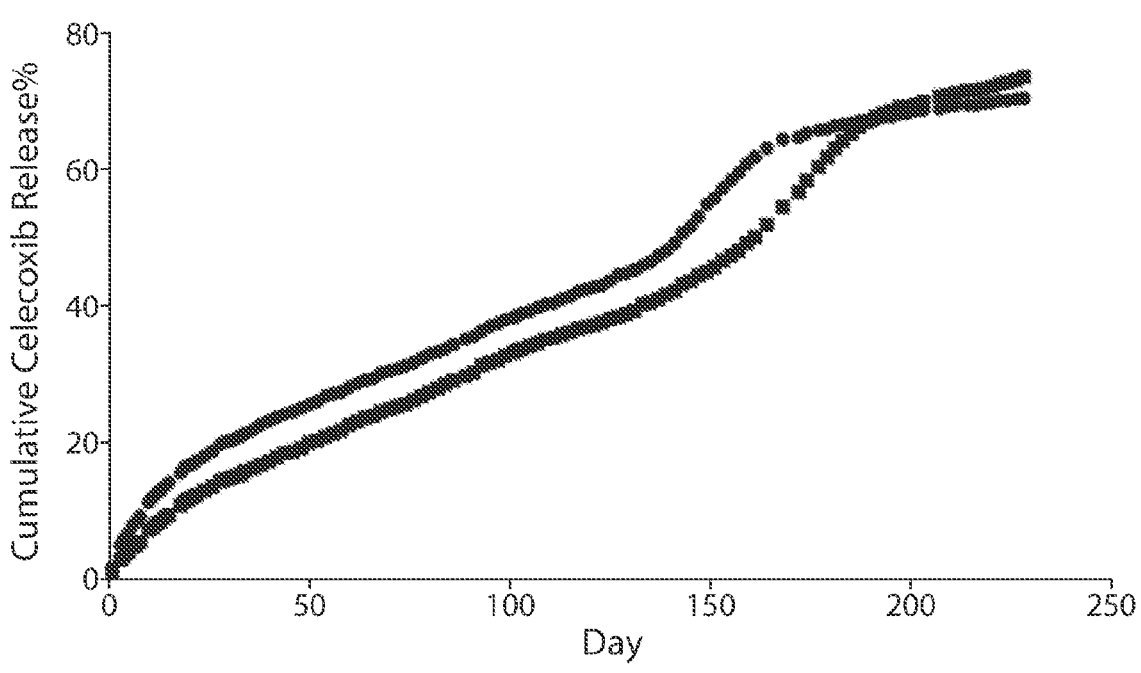
Figure 45:
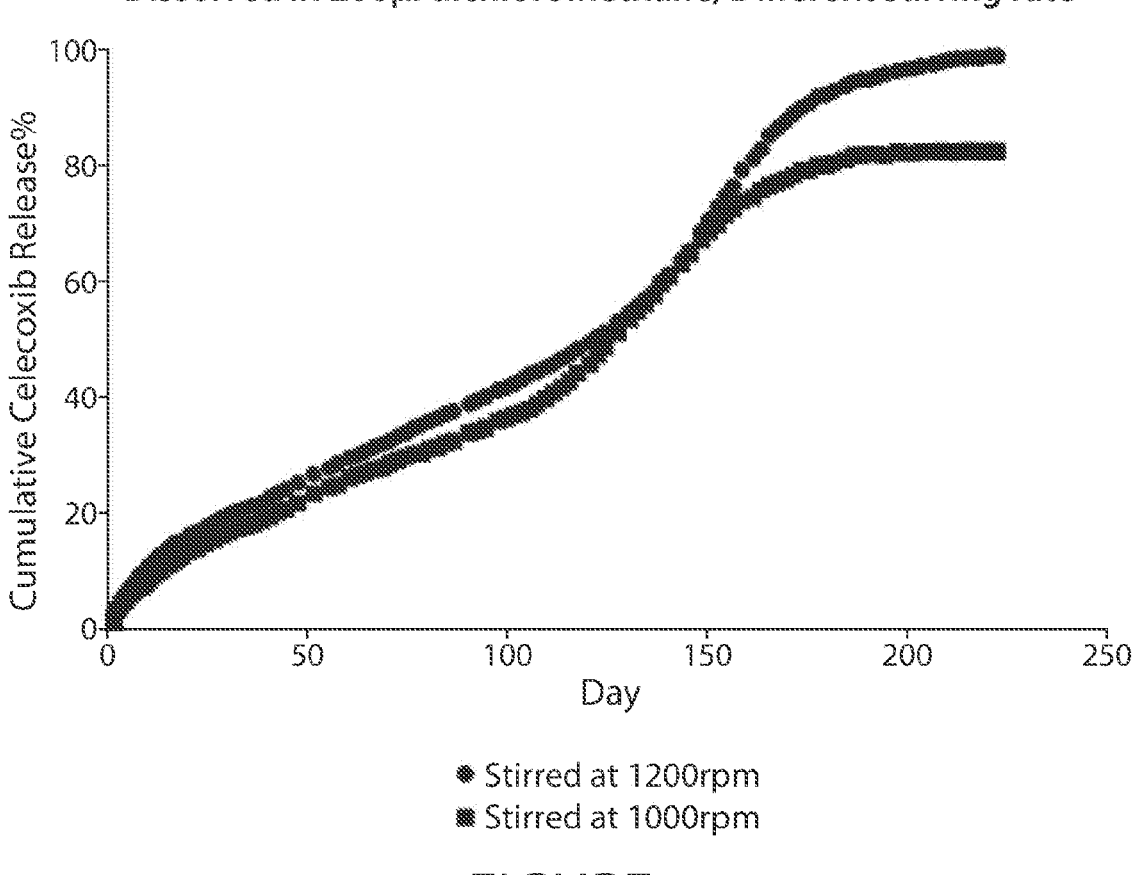

FIG. 43 shows that 2.5 mg PLGA75:25, 0.6 dl/g, ester-terminated, and 6 mg celecoxib, dissolved in 300 μl dichloromethane and stirred at 1,000 rpm resulted in continuous celecoxib release over 175 days. FIG. 44 shows that 2.5 mg PLGA75:25, 0.6 dl/g, ester-terminated, and 7.5 mg celecoxib, dissolved in 200 μl or 300 μl dichloromethane and stirred at 1,200 rpm or 1,000 rpm resulted in continuous celecoxib release over 180 days. FIG. 45 shows that that 2.5 mg PLGA75:25, 0.6 dl/g, ester-terminated, and 5 mg celecoxib, dissolved in 200 μl dichloromethane and stirred at 1,000 rpm or 1,200 rpm resulted in continuous celecoxib release over 180 days.

Example 17. Microsphere Formulations of Celecoxib With Lyophilization (II)

Formulations were prepared by dissolving 2.5 mg PLGA75:25, 0.6 dl/g, ester-terminated, and 5 mg or 6 mg celecoxib in 200 μl dichloromethane. The solution was injected into the center of 50 ml of PVA (concentration adjusted to have absorption at 230 nm of 0.05) in a 50 ml beaker, stirred at 1,000 rpm for 2 minutes and stirred at about 500 rpm for 2 hours to evaporate the dichloromethane. The microspheres were harvested by centrifugation at 4,000 g for 5 minutes, washed with 50 ml water for three times, and lyophilized overnight to form a dry powder.

For testing celecoxib release from the microspheres, 8 mg of dry microspheres were added to 250 ml of 10 mM PBS and shaken at 80 rpm at 37° C. At each time point in the release study, microspheres were allowed to settle, and an aliquot of 650 μl was taken for measuring UV absorption and added back to the original solution. If the released celecoxib in PBS reached about one third of the fully saturated concentration, 200 ml out of the 250 ml of PBS (without microspheres) was taken out and replaced with fresh 200 ml of PBS. Celecoxib concentration was determined by UV absorption at a wavelength of 230 nm.

FIGS. 46A and 46B show that 2.5 mg PLGA75:25, 0.6 dl/g, ester-terminated, and 5 mg (FIG. 46A) or 6 mg (FIG. 46B) celecoxib, dissolved in 200 μl dichloromethane and stirred at 1,000 rpm resulted in continuous celecoxib release over 180 days.

Example 18. Microsphere Formulations of Celecoxib with Lyophilization (III)

Formulations were prepared by dissolving 2.5 mg PLGA75:25, 0.6 dl/g or 0.9 dl/g, ester-terminated, and 5 mg celecoxib in 200 μl dichloromethane. The solution was injected into the center of 50 ml of PVA (concentration adjusted to have absorption at 230 nm of 0.160) in a 50 ml beaker, stirred at 1,200 rpm for 2 minutes and stirred at about 500 rpm for 2 hours to evaporate the dichloromethane. The microspheres were harvested by centrifugation at 4,000 g for 5 minutes, washed with 50 ml water for three times, and lyophilized overnight to form a dry powder.

For testing celecoxib release from the microspheres, 8 mg of dry microspheres were added to 250 ml of 10 mM PBS and shaken at 80 rpm at 37° C. At each time point in the release study, microspheres were allowed to settle, and an aliquot of 650 μl was taken for measuring UV absorption and added back to the original solution. If the released celecoxib in PBS reached about one third of the fully saturated concentration, 200 ml out of the 250 ml of PBS (without microspheres) was taken out and replaced with fresh 200 ml of PBS. Celecoxib concentration was determined by UV absorption at a wavelength of 230 nm. Three samples were analyzed per formulation.

FIG. 47A shows that both PLGA75:25, 0.6 dl/g and 0.9 dl/g, ester-terminated formulations resulted in continuous celecoxib release over least 100 days. The release rate of 0.9 dl/g PLGA was slightly lower than 0.6 dl/g PLGA. FIG. 47B shows a microscopic image of microspheres formed by 2.5 mg PLGA75:25, 0.9 dl/g, ester-terminated and 5 mg celecoxib, dissolved in 200 μl dichloromethane and stirred at 1,200 rpm for 2 minutes, followed by stirring at 500 rpm for 2 hours, harvesting, washing with water, and lyophilization.

Example 19. Pharmacokinetics of the Present Formulation in Lewis Rats 2.5 mg PLGA75:25, 0.6 dl/g, ester-terminated, and 5 mg celecoxib were dissolved in 200 μl dichloromethane, which was injected into the center of 50 ml PVA solution (concentration adjusted to have absorption at 230 nm of 0.160) and stirred at 1,200 rpm for 2 minutes, followed by stirring at about 500 rpm for 2 hours to allow evaporation of dichloromethane. The microspheres were harvested by centrifugation at 4,000 g for 5 minutes, treated for two hours with 100 units/ml penicillin, 100 μg/ml streptomycin, and 0.25 μg/ml amphotericin B, washed with 50 ml sterile water for three times, and lyophilized overnight to form a dry powder ("present formulation"). The dry powder from multiple batches was pooled for injection to rats. A diluent was made as 0.9% NaCl, 0.1% polysorbate-80, and 1% carboxymethylcellulose. Prior to injection to rats, the dry powder was re-suspended in 65 μl of diluent. Celecoxib concentration was analyzed by LC-MS (AB Sciex TRIPLE QUAD 6500+).

Figure 48:
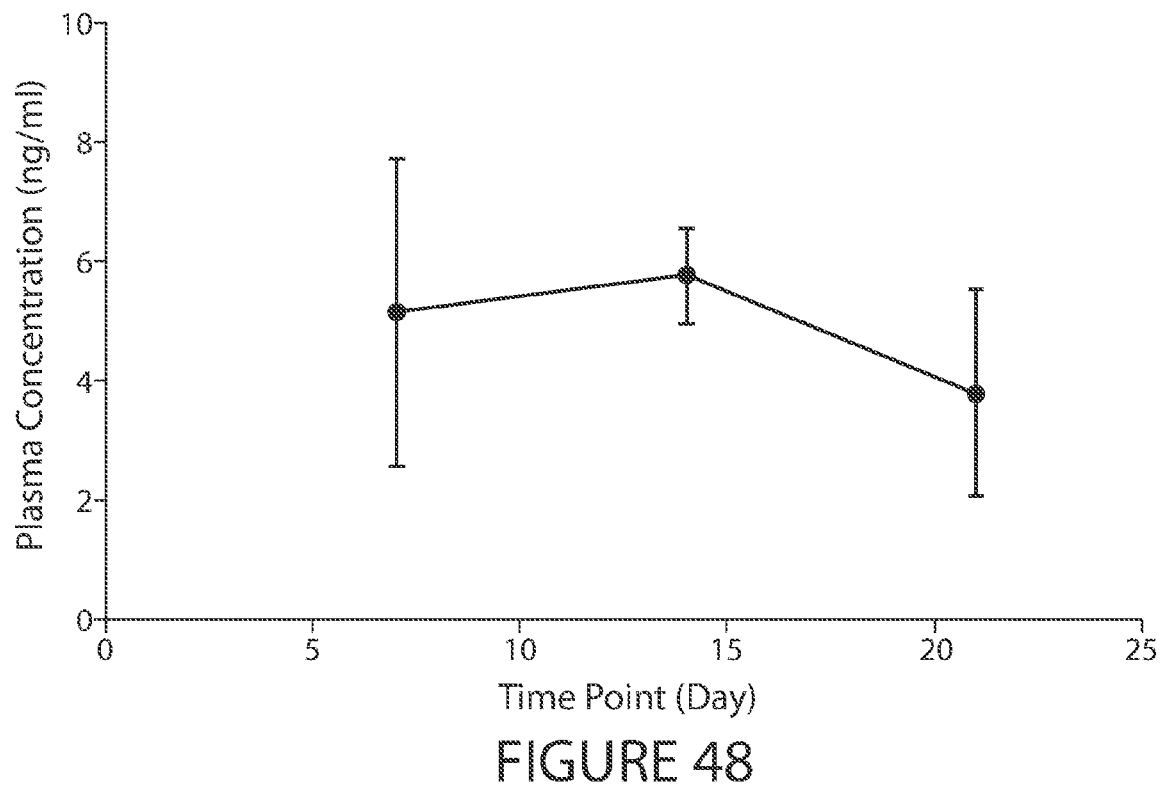

Nine male Lewis rats (250-275 grams) were injected in bilateral knees with 5 mg of the present formulation. Three rats were sacrificed at day 7, 14, and 21 with blood collection. FIG. 48 shows the plasma level of celecoxib, which is much lower than the plasma level observed with human use of oral celecoxib 200 mg QD (705 ng/ml in peak plasma concentration and about 250 ng/ml mean plasma concentration). This suggests a reduced incidence of systemic side effects.

Example 20. Rat Monoiodoacetate (MIA) Osteoarthritis Pain Model 2.5 mg PLGA75:25, 0.6 dl/g, ester-terminated, and 5 mg celecoxib were dissolved in 200 μl dichloromethane, which was injected into the center of 50 ml PVA solution (concentration adjusted to have absorption at 230 nm of 0.160) and stirred at 1,200 rpm for 2 minutes, followed by stirring at about 500 rpm for 2 hours to allow evaporation of dichloromethane. The microspheres were harvested by centrifugation at 4,000 g for 5 minutes, treated for two hours with 100 units/ml penicillin, 100 μg/ml streptomycin, and 0.25 μg/ml amphotericin B, washed with 50 ml sterile water three times, and lyophilized overnight to form a dry powder ("present formulation"). The dry powder from multiple batches was pooled for injection to the left knees of rats. A diluent was made containing 0.9% NaCl, 0.1% polysorbate-80, and 0.5% methylcellulose. Prior to injection, 5 mg of the present formulation was re-suspended in 65 μl of diluent.

Thirty female Sprague-Dawley rats (about 200 grams) were equally divided into three groups: diluent only injection as a negative control; diluent injection with daily oral celecoxib as a positive control; and injection of the present formulation. On day 0, all rats received injection of diluent or the present formulation in the left knee. The positive control group received QD 12.5 mg/kg oral celecoxib from day 0 to day 7, and QD 40 mg/kg oral celecoxib from day 8 to day 10. On day 2, 50 μl of 60 mg/ml monoiodoacetate was injected to the left knee of all rats to induce arthritis. Von Frey filament tests, thermal hyperalgesia tests, and tests for differential weight bearing on hind limbs were performed at five time points: before dosing on day 0; before oral dosing on day 7 and day 10; and 3 hours post-oral dosing on day 7 and day 10. Knee injection of the present formulation resulted in superior pain relief compared to vehicle (diluent only) injection and oral celecoxib. Results are presented in FIGS. 49A-49C.

Von Frey filament test: Mechanical allodynia of the left hind paw was measured by determining withdrawal thresholds to an electronic Von Frey filament (Bioseb, France). The filament was applied perpendicularly to the plantar surface of the paw with increasing force. The force required to induce a reflex paw withdrawal was calculated.

Differential weight bearing test: With a weight balance changing instrument (YLS-11A, Jinan Yi Yan Technology Development Co, China), the rats were tested to register the weight load exerted by the hind paws by means of a force plate inserted in the floor. The mean weight bearing in grams between the MIA injected paw and contra-lateral paw were determined in 10 seconds.

Thermal hyperalgesia test: Thermal hyperalgesia of the left hind paw was measured by using a planter heat test, which measures the paw withdrawal latency period (in seconds) in response to radiant heat.

Example 21. Pharmacokinetics of PLGA-Encapsulated Celecoxib Microspheres in Beadle Dogs 2.5 mg PLGA75:25, 0.6 dl/g, ester-terminated, and 5 mg celecoxib were dissolved in 200 μl dichloromethane, which was injected into the center of 50 ml PVA solution (concentration adjusted to have absorption at 230 nm of 0.160) and stirred at 1,200 rpm for 2 minutes, followed by stirring at about 500 rpm for 2 hours to allow evaporation of dichloromethane. The microspheres were harvested by centrifugation at 4,000 g for 5 minutes, treated for two hours with 100 units/ml penicillin, 100 µg/ml streptomycin, and 0.25 µg/ml amphotericin B, washed with 50 ml sterile water three times, and lyophilized overnight to form a dry powder ("present formulation"). The dry powder from multiple batches was pooled for injection to Beagle dogs. A diluent was made as 0.9% NaCl, 0.1% polysorbate-80, and 1% carboxymethylcellulose. Prior to injection to dogs, the dry powder was re-suspended in 1 ml of diluent.

Nine male Beagle dogs (about 10 kg in weight) received injections of 100 mg of the present formulation in bilateral knee joints. At day 7, 14, and 21, three dogs received blood draw immediately before sacrifice to collect synovial fluid, synovial membrane, femur cartilage, and tibia cartilage from both knees. Celecoxib concentration in these tissues was analyzed by liquid chromatography-mass spectrometry (LC-MS). Briefly, blood was collected from the cephalic vein into tubes with EDTA-K2 as anti-coagulant, and centrifuged at 5,000 rpm for 10 minutes to get plasma. Synovial membrane and cartilage were immersed in acetonitrile with volume (in ml) equal to 5 times the wet weight of the tissue (in g), homogenized with mechanical force, and sonicated for 30 minutes to extract celecoxib. The extracted celecoxib was quantified with Acquity UPLC with MS/MS (API4000 with Analyst 1.6.3 AB Sciex).

FIGS. 50A-50D show celecoxib concentrations in joint tissues (i.e., synovial fluid (FIG. 50A), synovial membrane (FIG. 50B), femur cartilage (FIG. 50C), and tibia cartilage (FIG. 50D)). From day 7 to 21, the geometric mean of synovial fluid concentrations was above 100 ng/ml. The geometric mean of synovial membrane concentrations was above 100,000 ng/ml. The geometric mean of cartilage concentrations was above 1,000 ng/ml. Since the biochemical IC50 of celecoxib is 40 nM (about 15 ng/ml), the observed celecoxib concentrations in vivo greatly exceed the IC50, which indicates sufficient level to deliver therapeutic efficacy.

Figure 51:
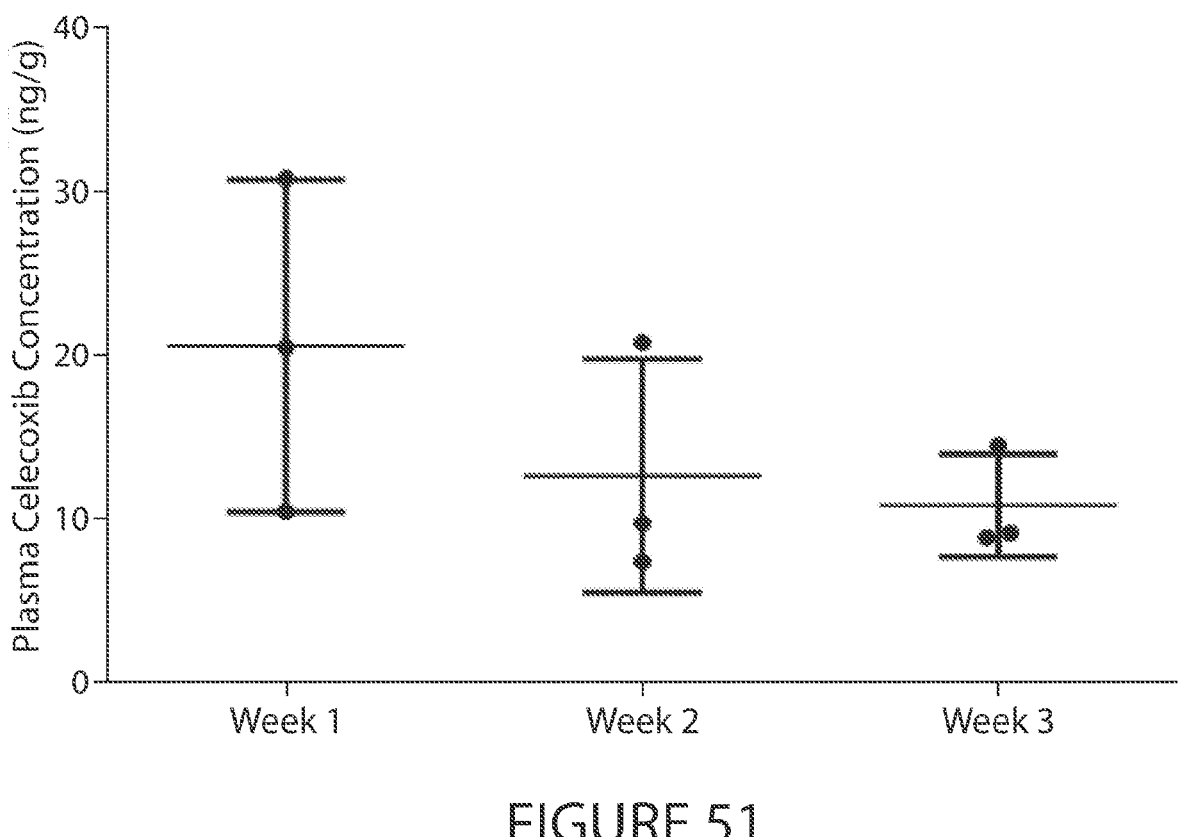

FIG. 51 shows celecoxib concentrations in plasma, which are significantly lower than the peak (705 ng/ml) and mean (about 250 ng/ml) celecoxib concentration in plasma observed in humans at the FDA-approved oral 200 mg QD dose (References: FDA label of celecoxib; SK Paulson et al., "Pharmacokinetics of celecoxib after oral administration in dogs and humans: effect of food and site of absorption" *The Journal of Pharmacology and Experimental Therapeutics*. (2001). 297(2):638-45). The high plasma concentration by oral administration gives rise to systemic side effects in gastrointestinal and cardiovascular systems, among others. The low plasma concentration observed with the present formulation should result in significantly reduced systemic side effects.

In a separate study, three male Beagle dogs (about 10 kg in weight) received QD 5 mg/kg oral celecoxib under overnight fasting condition. After eight days of dosing, at three hours after the final dose (time of peak plasma concentration), the dogs received blood draw and were sacrificed to collect synovial fluid, synovial membrane, and femur cartilage. Celecoxib concentration in these tissues was analyzed by LC-MS. Briefly, blood was collected from the cephalic vein into tubes with EDTA-K2 as anti-coagulant, and centrifuged at 5,000 rpm for 10 minutes to get plasma. Synovial membrane and cartilage were immersed in acetonitrile with volume (in ml) equal to 5 times the wet weight of the tissue (in g), homogenized with mechanical force, and sonicated for 30 minutes to extract celecoxib. The extracted celecoxib was quantified with Acquity UPLC with MS/MS (API4000 with Analyst 1.6.3 AB Sciex).

Figure 52:
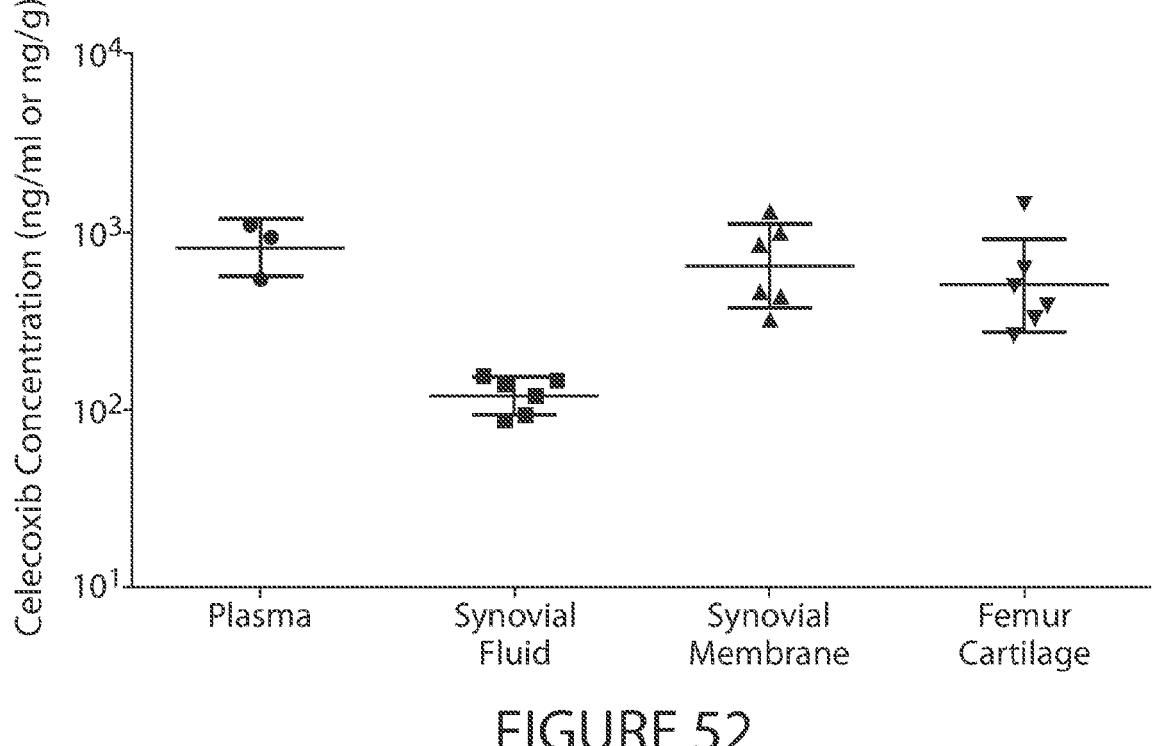

FIG. 52 shows celecoxib concentrations in plasma and joint tissues. The synovial fluid concentration was significantly lower than in plasma, and the levels in plasma, synovial membrane, and femur cartilage were similar.

Surprisingly, the concentration ratio of synovial membrane to synovial fluid, and the concentration ratio of cartilage to synovial fluid were significantly higher for the present formulation than for oral administration of celecoxib. Despite the different routes of administration (knee injection versus oral), the altered distribution of celecoxib among different joint compartments within the same joint was unexpected. In FIGS. 53A and 53B, the geometric mean of the concentration ratio of synovial membrane to synovial fluid is 5.4 for oral celecoxib (FIG. 53A) versus 2,522 for the present formulation as a knee injection (FIG. 53B). The geometric mean of the concentration ratio of femur cartilage to synovial fluid is 4.2 for oral celecoxib versus 49 for the present formulation as a knee injection, which is consistent with the concentration ratio (54) of tibia cartilage to synovial fluid for the present formulation as a knee injection. In other words, the present formulation as a knee injection enabled high enrichment of celecoxib in synovial membrane and cartilage relative to synovial fluid, which is unexpected.

The sites of therapeutic action for celecoxib are synovial membrane and cartilage. The unexpectedly high enrichment in synovial membrane and cartilage relative to synovial fluid is a favorable property, since it permits joint injection of PLGA-encapsulated celecoxib at a much lower dose to achieve therapeutic efficacy, which in turn permits further reducing celecoxib's systemic side effects.

REFERENCES

Anderson, et al., Biodegradation and biocompatibility of PLA and PLGA microspheres, *Advanced Drug Delivery* 28(1997): 5-24.
Bodick, et al., U.S. Pat. No. 9,555,048.
Bouissou, et al., Poly(lactic-co-glycolic-acid) Microspheres. *Polymer in Drug Delivery* (2006): Chapter 7.
H. Chikaura, et al., Effect of particle size on biological response by human monocyte-derived macrophages, *Biosurface and Biotribology*, March 2016. 2(1):18-25.
Cleek et al., Microparticles of poly(DL-lactic-coglycolic acid)/poly(ethylene glycol) blends for controlled drug delivery. *J Control Release* 48(1997):259-268.
FDA Label for Celebrex® (celecoxib).
FDA Label for Zilretta® (a PLGA-triamcinolone-acetonide microsphere formulation).
G. Gaudriault, et al., International Publication No. WO/2017/085561.
T. Green, et al., Polyethylene particles of a "critical size" are necessary for the induction of cytokines by macrophages in vitro, *Biomaterials*, December 1998; 19(24): 2297-2302.
M. Homar, et al., Influence of polymers on the bioavailability of micro-encapsulated celecoxib, *J. of Microencapsulation, November* 2007; 24(7): 621-633.
Hunter et al. (2004) Plasma pharmacokinetics and synovial fluid concentrations after oral administration of single and multiple doses of celecoxib in Greyhounds. *AJVR*. Vol 66, No. 8.

M. Janssen, et al., Celecoxib-loaded PEA microspheres as an auto regulatory drug-delivery system after intra-articular injection, *J. Control Release,* 2016 Dec. 28:244 (Pt. A): 30-40.

J. Matthews, et al., Comparison of the response of primary human peripheral blood mononuclear phagocytes from different donors to challenge with model polyethylene particles of known size and dose, *Biomaterials.* October 2000. 21(20):2033-2044.

Morlock, et al. Erythropoietin loaded microspheres prepared from biodegradable LPLG-PEO-LPLG triblock copolymers: protein stabilization and in vitro release properties. *J Control Release,* 56(1-3) (1998): 105-15.

S. K. Paulson, et al., Pharmacokinetics of celecoxib after oral administration in dogs and humans: effect of food and site of absorption, *The Journal of Pharmacology and Experimental Therapeutics.* (2001) 297(2):638-45.

A. Petit, et al., Release behavior and intra-articular biocompatibility of celecoxib-loaded acetyl-capped PCLA-PEG-PCLA thermogels, *Biomaterials* 35 (2014) 7919-7928.

A. Petit, et al., Sustained intra-articular release of celecoxib from in situ forming gels made of acetyl-capped PCLA-PEG-PCLA triblock copolymers in horses, *Biomaterials* 35 (2015): 426-436.

H. Thakkar, et al., Celecoxib incorporated chitosan microspheres: in vitro and in vivo evaluation, *J. of Drug Targeting,* October-December 2004, Vol. 12 (9-10), pp. 549-557.

H. Thakkar, et al., Enhanced retention of celecoxib-loaded solid lipid nano-particles after intra-articular administration, *Drugs R D* 2007; 8(5):275-285.

Wang, et al. (2011) Intra-discal vancomycin-loaded PLGA microsphere injection for MRSA discitis: an experimental study. *Arch Orthop Trauma Surg.* 131:111-119.

Williems, et al. (2017) Safety of intradiscal injection and biocompatibility of polyester amide microspheres in a canine model predisposed to intervertebral disc degeneration. *Journal of Biomedical Materials Research Part B.* 105(4):707-714.

H. Y. Yang, et al., Applicability of a newly developed bioassay for determining bioactivity of anti-inflammatory compounds in release studies—celecoxib and triamcinolone acetonide released from novel PLGA-based microspheres, *Pharm. Res.* (2015) 32:680-690.

Yeh, The stability of insulin in biodegradable microparticles based on blends of lactide polymers and polyethylene glycol. *J Microencapsul,* 17(6) (2000): 743-56.

What is claimed is:

1. A plurality of biodegradable microspheres, wherein the microspheres (i) have a $d_{90}$ value from 20 μm to 200 μm; (ii) comprise a polylactic-co-glycolic acid copolymer (PLGA) matrix having a lactic acid to glycolic acid molar ratio of from 70:30 to 80:20; (iii) carry a therapeutically effective amount of pharmaceutical celecoxib at a celecoxib loading of 50%-75% by weight (calculated as celecoxib/(celecoxib+PLGA)); and (iv) when present in a suitable joint-related tissue, continuously release celecoxib for at least three months, wherein the celecoxib released per day is from 0.2X mg to 5X mg during the at least three months, where X mg is the average celecoxib released per day, wherein the PLGA is ester-terminated or mixed ester/acid-terminated, and wherein the PLGA has a viscosity of 0.5-0.7, 0.71-1.0, or 0.9-1.3 dl/g.

2. The plurality of biodegradable microspheres of claim 1, wherein the microspheres further comprise polyethylene glycol (PEG).

3. The plurality of biodegradable microspheres of claim 1, wherein the microspheres, when present in a suitable joint-related tissue, continuously release celecoxib for at least six months.

4. The plurality of biodegradable microspheres of claim 1, wherein the microspheres (i) have a lactic acid to glycolic acid molar ratio of from 70:30 to 80:20; and (ii) carry from 1 μg to 2,000 mg of pharmaceutical celecoxib.

5. The plurality of biodegradable microspheres of claim 1, wherein the microspheres have a lactic acid to glycolic acid molar ratio of 75:25.

6. An injectable formulation comprising (a) a pharmaceutically acceptable carrier and (b) a plurality of biodegradable microspheres wherein the microspheres (i) have a $d_{90}$ value from 20 μm to 200 μm; (ii) comprise a polylactic-co-glycolic acid copolymer (PLGA) matrix having a lactic acid to glycolic acid molar ratio of from 70:30 to 80:20; (iii) carry a therapeutically effective amount of pharmaceutical celecoxib at a celecoxib loading of 50%-75% by weight (calculated as celecoxib/(celecoxib+PLGA)); and (iv) when present in a suitable joint-related tissue, continuously release celecoxib for at least three months, wherein the celecoxib released per day is from 0.2X mg to 5X mg during the at least three months, where X mg is the average celecoxib released per day, wherein the PLGA is ester-terminated or mixed ester/acid-terminated, and wherein the PLGA has a viscosity of 0.5-0.7, 0.71-1.0, or 0.9-1.3 dl/g.

7. The formulation of claim 6, wherein the microspheres further comprise polyethylene glycol (PEG).

8. The formulation of claim 6, wherein the microspheres, when present in a suitable joint-related tissue, continuously release celecoxib for at least six months.

9. A method for treating a joint-related disorder in a subject, the method comprising introducing biodegradable microspheres into suitable tissue in or around one or more of the subject's joints, wherein the microspheres (i) have a $d_{90}$ value from 20 μm to 200 μm; (ii) comprise a polylactic-co-glycolic acid copolymer (PLGA) matrix having a lactic acid to glycolic acid molar ratio of from 70:30 to 80:20; (iii) carry a therapeutically effective amount of pharmaceutical celecoxib at a celecoxib loading of 50%-75% by weight (calculated as celecoxib/(celecoxib+PLGA)); and (iv) when present in a suitable joint-related tissue, continuously release celecoxib for at least three months, wherein the celecoxib released per day is from 0.2X mg to 5X mg during the at least three months, where X mg is the average celecoxib released per day, wherein the PLGA is ester-terminated or mixed ester/acid-terminated, and wherein the PLGA has a viscosity of 0.5-0.7, 0.71-1.0, or 0.9-1.3 dl/g.

10. The method of claim 9, wherein the microspheres further comprise polyethylene glycol (PEG).

11. The method of claim 9, wherein the subject is human.

12. The method of claim 9, wherein the subject is a cat, a dog, or a horse.

13. The method of claim 9, wherein the disorder is arthritis.

14. The method of claim 9, wherein the disorder is osteoarthritis.

15. The method of claim 9, wherein the disorder is rheumatoid arthritis.

16. The method of claim 9, wherein the method comprises intra-articularly injecting the biodegradable microspheres into one or both of the subject's knees.

17. The method of claim 9, wherein the microspheres (i) have a lactic acid to glycolic acid molar ratio of from 70:30 to 80:20; and (ii) carry from 1 μg to 2,000 mg of pharmaceutical celecoxib.

18. The method of claim 9, wherein the microspheres have an average lactic acid to glycolic acid molar ratio of 75:25.

19. The method of claim 9, wherein the microspheres have a $d_{90}$ value from 20 μm to 150 μm.

20. The method of claim 9, wherein the microspheres continuously release celecoxib for at least six months.

21. A kit comprising, in separate compartments, (a) a diluent, and (b) plurality of biodegradable microspheres, wherein the microspheres (i) have a $d_{90}$ value from 20 μm to 200 μm; (ii) comprise a polylactic-co-glycolic acid copolymer (PLGA) matrix having a lactic acid to glycolic acid molar ratio of from 70:30 to 80:20; (iii) carry a therapeutically effective amount of pharmaceutical celecoxib at a celecoxib loading of 50%-75% by weight (calculated as celecoxib/(celecoxib+PLGA)); and (iv) when present in a suitable joint-related tissue, continuously release celecoxib for at least three months, wherein the celecoxib released per day is from 0.2X mg to 5X mg during the at least three months, where X mg is the average celecoxib released per day, wherein the PLGA is ester-terminated or mixed ester/acid-terminated, and wherein the PLGA has a viscosity of 0.5-0.7, 0.71-1.0, or 0.9-1.3 dl/g.

22. A plurality of biodegradable microspheres, wherein the microspheres (i) have a $d_{90}$ value from 20 μm to 200 μm; (ii) comprise a polylactic-co-glycolic acid copolymer (PLGA) matrix having a lactic acid to glycolic acid molar ratio of from 70:30 to 80:20; (iii) carry a therapeutically effective amount of pharmaceutical celecoxib at a celecoxib loading of 50%-75% by weight (calculated as celecoxib/(celecoxib+PLGA)); and (iv) when present in a suitable joint-related tissue, continuously release celecoxib for at least three months, wherein the celecoxib so released is characterized by (i) (synovial membrane celecoxib concentration)/(synovial fluid celecoxib concentration) being at least 20, and/or (ii) (joint cartilage celecoxib concentration)/(synovial fluid celecoxib concentration) being at least 10, wherein the celecoxib released per day is from 0.2X mg to 5X mg during the at least three months, where X mg is the average celecoxib released per day, wherein the PLGA is ester-terminated or mixed ester/acid-terminated, and wherein the PLGA has a viscosity of 0.5-0.7, 0.71-1.0, or 0.9-1.3 dl/g.

23. An injectable formulation comprising (a) a pharmaceutically acceptable carrier and (b) a plurality of biodegradable microspheres wherein the microspheres (i) have a doo value from 20 μm to 200 μm; (ii) comprise a polylactic-co-glycolic acid copolymer (PLGA) matrix having a lactic acid to glycolic acid molar ratio of from 70:30 to 80:20; (iii) carry a therapeutically effective amount of pharmaceutical celecoxib at a celecoxib loading of 50%-75% by weight (calculated as celecoxib/(celecoxib+PLGA)); and (iv) when present in a suitable joint-related tissue, continuously release celecoxib for at least three months, wherein the celecoxib so released is characterized by (i) (synovial membrane celecoxib concentration)/(synovial fluid celecoxib concentration) being at least 20, and/or (ii) (joint cartilage celecoxib concentration)/(synovial fluid celecoxib concentration) being at least 10, wherein the celecoxib released per day is from 0.2X mg to 5X mg during the at least three months, where X mg is the average celecoxib released per day, wherein the PLGA is ester-terminated or mixed ester/acid-terminated, and wherein the PLGA has a viscosity of 0.5-0.7, 0.71-1.0, or 0.9-1.3 dl/g.

24. A composition comprising biodegradable microspheres for use in a method for treating a joint-related disorder in a subject, the method comprising introducing the biodegradable microspheres into suitable tissue in or around one or more of the subject's joints, wherein the microspheres (i) have a $d_{90}$ value from 20 μm to 200 μm; (ii) comprise a polylactic-co-glycolic acid copolymer (PLGA) matrix having a lactic acid to glycolic acid molar ratio of from 70:30 to 80:20; (iii) carry a therapeutically effective amount of pharmaceutical celecoxib at a celecoxib loading of 50%-75% by weight (calculated as celecoxib/(celecoxib+PLGA)); and (iv) when present in a suitable joint-related tissue, continuously release celecoxib for at least three months, wherein the celecoxib so released is characterized by (i) (synovial membrane celecoxib concentration)/(synovial fluid celecoxib concentration) being at least 20, and/or (ii) (joint cartilage celecoxib concentration)/(synovial fluid celecoxib concentration) being at least 10, wherein the celecoxib released per day is from 0.2X mg to 5X mg during the at least three months, where X mg is the average celecoxib released per day, wherein the PLGA is ester-terminated or mixed ester/acid-terminated, and wherein the PLGA has a viscosity of 0.5-0.7, 0.71-1.0, or 0.9-1.3 dl/g.

25. A kit comprising, in separate compartments, (a) a diluent, and (b) a plurality of biodegradable microspheres, wherein the microspheres (i) have a $d_{90}$ value from 20 μm to 200 m; (ii) comprise a polylactic-co-glycolic acid copolymer (PLGA) matrix having a lactic acid to glycolic acid molar ratio of from 70:30 to 80:20; (iii) carry a therapeutically effective amount of pharmaceutical celecoxib at a celecoxib loading of 50%-75% by weight (calculated as celecoxib/(celecoxib+PLGA)); and (iv) when present in a suitable joint-related tissue, continuously release celecoxib for at least three months, wherein the celecoxib so released is characterized by (i) (synovial membrane celecoxib concentration)/(synovial fluid celecoxib concentration) being at least 20, and/or (ii) (joint cartilage celecoxib concentration)/(synovial fluid celecoxib concentration) being at least 10, wherein the celecoxib released per day is from 0.2X mg to 5X mg during the at least three months, where X mg is the average celecoxib released per day, wherein the PLGA is ester-terminated or mixed ester/acid-terminated, and wherein the PLGA has a viscosity of 0.5-0.7, 0.71-1.0, or 0.9-1.3 dl/g.

* * * * *